United States Patent [19]

Reiffen et al.

[11] Patent Number: 4,886,814
[45] Date of Patent: Dec. 12, 1989

[54] SUBSTITUTED THIAZOLES AND OXAZOLES AND 2-HYDROXY-MORPHOLINES

[75] Inventors: Manfred Reiffen; Rudolf Hurnaus, both of Biberach; Robert Sauter, Laupheim; Wolfgang Grell, Biberach; Eckhard Rupprecht, Aulendorf-Tannhausen, all of Fed. Rep. of Germany

[73] Assignee: Dr. Karl Thomas GmbH, Biberach an der Riss, Fed. Rep. of Germany

[21] Appl. No.: 93,415

[22] Filed: Sep. 4, 1987

[30] Foreign Application Priority Data

| Mar. 13, 1986 [DE] | Fed. Rep. of Germany | 3608290 |
| Jun. 28, 1986 [DE] | Fed. Rep. of Germany | 3621775 |
| May 25, 1987 [DE] | Fed. Rep. of Germany | 3717560 |

[51] Int. Cl.$^4$ ............... A61K 31/425; A61K 31/445; C07D 277/24; C07D 417/12
[52] U.S. Cl. ................... 514/326; 514/365; 514/866; 546/229; 548/203
[58] Field of Search ............ 514/326, 365, 866; 546/229; 548/203

[56] References Cited

U.S. PATENT DOCUMENTS 4,826,990  5/1989  Musser et al. ............. 548/203

*Primary Examiner*—Mary C. Lee
*Assistant Examiner*—M. S. Howard
*Attorney, Agent, or Firm*—D. E. Frankhouser; M-E. M. Timbers; A. R. Stempel

[57] ABSTRACT

Substituted thiazoles, oxazoles and 2-hydroxy morpholine compounds useful in the treatment of diabetes mellitus and obesity are described.

13 Claims, No Drawings

SUBSTITUTED THIAZOLES AND OXAZOLES AND 2-HYDROXY-MORPHOLINES

European Patent Application No. EP-A-5848, published on Dec. 12, 1979 discloses certain substituted thiazoles and oxazoles which maybe represented by the formula:

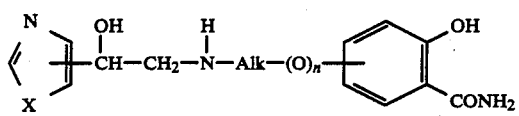

in which X represents an oxygen or sulphur atom, Alk represents a straight-chained or branched alkylene group with 2 to 5 carbon atoms, and n represents the number 0 or 1. These compounds are said to have valuable pharmacological properties, in particular a stimulating action on cardiac 8-receptors, for example a positive inotropic or positive chronotropic action.

DESCRIPTION OF THE INVENTION

It has now been found, surprisingly, that new substituted thiazoles and oxazoles of the formula

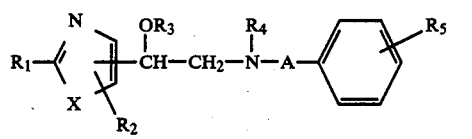

their optical isomers (or "enantiomers") and diastereomers (or "diastereoisomers"), since these new compounds contain one or more optically active carbon atoms, and their acid addition salts have valuable properties.

Thus, the lactams of formula I, in which $R_3$ and $R_4$ taken together represent —$CH_2CO$—, their optical isomers and diastereomers, represent valuable intermediates for the preparation of the morpholines of formula I, in which $R_3$ and $R_4$ together represent an ethylene (—$CH_2CH_2$—) group. These morpholines and the other compounds of formula I (excepting the lactams), the optical isomers, diastereomers and acid addition salts thereof, in particular the physioogically tolerated acid addition salts with inorganic or organic acids, have quite different pharmacological properties than as noted above in said EP-A-5848 application, namely, an action on the metabolism, preferentially a blood sugar lowering and body fat reducing action as well as causing a reduction in the levels of atherogenic β-lipoproteins VLDL and LDL. In addition, some of the above mentioned compounds also have an anabolic action.

In the above formula I:
A is n-alkylene of 2 to 3 carbons, optionally mono- or di-substituted with methyl or ethyl,
X is oxygen or sulphur,
$R_1$ is selected from the group consisting of hydrogen, halo of atomic weight less than 80 (i.e., fluoro, chloro and bromo), trifluoromethyl, alkyl, phenyl, piperidino, amino, alkylamino, dialkylamino, alkanoylamino and benzoylamino,
$R_2$ is hydrogen or alkyl,
$R_3$ is hydrogen or alkyl, optionally substituted in the 2- or 3-position by hydroxyl,
$R_4$ is selected from the group consisting of hydrogen, alkyl, optionally substituted by a member selected from the group consisting of phenyl, carboxyl, alkoxycarbonyl, cyano, and, in the 2- or 3-position, hydroxyl, and alkenyl,
$R_3$ together with $R_4$ is selected from the group consisting of alkoxycarbonylmethylene, —$CH_2CH_2$—, —$CH_2CO$— and —$COCH_2$—, and
$R_5$ is selected from the group consisting of hydroxyl, alkoxy, carboxyl, alkoxycarbonyl, aminocarbonyl, alkylaminocarbonyl, dialkylaminocarbonyl, alkoxy having 1 to 6 carbons and substituted by a terminal member selected from the group consisting of carboxyl, alkoxycarbonyl, aminocarbonyl, alkylaminocarbonyl and dialkylaminocarbonyl, alkoxy having 2 to 7 carbons and substituted by a terminal member selected from the group consisting of hydroxyl, alkoxy, phenylalkoxy, amino, alkylamino, dialkylamino, pyrrolidino, piperidino and hexamethyleneimino and ethylene optionally substituted by alkyl and substituted by a terminal member selected from the group consisting of carboxyl, alkoxycarbonyl, aminocarbonyl, alkylaminocarbonyl and dialkylaminocarbonyl,
wherein said alkyl, alkoxy and alkanoyl each contain, unless indicated otherwise, 1 to 3 carbons, and said alkenyl contains 3 to 5 carbons.

Typical examples included in said defined symbols are:
for A: the ethylene, 1-methyl-ethylene, 2-methyl-ethylene, 1-ethyl-ethylene, 2-ethyl-ethylene, 1,2-dimethyl-ethylene, 1,1-dimethyl-ethylene, 1,1-diethyl-ethylene, 1-ethyl-1-methyl-ethylene, 2,2-dimethyl-ethylene, 2,2-diethyl-ethylene, 2-ethyl-2-methyl-ethylene, n-propylene, 1-methyl-n-propylene, 2-methyl-n-propylene, 3-methyl-n-propylene, 1-ethyl-n-propylene, 2-ethyl-n-propylene, 3-ethyl-n-propylene, 1,1-dimethyl-n-propylene, 1,1-diethyl-n-propylene, 2,3-dimethyl-n-propylene, 3,3-dimethyl-n-propylene or 3-ethyl-3-methyl-n-propylene group,
for $R_1$: the hydrogen, fluorine, chlorine or bromine atom, the trifluoromethyl, methyl, ethyl, n-propyl, isopropyl, phenyl, amino, methylamino, ethylamino, isopropylamino, dimethylamino, diethylamino, di-n-propylamino, N-ethyl-methylamino, N-ethyl-n-propylamino, piperidino, formylamino, acetamino, propionylamino or benzoylamino group,
for $R_2$: the hydrogen atom or the methyl, ethyl, n-propyl or isopropyl group,
for $R_3$: the hydrogen atom, the methyl, ethyl, n-propyl, isopropyl, 2-hydroxy-ethyl, 2-hydroxy-propyl or 3-hydroxy-propyl group or
for $R_3$ together with $R_4$: the ethylene group in which one methylene group can be replaced by a carbonyl group, the methoxycarbonylmethylene, ethoxycarbonylmethylene, n-propoxycarbonylmethylene or isopropoxycarbonylmethylene group,
for $R_4$: the hydrogen atom, the methyl, ethyl, n-propyl, isopropyl, benzyl, 1-phenylethyl, 2-phenylethyl, 3-phenyl-n-propyl, carboxymethyl, 1-carboxyethyl, 2-carboxyethyl, 3-carboxy-n-propyl, methoxycarbonylmethyl, ethoxycarbonylmethyl, n-propoxycarbonylmethyl, 1-ethoxycarbonylethyl, 2-methoxycarbonylethyl, 2-ethoxycarbonylethyl, 3-isopropoxycarbonyl-n-propyl, cyanomethyl, 1-cyanoethyl, 2-cyanoethyl, 3-cyano-n-propyl, 2-hydroxy-ethyl, 3-hydroxy-n-propyl, allyl, buten-2-yl, buten-3-yl or penten-2-yl group, and for R$_5$: the hydroxyl, methoxy, ethoxy, n-propoxy, isopropoxy, carboxyl, methoxycarbonyl, ethoxycarbonyl, n-propoxycarbonyl, aminocarbonyl, methylaminocarbonyl, ethylaminocarbonyl, isopropylaminocarbonyl, dimethylaminocarbonyl, diethylaminocarbonyl, di-n-propylaminocarbonyl, N-ethyl-methylaminocarbonyl, N-ethyl-isopropylaminocarbonyl, 2-hydroxy-ethoxy, 3-hydroxy-n-propoxy, 4-hydroxy-n-butoxy, 5-hydroxy-n-pentoxy, 6-hydroxy-n-hexoxy, 7-hydroxy-n-heptoxy, 2-methoxy-ethoxy, 2-ethoxy-ethoxy, 2-n-propoxy-ethoxy, 3-ethoxy-n-propoxy, 4-methoxy-n-butoxy, 6-ethoxy-n-hexoxy, 2-phenethoxy-ethoxy, 2-amino-ethoxy, 2-methylamino-ethoxy, 2-dimethylamino-ethoxy, 2-isopropylamino-ethoxy, 2-di-n-propylamino-ethoxy, 2-(1-pyrrolidino)ethoxy, 2-(1-piperidino)ethoxy, 2-(1-hexamethyleneimino)ethoxy, 3-amino-n-propoxy, 6-amino-n-hexoxy, 7-methylamino-n-heptoxy, 3-diethylamino-n-propoxy, 3-(1-piperidino)-n-propoxy, 4-dimethylamino-n-butoxy, carboxymethoxy, 2-carboxyethoxy, 3-carboxy-n-propoxy, 4-carboxy-n-butoxy, methoxycarbonylmethoxy, 2-methoxycarbonyl-ethoxy, 6-methoxycarbonylhexoxy, ethoxycarbonylmethoxy, 2-ethoxycarbonyl-ethoxy, 3-ethoxycarbonyl-n-propoxy, n-propoxycarbonylmethoxy, 2-isopropoxycarbonyl-ethoxy, 4-n-propoxycarbonyl-n-butoxy, aminocarbonylmethoxy, 2-aminocarbonyl-ethoxy, 4-aminocarbonyl-n-butoxy, methylaminocarbonylmethoxy, 2-methylaminocarbonyl-ethoxy, dimethylaminocarbonyl-methoxy, 2-dimethyl-aminocarbonylethoxy, 4-dimethylaminocarbonyl-n-butoxy, diethylaminocarbonylmethoxy, 2-diethyl-aminocarbonyl-ethoxy, 2-di-n-propylaminocarbonyl-ethoxy, 2-carboxyethenyl, 2-carboxy-1-methyl-ethenyl, 2-carboxy-2-methyl-ethenyl, 2-carboxy-1-ethyl-ethenyl, 2-carboxy-1-n-propyl-ethenyl, 2-methoxycarbonylethenyl, 2-methoxy-carbonyl-1-methylethenyl, 2-ethoxycarbonylethenyl, 2-ethoxy-carbonyl-1-methylethenyl or 2-isopropoxycarbonylethenyl group.

In addition to the compounds mentioned in the Examples, the following compounds which are embraced by the above-mentioned formula I may also be mentioned, by way of example:

N-[2-(4-Carbomethoxymethoxyphenyl)-1-methylethyl]-2-hydroxy-2-(2-dimethylamino-thiazol-4-yl)ethanamine, N-[2-(4-Carbomethoxymethoxyphenyl)-1-methylethyl]-2-hydroxy-2-(2-methylamino-thiazol-4-yl)ethanamine, N-[2-(4-Carbomethoxymethoxyphenyl)-1-methylethyl]-2-hydroxy-2-(2-amino-thiazol-4-yl)ethanamine, N-[2-(4-Carbomethoxymethoxyphenyl)-1-methylethyl]-2-hydroxy-2-(2-trifluoromethyl-thiazol-5-yl)ethanamine, N-[2-(4-Carbomethoxymethoxyphenyl)-1-methylethyl]-2-hydroxy-2-(2-trifluoromethyl-4-methyl-thiazol-5-yl)ethanamine, N-[2-(4-Carbomethoxymethoxyphenyl)-1-methylethyl]-2-methoxy-2-(2-trifluoromethyl-thiazol-4-yl)ethanamine, N-[2-(4-Carbomethoxymethoxyphenyl)-1-methylethyl]-N-methyl-2-methoxy-2-(2-trifluoromethyl-thiazol-4-yl)ethanamine, N-[2-(4-Carbomethoxymethoxyphenyl)-1-methylethyl]-N-methyl-2-hydroxy-2-(2-methyl-thiazol-4-yl)ethanamine, N-[2-(4-Carbomethoxymethoxyphenyl)-1-methylethyl]-N-allyl-2-hydroxy-2-(2-trifluoromethyl-thiazol-4-yl)ethanamine, N-[2-(4-Carbomethoxymethoxyphenyl)-1-methylethyl]-N-(2-phenylethyl)-2-hydroxy-2-(2-trifluoromethyl-thiazol-4-yl)ethanamine, N-[2-(4-Carbomethoxymethoxyphenyl)-1-methylethyl]-N-cyanomethyl-2-hydroxy-2-(2-trifluoromethyl-thiazol-4-yl)ethanamine, N-[2-(4-Methylaminocarbonylmethoxyphenyl)-1-methylethyl]-2-hydroxy-2-(2-dimethylamino-thiazol-4-yl)ethanamine, N-[2-(4-Methylaminocarbonylmethoxyphenyl)-1-methylethyl]-2-hydroxy-2-(2-methylamino-thiazol-4-yl)ethanamine, N-[2-(4-Methylaminocarbonylmethoxyphenyl)-1-methylethyl]-2-hydroxy-2-(2-trifluoromethyl-thiazol-5-yl)ethanamine, N-[2-(4-Methylaminocarbonylmethoxyphenyl)-1-methylethyl]-2-hydroxy-2-(2-methyl-thiazol-5-yl)ethanamine, N-[2-(4-Methylaminocarbonylmethoxyphenyl)-1-methylethyl]-2-hydroxy-2-(2-trifluoromethyl-4-methyl-thiazol-5-yl)ethanamine, N-[2-(4-Methylaminocarbonylmethoxyphenyl)-1-methylethyl]-2-hydroxy-2-(2-methyl-oxazol-4-yl)ethanamine, N-[2-(4-Methylaminocarbonylmethoxyphenyl)-1-methylethyl]-2-methoxy-2-(2-trifluoromethyl-thiazol-4-yl)ethanamine, N-[2-(4-Methylaminocarbonylmethoxyphenyl)-1-methylethyl]-N-methyl-2-methoxy-2-(2-trifluoromethyl-thiazol-4-yl)ethanamine, N-[2-(4-Methylaminocarbonylmethoxyphenyl)-1-methylethyl]-N-methyl-2-hydroxy-2-(2-methyl-thiazol-4-yl)ethanamine, N-[2-(4-Methylaminocarbonylmethoxyphenyl)-1-methylethyl]-2-methoxy-2-(2-methyl-thiazol-4-yl)ethanamine, N-[2-(4-Methylaminocarbonylmethoxyphenyl)-1-methylethyl]-N-allyl-2-hydroxy-2-(2-trifluoromethyl-thiazol-4-yl)ethanamine, N-[2-(4-Methylaminocarbonylmethoxyphenyl)-1-methylethyl]-N-(2-phenylethyl)-2-hydroxy-2-(2-trifluoromethyl-thiazol-4-yl)ethanamine, N-[2-(4-Methylaminocarbonylmethoxyphenyl)-1-methylethyl]-N-cyanomethyl-2-hydroxy-2-(2-trifluoromethyl-thiazol-4-yl)ethanamine, N-[2-(4-Methylaminocarbonylmethoxyphenyl)ethyl]-2-hydroxy-2-(2-trifluoromethyl-thiazol-4-yl)ethanamine, N-[2-(4-Methylaminocarbonylmethoxyphenyl)ethyl]-2-hydroxy-2-(2-methyl-thiazol-4-yl)ethanamine, N-[2-(4-Aminocarbonylmethoxyphenyl)-1-methylethyl]-N-(2-hydroxyethyl)-2-hydroxy-2-(2-trifluoromethylthiazol-4-yl)ethanamine, N-[2-(4-(6-Hydroxyhexoxy)phenyl)-1-methylethyl]-2-hydroxy-2-(2-methyl-thiazol-4-yl)ethanamine, N-[2-(4-(2-(1-Piperidino)ethoxy)phenyl)-1-methylethyl]-2-hydroxy-2-(2-trifluoromethyl-thiazol-4-yl)ethanamine, N-[2-(4-(2-Methylaminoethoxy)phenyl)-1-methylethyl]-2-hydroxy-2-(2-methyl-thiazol-4-yl)ethanamine, N-[2-(4-Methylaminocarbonylmethoxyphenyl)-1-methylethyl]-2-hydroxy-2-(2-methyl-thiazol-4-yl)ethanamine, N-[2-(4-Aminocarbonylmethoxyphenyl)-1-methylethyl]-2-(2-methyl-thiazol-4-yl)morpholine, N-[2-(4-Carbomethoxyphenyl)-1-methylethyl]-2-(2-trifluoromethyl-thiazol-4-yl)morpholine,
N-[2-(4-(2-(1-Piperidino)ethoxy)phenyl)-1-methylethyl]-2-(2-trifluoromethyl-thiazol-4-yl)morpholine,
Methyl 3-[2-(4-carbomethoxymethoxyphenyl)-1-methylethyl]-5-(2-methyl-thiazol-4-yl)-2-oxazolidine carboxylate,
Methyl 3-[2-(4-aminocarbonylmethoxyphenyl)-1-methylethyl]-5-(2-methyl-thiazol-4-yl)-2-oxazolidine carboxylate,
Methyl 3-[2-(4-methylaminocarbonylmethoxyphenyl)-1-methylethyl]-5-(2-methyl-thiazol-4-yl)-2-oxazolidine carboxylate,
Methyl 3-[2-(4-carbomethoxymethoxyphenyl)ethyl]-5-(2-trifluoromethyl-thiazol-4-yl)-2-oxazolidine carboxylate,
Methyl 3-[2-(4-aminocarbonylmethoxyphenyl)-1-methylethyl]-5-(2-trifluoromethyl-thiazol-4-yl)-2-oxazolidine carboxylate,
Methyl 3-[2-(4-methylaminocarbonylmethoxyphenyl)-1-methylethyl]-5-(2-trifluoromethyl-thiazol-4-yl)-2-oxazolidine carboxylate,
Methyl 3-[2-(4-carboxymethoxyphenyl)-1-methylethyl]-5-(2-trifluoromethyl-thiazol-4-yl)-2-oxazolidine carboxylate,
Methyl 3-[2-(4-(6-hydroxyhexoxy)phenyl)-1-methylethyl]-5-(2-trifluoromethyl-thiazol-4-yl)-2-oxazolidinecarboxyate,
Methyl 3-[2-(4-(2-hydroxyethoxy)phenyl)-1-methylethyl]-5-(2-trifluoromethyl-thiazol-4-yl)-2-oxazolidine carboxylate,
Methyl 3-[2-(4-(2-methylaminoethoxy)phenyl)-1-methylethyl]-5-(2-trifluoromethyl-thiazol-4-yl)-2-oxazolidine carboxylate,
Methyl 3-[2-(4-(2-(1-piperidino)ethoxy)phenyl)-1-methylethyl]-5-(2-trifluoromethyl-thiazol-4-yl)-2-oxazolidine carboxylate,
Methyl 3-[3-(4-carboxamidophenyl)-1-methylpropyl]-5-(2-trifluoromethyl-thiazol-4-yl)-2-oxazolidine carboxylate,
N-[2-(4-Methylaminocarbonylmethoxyphenyl)-1-methylethyl]-2-hydroxy-2-(2-chloro-thiazol-4-yl)ethanamine,
N-[2-(4-Carbomethoxymethoxyphenyl)-1-methylethyl]-2-methoxy-2-(2-chloro-thiazol-4-yl)ethanamine,
N-[2-(4-Carbomethoxymethoxyphenyl)-1-methylethyl]-N-methyl-2-hydroxy-2-(2-chloro-thiazol-4-yl)ethanamine,
N-[2-(4-Carbomethoxymethoxyphenyl)-1-methylethyl]-N-methyl-2-methoxy-2-(2-chloro-thiazol-4-yl)ethanamine,
Methyl N-[2-(4-carbomethoxymethoxyphenyl)-1-methylethyl]-5-(2-chloro-thiazol-4-yl)-2-oxazolidine carboxylate,
N-[2-(4-(2-Ethoxyethoxy)phenyl)-1-methylethyl]-N-(2-hydroxyethyl)-2-hydroxy-2-(2-chloro-thiazol-4-yl)ethanamine,
Methyl 3-[2-(4-(2-carbomethoxy-1-methylethenyl)phenyl)-1-methylethyl]-5-(2-chloro-thiazol-4-yl)-2-oxazolidine carboxylate,
N-[2-(4-(2-Hydroxyethoxy)phenyl)-1-methylethyl]-2-hydroxy-2-(2-methyl-oxazol-4-yl)ethanamine,
N-[2-(4-Carbomethoxymethoxyphenyl)-1-methylethyl]-2-(2-methyl-oxazol-4-yl)morpholine,
N-[2-(4-Carbomethoxymethoxyphenyl)-1-methylethyl]-N-(2-hydroxyethyl)-2-hydroxy-2-(2-methyl-oxazol-4-yl)ethanamine,
Methyl 3-[2-(4-(2-carbomethoxy-1-methylethenyl)phenyl)-1-methyl-ethyl]-5-(2-methyl-oxazol-4-yl)-2-oxazolidine carboxylate,
N-[2-(4-(2-Hydroxyethoxy)phenyl)-1-methylethyl]-N-methyl-2-hydroxy-2-(2-trifluoromethyl-thiazol-4-yl)ethanamine,
N-[2-(4-Carbomethoxymethoxyphenyl)-1-methylethyl]-N-(2-hydroxyethyl)-2-methoxy-2-(2-trifluoromethyl-thiazol-4-yl)ethanamine,
N-[2-(4-(2-Hydroxyethoxy)phenyl)-1-methylethyl]-2-methoxy-2-(2-trifluoromethyl-thiazol-4-yl)ethanamine,
N-[2-(4-(2-Hydroxyethoxy)phenyl)-1-methylethyl]-2-(2-trifluoromethyl-thiazol-4-yl)morpholin-6-one,
N-[2-(4-Carboxymethoxyphenyl)-1-methylethyl]-2-(2-trifluoromethyl-thiazol-4-yl)morpholin-6-one,
N-[2-(4-Carbomethoxymethoxyphenyl)-1-methylethyl]-2-(2-chloro-thiazol-4-yl)morpholin-6-one,
N-[2-(4-Methylaminocarbonylmethoxyphenyl)-1-methylethyl]-2-(2-trifluoromethyl-thiazol-4-yl)morpholin-6-one,
N-[2-(4-Aminocarbonylmethoxyphenyl)-1-methylethyl]-N-(2-hydroxyethyl)-2-hydroxy-2-(2-trifluoromethyl-thiazol-4-yl)ethanamine,
N-[2-(4-Methylaminocarbonylmethoxyphenyl)-1-methylethyl]-N-(2-hydroxyethyl)-2-hydroxy-2-(2-trifluoromethyl-thiazol-4-yl)ethanamine,
N-[2-(4-Hydroxyethoxy)phenyl)-1-methylethyl]-N-carbethoxymethyl-2-hydroxy-2-(2-trifluoromethyl-thiazol-4yl)ethanamine,
N-[2-(4-(2-Methoxyethoxy)phenyl)-1-methylethyl]-2-hydroxy-2-(trifluoromethyl-thiazol-4-yl)ethanamine,
N-[2-(4-(2-Methoxyethoxy)phenyl)-1-methylethyl]-2-(2-trifuuoromethyl-thiazol-4-yl)morpholine,
N-[2-(4-Carboxymethoxyphenyl)-1-methylethyl]-N-methyl-2-hydroxy-2-(2-trifluoromethyl-thiazol-4-yl)ethanamine,
N-[2-(4-(2-Ethoxyethoxy)phenyl)-1-methylethyl]-2-hydroxy-2-(2-chloro-thiazol-4-yl)ethanamine,
N-[2-(4-(2-Ethoxyethoxy)phenyl)-1-methylethyl]-2-(2-chloro-thiazol-4-yl)morpholine,
N-[2-(4-(2-phenethoxyethoxy)phenyl)-1-methylethyl]-2-hydroxy-2-(2-chloro-thiazol-4-yl)ethanamine,
N-[2-(4-(2-phenethoxyethoxy)phenyl)-1-methylethyl]-2-(2-chloro-thiazol-4-yl)morpholine,
N-[2-(4-(2-phenethoxyethoxy)phenyl)-1-methylethyl]-N-(2-hydroxyethyl)-2-hydroxy-2-(2-chloro-thiazol-4-yl)ethanamine and
Methyl 3-[2-(4-(2-ethoxyethoxy)phenyl)-1-methylethyl]-5-(2-trifluoromethyl-thiazol-4-yl)-2-oxazolidine carboxylate,
their optical isomers, their diastereomers and their acid addition salts.

However, preferred compounds of formula I are those in which

A is ethylene or n-propylene, optionally substituted by methyl,

X is oxygen or sulphur $R_1$ is selected from the group consisting of hydrogen, chloro, alkyl, trifluoromethyl, phenyl, amino, methylamino, dimethylamino, piperidino, acetylamino and benzoylamino, $R_2$ is hydrogen or methyl, $R_3$ is hydrogen or methyl, $R_4$ is selected from the group consisting of hydrogen, methyl, 2-hydroxyethyl, carboxymethyl, carbethoxymethyl, and benzyl, R<sub>3</sub> together with R<sub>4</sub> is selected from the group consisting of methoxycarbonylmethylene, —CH<sub>2</sub>CH<sub>2</sub>—, and —COCH<sub>2</sub>—, and R<sub>5</sub> is selected from the group consisting of hydroxy, methoxy, carboxy, methoxycarbonyl, ethoxycarbonyl, aminocarbonyl, carboxymethoxy, methoxycarbonylmethoxy, ethoxycarbonylmethoxy, aminocarbonylmethoxy, methylaminocarbonylmethoxy, 2-hydroxyethoxy, 2-ethoxyethoxy, 2-phenethoxyethoxy, 2-aminoethoxy, 2-methylaminoethoxy, 2-(1-piperidino)-ethoxy, 6-hydroxy-n-hexoxy and 2-carbomethoxy-1-methylethenyl, and the optical isomers and diastereomers thereof and physiologically acceptable acid addition salts thereof with inorganic or organic acids.

However, particularly preferred compounds are those of the general formula

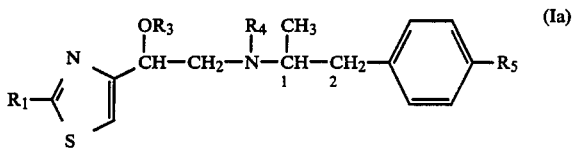

(Ia)

in which

R<sub>1</sub> is selected from the group consisting of chloro, methyl and trifluoromethyl, R<sub>3</sub> is hydrogen, R<sub>4</sub> is selected from the group consisting of hydrogen, methyl, 2-hydroxyethyl and carbethoxymethyl, R<sub>3</sub> together with R<sub>4</sub> is ethylene or methoxycarbonylmethylene, R<sub>5</sub> is selected from the group consisting of carboxymethoxy, carbomethoxymethoxy, ethoxycarbonylmethoxy, aminocarbonylmethoxy, methylaminocarbonylmethoxy, 2-methylaminoethoxy, 2-hydroxyethoxy and 2-carbomethoxy-1-methylethenyl, and the optical isomers and diastereomers thereof and physiologically acceptable acid addition salts thereof with inorganic or organic acids.

The new compounds of formula I are obtained according to the following processes:

(a) reaction of a compound of the general formula

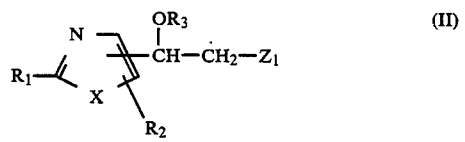

(II)

with a compound of the general formula

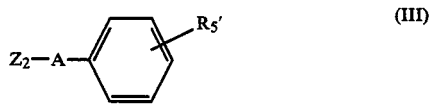

(III)

(in which

R<sub>1</sub> to R<sub>3</sub>, A and X each are as hereinbefore defined,

Z<sub>1</sub> represents a nucleophilic leaving group, and Z<sub>2</sub> represents a R<sub>4</sub>—NH group, or Z<sub>2</sub> represents a nucleophilic leaving group, and Z<sub>1</sub> represents a R<sub>4</sub>—NH group, R<sub>4</sub> being as hereinbefore defined, and R<sub>5</sub>' has the meanings mentioned hereinbefore for R<sub>5</sub>, it not being possible, however, for R<sub>5</sub>' to represent any of the alkoxycarbonylmethoxy groups mentioned hereinbefore, and it being possible for a carboxyl, amino or alkylamino group contained in the radical R<sub>5</sub> to be protected by a protecting group), and, where appropriate, subsequent elimination of a protecting group which has been used.

Examples of suitable nucleophilic leaving groups are halogen atoms or sulphonyloxy groups, for example a chlorine, bromine or iodine atom, the methanesulphonyloxy, p-toluenesulphonyloxy or ethoxysulphonyloxy group, and examples of suitable protecting groups for a carboxyl group are the benzyl, tert.butyl, tetrahydropyranyl, trimethylsilyl, benzyloxymethyl, 2-chloroethyl or methoxyethyl groups, or a phenacyl group such as the benzoylmethyl group, and examples of suitable protecting groups for an amino or alkylamino group are the acetyl, benzoyl, tert.butoxycarbonyl, benzyloxycarbonyl, ethoxycarbonyl or benzyl groups.

The reaction is expediently carried out in a solvent or solvent mixture, such as acetone, diethyl ether, methylformamide, dimethylformamide, dimethyl sulphoxide, benzene, chlorobenzene, tetrahydrofuran, benzene/tetrahydrofuran, dioxane or in an excess of the compounds of formulae II and/or III which are used and, where appropriate, in the presence of an acid building agent, for example an alcoholate such as potassium tert.butylate, an alkali metal hydroxide or potassium hydroxide, an alkali metal carbonate such as potassium carbonate, an alkali metal amide such as sodamide, an alkali metal hydride such as sodium hydride, a tertiary organic base such as triethylamine, N,N-diisopropylethylamine or pyridine, it also being possible for the latter simultaneously to serve as solvent, or of a reaction accelerator such as potassium iodide, depending on the reactivity of the radical which can undergo nucleophilic exchange, expediently at temperatures between 0° and 150° C., preferably at temperatures between 50° and 120° C., for example at the boiling point of the solvent used. However, it is also possible to carry out the reaction without a solvent. However, the reaction is particularly advantageously carried out in the presence of a tertiary organic base or of an excess of the amine of formula II or III which is used.

The subsequent elimination, where appropriate, of a protecting group which has been used is preferably carried out by hydrolysis in an aqueous solvent, for example in water, isopropanol/water, tetrahydrofuran/water or dioxane/water, in the presence of an acid such as hydrochloric acid or sulphuric acid, or in the presence of an alkali metal base such as sodium hydroxide or potassium hydroxide, at temperatures between 0° and 100° C., preferably at the boiling point of the reaction mixture. The elimination of a benzyl or benzyloxycarbonyl radical is, however, preferably effected by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures between 0° and 50° C., but preferably at room temperature, and under a hydrogen pressure of 1 to 7 bar, but preferably 3 to 5 bar.

(b) Reduction of a Schiff's base, which is optionally formed in the reaction mixture, of the formula

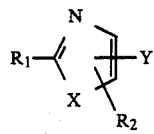

(in which
R₁, R₂ and X are as hereinbefore defined, and Y represents a group of the formula

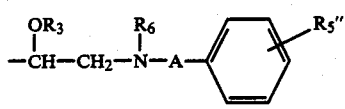

or

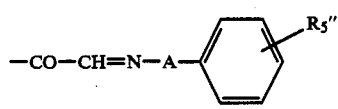

R₃ and A being as hereinbefore defined,
R₅'' having the meanings mentioned hereinbefore for R₅, but it being possible for an amino or alkylamino group contained in the radical R₅ to be protected by a protecting group, and
R₆ together with an α hydrogen atom of the adjacent carbon atom of the radical A representing a further bond), and, where appropriate, subsequent elimination of a protecting group which has been used.

Examples of suitable protecting groups for an amino or alkylamino group are the acetyl, benzoyl, tert-butoxy-carbonyl, benzyloxycarbonyl, ethoxycarbonyl or benzyl groups.

The reduction is carried out in a suitable solvent such as methanol, ethanol, diethyl ether, tetrahydrofuran, dioxane, ethyl acetate or ethanol/ethyl acetate, with a metal hydride such as lithium aluminium hydride, diborane, sodium cyanoborohydride or borane/dimethyl sulphide, but preferably with sodium borohydride, or with hydrogen in the presence of a hydrogenation catalyst such as platinum, palladium/charcoal or Raney nickel, under a hydrogen pressure of 1 to 5 bar, or with hydrazine in the presence of a hydrogenation catalyst such as platinum, palladium/charcoal or Raney nickel, at temperatures between 0° and 50° C., preferably at room temperature. On reduction with a complex metal hydride such as lithium aluminium hydride, diborane or borane/dimethylsulphide it is possible for a carbonyl group present in the radical R₅'' also to be reduced to a methylene group.

The subsequent elimination, where appropriate, of a protecting group which has been used is preferably effected by hydrolysis in an aqueous solvent, for example, in water, isopropanol/water, tetrahydrofuran/water or dioxane/water, in the presence of an acid such as hydrochloric or sulphuric acid, or in the presence of an alkali metal base such as sodium hydroxide or potassium hydroxide, at temperatures of between 0° and 100° C., preferably at the boiling point of the reaction mixture. However, the elimination of a benzyl or benzyloxycarbonyl radical is preferably effected by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures of between 0° and 50° C., but preferably at room temperature, and under a hydrogen pressure of 1 to 7 bar, but preferably of 3 to 5 bar.

(c) For the preparation of compounds of the general formula I in which R₃ and R₄ are as hereinbefore defined, but in which R₃ and R₄ do not represent an ethylene group in which the methylene group adjacent to the N atom has been replaced by a carbonyl group:

reductive amination of a carbonyl compound of the general formula

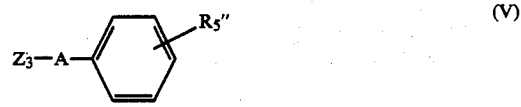

(in which
A is as hereinbefore defined,
R₅'' has the meanings mentioned hereinbefore for R₅ but it being possible for an amino or alkylamino group contained in the radical R₅ to be protected by a protecting group, and
Z₃ together with a hydrogen atom of the adjacent carbon atom of the radical A representing an oxygen atom), with an amine of the general formula

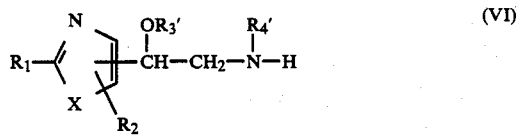

(in which
R₁, R₂ and X are as hereinbefore defined,
R₃' and R₄' have the meanings mentioned hereinbefore for R₃ and R₄, but R₃ and R₄ together not denoting an ethylene group in which the methylene group adjacent to the N atom has been replaced by a carbonyl group) in the presence of a suitable reducing agent and, where appropriate, subsequent elimination of a protecting group which has been used.

Examples of suitable protecting groups for an amino or alkylamino group are the acetyl, benzoyl, tert-butoxy-carbonyl, benzyloxycarbonyl, ethoxycarbonyl or benzyl groups.

The reductive amination is carried out in a suitable solvent such as methanol, ethanol, tetrahydrofuran, dioxane or acetonitrile, in the presence of a suitable reducing agent such as a suitable complex metal hydride, but preferably in the presence of sodium cyanoborohydride, at a pH of 5 to 7, at temperatures of between 0° and 50° C., but preferably at room temperature.

The subsequent elimination, where appropriate, of a protecting group which has been used is preferably effected by hydrolysis in an aqueous solvent, for example in water, isopropanol/water, tetrahydrofuran/water or dioxane/water, in the presence of an acid such as hydrochloric acid or sulphuric acid, or in the presence of an alkali metal base such as sodim hydroxide or potassium hydroxide, at temperatures of between 0° and 100° C., but preferably at the boiling point of the reaction mixture. However, the elimination of a benzyl or benzyloxycarbonyl radical is preferably carried out by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures of between 0° and 50° C., but preferably at room temperature, and under a hydrogen pressure of 1 to 7 bar, but preferably of 3 to 5 bar.

(d) For the preparation of compounds of formula I in which R$_3$ represents a hydrogen atom:

reduction of a compound, which is optionally formed in the reaction mixture, of the general formula

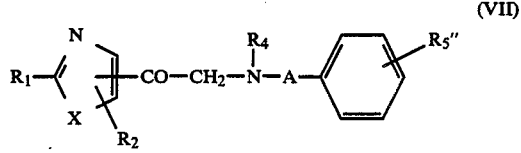

(VII)

(in which

A, X, R$_1$, R$_2$ and R$_4$ are as hereinbefore defined, and R$_5''$ has the meanings mentioned hereinbefore for R$_5$ but it being possible for an amino or alkylamino group contained in the radical R$_5$ to be protected by a protecting group), and, where appropriate, subsequent elimination of a protecting group which has been used.

Examples of suitable protecting groups for an amino or alkylamino group are the acetyl, benzoyl, tert-.butoxy-carbonyl, benzyloxycarbonyl, ethoxycarbonyl or benzyl groups.

The reduction is preferably carried out in a suitable solvent such as methanol, ethanol, diethyl ether or tetrahydrofuran, in the presence of a metal hydride such as sodium borohydride, lithium aluminium hydride, diborane, borane/dimethyl sulphide or sodium cyanoborohydride, but preferably with sodium borohydride in methanol or ethanol, between 0° and 40° C., but preferably at room temperature.

On reduction with a complex metal hydride such as lithium aluminum hydride, diborane or borane/ dimethylsulphide, it is possible for a carbonyl group present in the radical R$_5''$ also to be reduced to a methylene group.

The subsequent elimination, where appropriate, of a protecting group which has been used is preferably effected by hydrolysis in an aqueous solvent, for example in water, isopropanol/water, tetrahydrofuran/water or dioxane/water, in the presence of an acid such as hydrochloric acid or sulphuric acid, or in the presence of an alkali metal base such as sodium hydroxide or.-potassium hydroxide, at temperatures between 0° and 100° C., preferably at the boiling point of the reaction mixture. However, the elimination of a benzyl of benzyloxy carbonyl radical is preferably effected by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures of between 0° and 50° C., but preferably at room temperature, and under a hydrogen pressure of 1 to 7 bar, but preferably of 3 to 5 bar.

(e) For the preparation of compounds of formula I in which R$_3$ and R$_4$ together represent an alkoxycarbonylmethylene group:

reaction of a compound of the formula

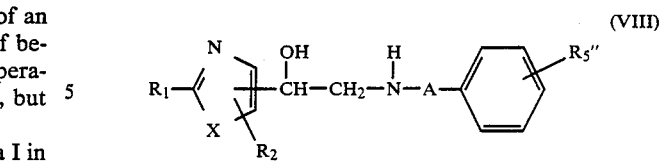

(VIII)

(in which

A, X, R$_1$ and R$_2$ are as hereinbefore defined and R$_5''$ has the meanings mentioned hereinbefore for R$_5$, but it being possible for an amino or alkylamino group contained in the radical R$_5$ to be protected by a protecting group) with a compound of the genera formula

O=CH—COOR$_7$ (IX)

(in which

R$_7$ represents an alkyl group with 1 to 3 carbon atoms) and, where appropriate, subsequent elimination of a protecting group which has been used.

Examples of suitable protecting groups for an amino or alkylamino group are the trityl, fluorenylmethyloxycarbonyl, benzyloxycarbonyl or benzyl groups.

The reaction is expediently carried out in a solvent such as methylene chloride, chloroform, dioxane, benzene or toluene and, where appropriate, in the presence of a water-abstracting agent such as p-toluenesulphonic acid or a molecular sieve, at temperatures between 0° C. and the boiling point of the solvent used, but preferably in benzene or toluene under azeotropic distillation of the reaction mixture.

The subsequent elimination, where appropriate, of a protecting group which has been used is preferably effected by hydrolysis under mild acid or basic conditions in an aqueous solvent, for example in water, isopropanol/water, tetrahydrofuran/water or dioxane/water, in the presence of an acid such as acetic acid or trifluoroacetic acid, or under non-aqueous conditions with tert.organic bases such as triethylamine or diazabicycloundecene (DBU), but preferably by hydrogenolysis, for example with hydrogen in the presence of a catalyst such as palladium/charcoal in a solvent such as methanol, ethanol, ethyl acetate or glacial acetic acid, under a hydrogen pressure of 1 to 7 bar, but preferably of 3 to 5 bar, at temperatures between 0° and 50° C., but preferably at room temperature.

(f) For the preparation of compounds of formula I in which R$_5$ represents an alkoxy group with 1 to 3 carbon atoms, an alkoxy group which has 1 to 6 carbon atoms and which is substituted by a terminal carboxyl, alkoxycarbonyl, aminocarbonyl, alkylaminocarbonyl or dialkylaminocarbonyl group, or an alkoxy group which has 2 to 7 carbon atoms and is substituted by a terminal hydroxy, alkoxy, amino, alkylamino, dialkylamino, pyrrolidino, piperidino or hexamethyleneimino group:

reaction of a compound of the formula

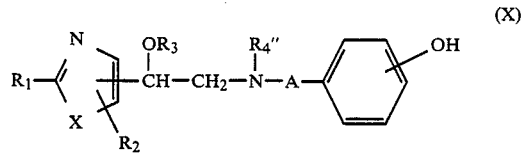

(X)

(in which

A, X and $R_1$ to $R_3$ are as hereinbefore defined and
$R_4''$ has the meanings mentioned hereinbefore for $R_4$ or represents a readily eliminatable protecting group for an amino group) with a compound of the formula $$Z_4-R_8 \quad \text{(XI)}$$

(in which $R_8$ represents an alkyl group with 1 to 3 carbon atoms, an alkyl group which has 1 to 6 carbons and is substituted by a terminal carboxyl, alkoxy-carbonyl, aminocarbonyl, alkylaminocarbonyl or dialkylaminocarbonyl group, or an alkoxy group which has 2 to 7 carbon atoms and is substituted by a terminal hydroxyl, alkoxy, amino, alkylamino, dialkylamino, pyrrolidino, piperidino or hexamethyleneimino group, and $Z_4$ represents a nucleophilic leaving group such as a halogen atom or a sulphonyloxy group, for example a chlorine, bromine or iodine atom, the methanesulphonyloxy, p-toluenesulphonyloxy or ethoxysulphonyloxy group, or $Z_4$ together with a β-hydrogen atom of the radical $R_8$ represents an oxygen atom) and, where appropriate, subsequent elimination of a protecting group which has been used.

Examples of suitable protecting groups, which can be readily eliminated, for the central nitrogen atom ($R_4''$) are the acetyl, benzoyl, tert.butoxycarbonyl, benzyloxycarbonyl, ethoxycarbonyl or benzyl groups.

The reaction is expediently carried out in a solvent such as diethyl ether, tetrahydrofuran, dioxane, methanol, ethanol or dimethylformamide, and preferably in the presence of an acid-binding agent such as sodium hydroxide or potassium tert.butylate; but preferably in the presence of potassium carbonate or sodium hydride, or pyridine, it also being possible for an organic base such as pyridine to serve as solvent, or for the preparation of 2-hydroxyethoxy compounds of the general formula I with ethylene oxide, at temperatures of between 0° and 100° C., but preferably at temperatures of between 20° and 80° C.

The subsequent elimination, where appropriate, of a protecting group which has been used is preferably effected by hydrolysis in an aqueous solvent, for example in water, isopropanol/water, tetrahydrofuran/water or dioxane/water, in the presence of an acid such as hydrochloric acid or sulphuric acid, or in the presence of an alkali metal base such as sodium hydroxide or potassium hydroxide, at temperatures of between 0° and 100° C., preferably at the boiling point of the reaction mixture. However, the elimination of a benzyl or benzyloxycarbonyl radical is preferably effected by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures of between 0° and 50° C., but preferably at room temperature, and under a hydrogen pressure of 1 to 7 bar, but preferably of 3 to 5 bar.

(g) For the preparation of compounds of the general formula I in which $R_3$ represents a hydrogen atom: reduction of a compound of the general formula

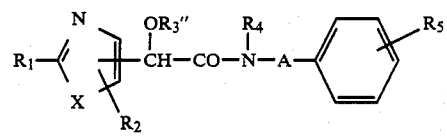

(XII)

in which
A, X, $R_1$, $R_2$ and $R_4$ are as hereinbefore defined, and
$R_3''$ denotes a hydrogen atom or an alkyl group.

The reduction is carried out in a suitable solvent such as diethyl ether or tetrahydrofuran, with a reducing agent such as a metal hydride, for example with lithium aluminum hydride, diborane or diborane/dimethyl sulphide, but preferably with sodium borohydride in the presence of glacial acetic acid or trifluoroacetic acid, at temperatures of between 0° and 50° C., but preferably at temperatures of between 10° and 25° C. During the reduction a carbonyl group which is optionally present in the radicals $R_4$ and $R_5$ can at the same time also be reduced to a methylene group. Furthermore, a cyano group present in the radical $R_4$ can also be reduced to an aminomethylene group.

(h) For the preparation of compounds of formula I in which $R_5$ represents or contains an alkoxycarbonyl, aminocarbonyl, alkylaminocarbonyl, or dialkylaminocarbonyl group:
reaction of a compound of the formula

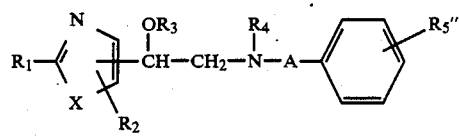

(XIII)

(in which
$R_1$ to $R_4$, A and X are as hereinbefore defined, and
$R_5'''$ represents a carboxyl group or an alkoxy group which has 1 to 6 carbon atoms and is substituted by a terminal carboxyl group) or of its reactive derivatives such as, for example, its esters, with a compound of the formula $$H-R_9 \quad \text{(XIV)}$$

in which
$R_9$ represents an alkoxy, amino, alkylamino or dialkylamino group, it being possible, however, for each alkyl or alkoxy moiety to contain 1 to 3 carbon atoms.

The esterification or amidation is expediently carried out in a solvent such as methylene chloride, chloroform, carbon tetrachloride, ether, tetrahydrofuran, dioxane, benzene, toluene, acetonitrile or dimethylformamide, but particularly advantageously in an excess of a compound of formula XIV which is used, for example in methanol, ethanol, n-propanol, isopropanol, ammonia, methylamine, ethylamine, dimethylamine or diethylamine, where appropriate in the presence of an acid activating agent or of a water-abstracting agent, for example in the presence of ethyl chloroformate, thionyl chloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, or of an agent activating the amino group, for example phosphorus trichloride and, where appropriate, in the presence of an inorganic base such as sodium carbonate or a tertiary organic base such a triethylamine or pyridine, which can at the same time serve as solvents, at temperatures between −25° C. and 250° C., but preferably at temperatures of −10° C. and the boiling point of the solvent used.

(j) For the preparation of compounds of formula I in which R₄ represents an alkyl group which is optionally substituted by a phenyl, carboxyl, alkoxycarbonyl or cyano group or, in the 2- or 3-position, by a hydroxyl group, or represents an alkenyl group:

reaction of a compound of the formula

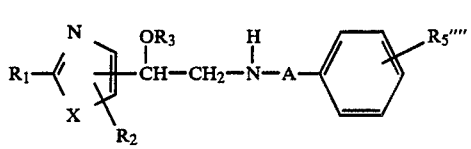
(XV)

(in which
A, X and R₁ to R₃ are as hereinbefore defined, and
R₅'''' has the meanings hereinbefore mentioned for R₅ but it being possible, where necessary, for an amino or alkylamino group contained in the radical R₅ to be protected by a protecting group) with a compound of the general formula $$Z_5-R_4'''$$ (XVI)

(in which
R₄''' has, with the exception of the hydrogen atom, the meanings mentioned hereinbefore for R₄, and Z₅ denotes a nucleophilic leaving group such as a halogen atom or a sulphonyloxy group, for example a chlorine, bromine or iodine atom, the methanesulphonyloxy, p-toluenesulphonyloxy or ethoxysulphonyloxy group, or
Z₅ together with an α or β hydrogen atom of the alkyl radical R₄''' denotes an oxygen atom) and, where appropriate, subsequent elimination of a protecting group which has been used.

The alkylation is carried out in a suitable solvent such as methanol, ethanol, diethyl ether, acetone, methylene chloride, tetrahydrofuran, dioxane, dimethylformamide or dimethyl sulphoxide, where appropriate in the presence of a base such as sodium carbonate, potassium tertbutylate, triethylamine or pyridine, it also being possible, however, for the two latter also at the same time to serve as solvents, with a suitable alkylating agent such as methyl iodide, dimethyl sulphate, ethyl bromide, diethyl sulphate, benzyl chloride, n-propyl bromide, isopropyl bromide, allyl bromide, ethylene oxide, 2-hydroxy-ethyl bromide, 2-cyano-ethyl bromide or formaldehyde/formic acid, or in the presence of sodium cyanoborohydride if an appropriate carbonyl compound is used, at temperatures between 0° and 100° C.

The subsequent elimination, where appropriate, of a protecting group which has been used is preferably carried out by hydrolysis in an aqueous solvent, for example in water, isopropanol/water, tetrahydrofuran/water or dioxane/water, in the presence of an acid such as hydrochloric acid or sulphuric acid, or in the presence of an alkali metal base such as sodium hydroxide or potassium hydroxide, at temperatures between 0° and 100° C., preferably at the boiling point of the reaction mixture. The elimination of a benzyl or benzyloxycarbonyl radical is, however, preferably effected by hydrogenolysis, for example with hydrogen in the presence of a catalyst such as palladium/charcoal in a solvent such as methanol, ethanol, ethyl acetate or glacial acetic acid, where appropriate with the addition of an acid such as hydrochloric acid, at temperatures between 0° and 50° C., but preferably at room temperature, and under a hydrogen pressure of 1 to 7 bar, but preferably 3 to 5 bar.

(k) For the preparation of compounds of formula I in which R₃ and R₄ together represent an ethylene group:

reduction of a compound, which is optionally formed in the reaction mixture, of the formula

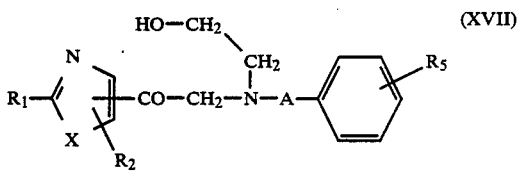
(XVII)

in which
A, X, R₁, R₂ and R₅ are as hereinbefore defined, or of its cyclic hemiacetal.

The reaction is preferably carried out in a solvent such as methylene chloride, chloroform or trifluoroacetic acid with a suitable hydride such as a complex metal hydride, for example with sodium borohydride, with catalytically activated hydrogen, for example with hydrogen in the presence of platinum, or with a trialkylsilane, for example with triethylsilane, where appropriate in the presence of an acid such as boron trifluoride, for example in the presence of boron trifluoride etherate, at temperatures between 0° and 60° C., but preferably in trifluoroacetic acid as solvent and at room temperature.

(l) For the preparation of compounds of formula I in which R₃ and R₄ together denote an ethylene group in which the methylene group adjacent to the N or O atom has been replaced by a carbonyl group: reaction of a compound of the formula

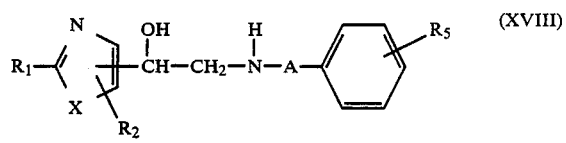
(XVIII)

in which
A, X, R₁, R₂ and R₅ are as hereinbefore defined, with a haloacetyl halide or haloacetic acid.

The reaction is expediently carried out in a solvent such as methylene chloride, tetrahydrofuran, dioxane, benzene or toluene, or in an excess of the acylating agent which is used, where appropriate in the presence of an acid-binding agent such as potassium carbonate, an alkali metal hydride such as sodium hydride or in the presence of a tertiary organic base such as triethylamine or pyridine, it also being possible for the two latter at the same time to serve as solvents, at temperatures between 0° and 100° C., but preferably at temperatures of between room temperature and the boiling point of the reaction mixture. When a haloacetic acid ester in the presence of potassium carbonate is used for the reaction, a corresponding lactone is preferentially obtained.

(m) For the preparation of compounds of formula I in which $R_3$ and $R_4$ together denote an ethylene group: reduction of a compound of the formula

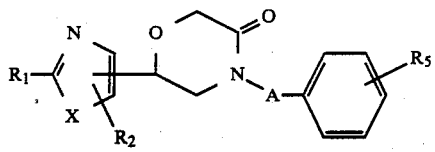 (XIX)

in which

A, X, $R_1$, $R_2$ and $R_5$ are as hereinbefore defined,

The reduction is carried out in a suitable solvent such as diethyl ether or tetrahydrofuran with a reducing agent such as a metal hydride, for example with lithium aluminium hydride or sodium borohydride in the presence of glacial acetic acid or trifluoroacetic acid, but preferably with phosphorus oxychloride/sodium borohydride, diborane or diborane/dimethyl sulphide, at temperatures of between 0° and 50° C., but preferably at temperatures of between 10° and 25° C. During the reduction a carbonyl group which is optionally present in the radical $R_5$ can also at the same time be reduced to a methylene group.

(n) For the preparation of compounds of formula I in which $R_3$ and $R_4$ together represent an ethylene group in which the methylene group adjacent to the O atom has been replaced by a carbonyl group: cyclisation of a compound, which is optionally formed in the reaction mixture, of the formula

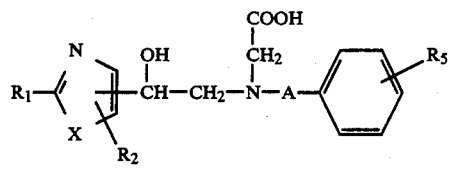 (XX)

in which

A, X, $R_1$, $R_2$ and $R_5$ are as hereinbefore defined, or of its reactive derivative such as its esters or halides.

The cyclisation is carried out in a suitable solvent such as methylene chloride, chloroform, benzene, toluene, tetrahydrofuran, acetone, methyl ethyl ketone or dioxane, where appropriate in the presence of a water-abstracting agent such as thionyl chloride, phosphorus trichloride, N,N'-dicyclohexylcarbodiimide, N,N'-carbonyl diimidazole or N,N'-thionyldiimidazole, at temperatures of between 0° and 100° C., but preferably at the boiling point of the reaction mixture.

(o) For the preparation of compounds of formula I in which $R_1$ represents a hydrogen or halogen atom, a trifluoromethyl or alkyl group, and $R_3$ represents a hydrogen atom:

reaction of a compound of the formula

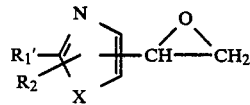 (XXI)

(in which

X and $R_2$ are as hereinbefore defined, and $R_1'$ represents a hydrogen or halogen atom, a trifluoromethyl or alkyl group) with an amine of the formula

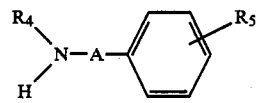 (XXII)

in which

A, $R_4$ and $R_5$ are as hereinbefore defined,

The reaction is carried out in a suitable solvent, for example in a polar solvent such as ethanol or isopropanol or in an aprotic solvent such as dimethylformamide or dimethyl sulphoxide, at temperatures between 0° and 150° C., but preferably at temperatures between 50° and 100° C.

When there is obtained, according to the invention, a compound of formula I in which $R_5$ represents or contains an alkoxycarbonyl, aminocarbonyl, alkylaminocarbonyl or dialkylaminocarbonyl group and/or $R_1$ represents an amino group which is substituted by an alkanoyl or benzoyl group, this can, by hydrolysis, be converted into a corresponding compound of formula I in which $R_5$ represents or contains a carboxyl group and/or $R_1$ represents an amino group, or a compound of formula I in which $R_5$ represents an alkoxy group which is substituted by a carboxyl, alkoxycarbonyl, aminocarbonyl, alkylaminocarbonyl or dialkylaminocarbonyl group, this can, by reduction with a suitable metal hydride, be converted into a compound of formula I in which the above-mentioned substituted alkoxy radical contains a methylene group in place of the carbonyl group, or a compound of formula I in which $R_3$ represents an alkyl group and/or $R_5$ represents one of the alkoxy groups mentioned hereinbefore, this can, by ether cleavage, be converted into a corresponding compound of formula I in which $R_3$ represents a hydrogen atom and/or $R_5$ represents a hydroxyl group or an alkoxy group which is substituted by a hydroxyl group.

The subsequent hydrolysis is carried out either in the presence of an acid such as hydrochloric acid, sulphuric acid, phosphoric acid or trichloroacetic acid, or in the presence of a base such as sodium hydroxide or potassium hydroxide, in a suitable solvent such as water, methanol, ethanol, ethanol/water, water/isopropanol or water/dioxane, at temperatures of $-10°$ C. and 120° C., for example at temperatures between room temperature and the boiling point of the reaction mixture.

The subsequent reduction is carried out in a suitable solvent such as diethyl ether or tetrahydrofuran with a suitable metal hydride, for example with lithium aluminium hydride, diborane or diborane/dimethyl sulphide, but preferably with sodium borohydride in the presence of glacial acetic acid or trifluoroacetic acid, at temperatures of between 0° and 50° C., but preferably at temperatures between 10° and 25° C.

The subsequent ether cleavage is carried out in the presence of an acid such as hydrogen chloride, hydrogen bromide, sulphuric acid or boron tribromide in a suitable solvent such as methanol, ethanol, water/isopropanol, methylene chloride, chloroform or carbon tetrachloride, at temperatures between $-30°$ C. and the boiling point of the reaction mixture.

It is possible during the subsequent hydrolysis, reduction or ether cleavage for compounds of formula I in which $R_3$ and $R_4$ together denote an ethylene group in which the methylene group adjacent to the O atom has been replaced by a carbonyl group to be simultaneously cleaved.

As already mentioned the new compounds can exist in the form of their enantiomers, enantiomer mixtures or racemates, or, where they contain at least two asymmetric carbon atoms, in the form of their diastereomers or diastereomer mixtures.

Thus, the compounds of formula I which have been obtained and which contain only one optically active centre can be separated into their optical antipodes by methods known per se (see Allinger N. L. and Eliel E. L. in "Topics in Stereochemistry", Vol. 6, Wiley Interscience, 1971) as, for example by recrystallisation from an optically active solvent or by reaction with an opticaly active substance, in particular acids, which forms salts with the racemic compound, and separation of the mixture of salts obtained in this manner, for example on the basis of different solubilities, into the diastereomeric salts, from which the free antipodes can be liberated by the action of suitable agents Examples of particularly useful optically active acids are the D-and L-forms of tartaric acid, di-O-toluyl tartaric acid, malic acid, mandelic acid, camphorsulphonic acid, glutamic acid, aspartic acid or quinic acid.

Furthermore, the compounds of formula I which have been obtained and have at least 2 asymmetric carbon atoms can be separated into their diastereomers on the basis of their physcal chemical differences by methods known per se. for example by chromatography and/or fractional crystallisation. A pair of enantiomers which has been obtained in this way can be separated into its optical isomers as described above. If, for example, a compound of formula I contains two optically active carbon atoms then the corresponding (R R', S S') and (R S', S R') forms are obtained.

The compounds used as starting materials, which, of course, can also be used in their optically pure forms, are obtained by processes knonn from the literature (see "Thiazole and its Derivatives" in Heterocyclic Compounds, Vol. 34, and Advances in Heterocyclic Chemistry, Vol. 17, page 100 (1974)) or are themselves known from the literature. Some of them are present only in the reaction mixture, and thus some of them cannot be isolated.

The compounds which are used as starting materials, of formula II in which $Z_1$ represents a nucleophilic leaving group, are obtained by reduction of a corresponding acetyl compound, for exampe with a complex metal hydride and, where appropriate, subsequent alkylation.

A compound of formula IV which need not be isolated is obtained by reaction of a compound of the general formula

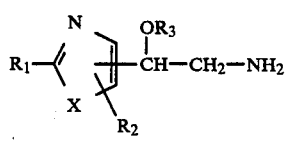 (XXIII)

with a carbonyl compound of the formula

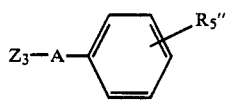 (V)

or by reaction of an amine of the formula

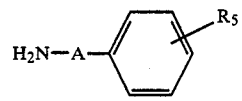 (XXIV)

with a glyoxal of the formula

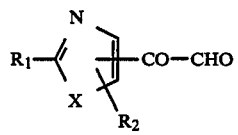 (XXV)

(in which
$R_1$ to $R_3$, $R_5$, A and X are as hereinbefore defined
$R_5''$ has the meanings mentioned hereinbefore for $R_5$ whilst an amino or alkylamino group contained in the radical $R_5$ may be protected by a protecting group, and
$Z_3$ together with one hydrogen atom on the adjacent carbon atom of the radical A represents an oxygen atom) in the presence of sodium cyanoborohydride in a suitable solvent such as methylene chloride, chloroform, dioxan, benzene or toluene and, where appropriate, in the presence of a water-abstracting agent such as p-toluenesulphonic acid or a molecular sieve, at temperatures between 0° C. and the boiling point of the solvent used, but preferably in benzene or toluene by azeotropic distillation of the reaction mixture.

A compound which is necessary for the preparation of these starting compou.dns having the formula

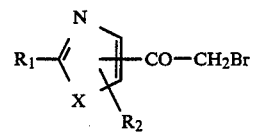 (XXVI)

(in which
$R_1$, $R_2$ and X are as hereinbefore defined is obtained by bromination of the corresponding acetyl compounds in glacial acetic acid or hydrogen bromide/glacial acetic acid at temperatures between 20° and 100° C., or, where R in the 5-position represents a hydrogen atom, and X represents a sulphur atom, by ring closure of the corresponding thioamides with dibromodiacetyl in a solvent such as diethyl ether or acetonitrile. Furthermore, for example the abovementioned acetyl compounds are obtained, when $R_2$ in the 4-position represents a methyl group and X represents a sulphur atom, by reaction of a corresponding thioamide with 3-chloroacetoacetone in water, ethanol, water/ethanol or in a melt (see Z. Chem. 9, 187 (1969)) or, when $R_2$ in the 5-position represents a methyl group and X represents an oxygen or sulphur atom, by reaction of a corresponding acylaminoacetoacetone with dehydrating agents (see Chem. Ber. 84, 96 (1951) and Chem. Ber. 93, 1998 (1960)) or with phosphorus pentasulphide or with 2,4-bis(4-methoxyphenyl)-1,3-dithia-2,4-diphosphetan-2,4-disulphide.

An amino-ketone of formula VII is obtained in the reaction mixture by reaction of corresponding bromoacetyl derivative with an appropriate amine or with urotropine, followed by hydrolysis.

The compounds which are used as starting materials having the formulae VIII, X, XIII, XV and XX are expediently obtained by alkylation of an appropriate amine.

The compounds which are used as starting materials and have the formula XII are obtained by acylation of an appropriate amine.

A compound which is used as starting material and has the formula XXI is obtained for example by reaction of an appropriate bromohydrin with aqueous potassium hydroxide solution or by reaction of an appropriate aldehyde with dimethylsulphonium methylide at 0° C. in dimethyl sulphoxide/tetrahydrofuran.

A corresponding glyoxal is obtained, for example, by reaction of an appropriate bromoacetyl compound of formula XXVI with dimethyl sulphoxide at room temperature.

Furthermore, the compounds of formula I which have been obtained can be converted into their acid addition salts, in particular for pharmaceutical use into their physiologically acceptable salts, with inorganic or organic acids. Examples of suitable acids for this purpose are hydrochloric acid, hydrobromic acid, sulphuric acid, phosphoric acid, fumaric acid, succinic acid, lactic acid, citric acid, tartaric acid or maleic acid.

As already mentioned above, the new compounds of formula I in which $R_3$ and $R_4$ together denote an ethylene group in which the methylene group attached to the N atom is replaced by a carbonyl group (see Formula XIX) represent valuable intermediates for the preparation of the morpholines of formula I.

The other new compounds of formula I (excepting the lactams), their enantiomers, enantiomer mixtures or racemates, or, where they contain at least 2 asymmetric carbon atoms, their diastereomers or diastereomer mixtures, and their acid addition salts, in particular for pharmaceutical use their physiologically acceptable acid addition salts, have valuable pharmacological properties, besides an inhibition effect on platelet aggregation, in particular an action on the metabolism, preferentially a blood sugar lowering and body fat reducing action. The present invention thus provides pharmaceutical compositions comprising an effective blood sugar lowering amount, or an effective antiadipose amount, of a compound of Formula I, other than the lactams thereof, in combination with a nontoxic, pharmaceutically acceptable carrier.

In addition, some of the above-mentioned compounds also have an anabolic action as well as causing a reduction in the levels of atherogenic β-lipoproteins VLDL and LDL. In this connection, where $R_1$ represents a trifluoromethyl group, the diastereomer which has proved to be particularly preferred is the one whose proton in the 5-position of the thiazole ring is located at lower field in the $CDCl_3/CD_3OD$-NMR spectrum in the morpholine series and in the $CDCl_3$-NMR spectrum in the ethanolamine series.

The following compounds, for example, have been investigated for their biological properties, as follows:

A = N-[2-(4-Carbomethoxyphenyl)-1-methylethyl]-2-hydroxy-2-(2-trifluoromethyl-thiazol-4-yl)ethanamine, B = N-[2-(4-Carbomethoxymethoxyphenyl)-1-methylethyl]-2-hydroxy-2-(2-trifluoromethyl-thiazol-4-yl)ethanamine, C = N-[2-(4-Aminocarbonylmethoxyphenyl)-1-methylethyl]-2-hydroxy-2-(2-trifluoromethyl-thiazol-4-yl)ethanamine, D = N-[2-(4-Methylaminocarbonylmethoxyphenyl)-1-methylethyl]-2-hydroxy-2-(2-trifluoromethylthiazol-4-yl)ethanamine, E = N-[2-(4-Carboxyphenyl)-1-methylethyl]-2-hydroxy-2-(2-trifluoromethyl-thiazol-4-yl)ethanamine, F = N-[2-(4-Carbomethoxymethoxyphenyl)-1-methylethyl]-2-(2-trifluoromethyl-thiazol-4-yl)morpholine, G = Methyl 3-[2-(4-carbomethoxyphenyl)-1-methylethyl]-5-(2-trifluoromethyl-thiazol-4-yl)-2-oxazolidine carboxylate (diastereomer pairs A and B), H = Methyl 3-[2-(4-carbomethoxyphenyl)-1-methylethyl]-5-(2-trifluoromethyl-thiazol-4-yl)-2-oxazolidine carboxylate (diastereomer pairs C and D), I = Methyl 3-[2-(4-carbomethoxymethoxyphenyl)-1-methylethyl]-5-(2-trifluoromethyl-thiazol-4-yl)-2-oxazolidine carboxylate (diastereomer pairs A and B).

J = Methyl 3-[2-(4-carbomethoxymethoxyphenyl)-1-methylethyl]-5-(2-trifluoromethyl-thiazol-4-yl)-2-oxazolidine carboxylate (diastereomer pairs C and D), K = N-[2-(4-Carbomethoxymethoxyphenyl)-1-methylethyl]-N-methyl-2-hydroxy-2-(2-trifluoromethyl-thiazol-4-yl)ethanamine, L = N-[2-(4-Aminocarbonylmethoxyphenyl)-1-methylethyl]-2-hydroxy-2-(2-methyl-thiazol-4-yl)ethanamine, M = N-[2-(4-Carbomethoxymethoxyphenyl)-1-methylethyl]-2-hydroxy-2-(2-methyl-thiazol-4-yl)ethanamine, N = N-[2-(4-Carbomethoxymethoxyphenyl)-1-methylethyl]-2-hydroxy-2-(thiazol-4-yl)ethanamine, O = N-[2-(4-Carboxymethoxyphenyl)-1-methylethyl]-2-(2-trifluoromethyl-thiazol-4-yl)morpholine, P = N-[2-(4-Carbomethoxymethoxyphenyl)-1-methylethyl]-2-hydroxy-2-(2-chloro-thiazol-4-yl)ethanamine, Q = N-[2-(4-(Hydroxyethoxy)phenyl)-1-methylethyl]-2-hydroxy-2-(2-trifluoromethyl-thiazol-4-yl)ethanamine and R = Methyl 3-[2-(4-(2-carbomethoxy-1-methylethenyl)-phenyl)-1-methylethyl]-5-(2-trifluoromethyl-thiazol-4-yl)-2-oxazolidine carboxylate 1. Antidiabetic action:

The antidiabetic action of the compounds according to the invention can be measured as a blood sugar lowering action in experimental animals. For this purpose, the substances for investigation were suspended in 1.5% methyl cellulose and administered by gavage to female mice of our own breed. 30 minutes later 1 g of glucose per kg of body weight was dissolved in water and administered subcutaneously. A further 30 minutes later blood was taken from the retroorbital venus plexus. Glucose in the serum was determined by the hexokinase method using an analytical photometer.

The Table which follows lists the lowerings of blood sugar, as a % of a parallel control group, observed in this design of experiment. Statistical analysis employed Student's t-test with $p=0.05$ as significance limit.

| Compound | % change from figure for the control group Dose [mg/kg] | | | | |
| --- | --- | --- | --- | --- | --- |
|  | 0.3 | 1 | 3 | 10 | 30 |
| A |  | −40 |  |  | −63 |
| B |  | −64 |  | −73 |  |

-continued

| Compound | % change from figure for the control group Dose [mg/kg] | | | | |
|---|---|---|---|---|---|
| | 0.3 | 1 | 3 | 10 | 30 |
| C | | | −68 | | −76 |
| D | | −65 | | | −68 |
| E | | | −57 | | −70 |
| F | | | −61 | −64 | |
| G | | | −56 | | |
| H | | | −59 | | |
| I | | −68 | | −72 | |
| J | −36 | | | −60 | |
| K | | −42 | | | −60 |
| L | | | −61 | | |
| M | | −32 | | −58 | |
| N | | | −23 | | |
| O | | | −60 | | |
| P | −52 | | | | |
| Q | | −70 | | | |
| R | | | −56 | | |

2. Antiadipose action:

The antiadipose action of the compounds according to the invention was demonstrated using two experimental procedures:

(a) In the first experimental procedure, the increase in lipolysis was measured by the rise in serum glycerol. The experimental procedure is identical to the experimental procedure described above for testing the blood sugar lowering action. Glycerol was determined in a combined enzymatic/colorimetric assay using an analytical photometer. The results are listed in the Table which follows, as a % of a parallel control.

| Compound | % change from figure for the control group Dose [mg/kg] | | | | |
|---|---|---|---|---|---|
| | 0.3 | 1 | 3 | 10 | 30 |
| A | | | 88 | | |
| B | | 312 | | 326 | |
| C | | | 504 | | 732 |
| D | | 433 | | | 439 |
| E | | | 226 | | 305 |
| F | | | 413 | 430 | |
| G | | | 209 | | |
| H | | | 168 | | |
| I | | 204 | | 228 | |
| J | 260 | | | 391 | |
| K | | 283 | | | 416 |
| L | | | 220 | | |
| M | | 307 | | 453 | |
| N | | | (8) | | |
| O | | | 336 | | |
| P | 217 | | | | |
| Q | | 221 | | | |
| R | | | 758 | | |

( ) = not significant (p > 0.05)

(b) In the second experimental procedure to detect an antiadipose action of the compounds according to the invention, the reduction in adipose tissue was measured by monitoring the ovarian adipose tissue. For this purpose, the compounds were administered by gavage in a suspension of 1.5% methyl cellulose once a day to mice. On the fifth day, the ovarian adipose tissue was dissected out and weighed. The Table which follows shows the results as a % of a parallel control group.

| Compound | % change from figure for the control group Dose: 10 [mg/kg] |
|---|---|
| A | −36 |
| B | −60 |
| C | −35 |
| D | −30 |
| F | −47 |
| G | −33 |
| H | −20 |
| I | −28 |
| J | −11 |
| K | −12 |
| L | −53 |
| M | −48 |

3. Cardiac side effects:

It was possible to rule out the occurrence of undesired side effects on the heart by the compounds according to the invention in the dose range having metabolic activity and intended for therapy. The demonstration entailed measurement of the heart rate of mice during the testing of the blood sugar lowering action (see above). One hour after the oral administration of the compounds the heart rate was determined by a ECG-triggered tachograph. The Table which follows shows the change in the heart rate as a percentage of the control group.

| Compound | % change from figure for the control group Dosage [mg/kg] | | |
|---|---|---|---|
| | 0.3 | 1 | 3 |
| A | | (21) | |
| B | | (0) | |
| C | | | (11) |
| D | | 17 | |
| E | | | 17 |
| F | | | (9) |
| I | | (3) | |
| J | (0) | | |
| K | | (−4) | |
| M | | (−1) | |
| O | | | (7) |

( ) = not significant (p > 0.05)

Furthermore, in the investigations which are described above, no toxic side effects were observed for the substances according to the invention at the doses administered. Hence they are well tolerated.

Thus, on the basis of their pharmacological properties, the new compounds of formula I (other than the lactams) and their optical isomers, diastereomers and physiologically acceptable acid addition salts with inorganic or organic acids, are suitable for the treatment both of diabetes mellitus and of obesity, and thus in particular for the treatment of the obese diabetic. In addition, said compounds may be used for the prophylaxis and the treatment of atherosclerotic changes in blood vessels which occur particularly frequently in the case of those suffering from diabetes and/or obesity. In this connection, it is possible entirely to suit the requisite dose to the metabolic/physiological requirements of the individual patient, since the compounds have no cardiovascular action over a wide dose range. Thus, the daily dose for adults is between 1 and 3000 mg, but preferably 1 to 1000 mg, distributed over 1 to 4 doses per day. For this purpose, the above-mentioned compounds, with or without other active substances, can be incorporated into the customary pharmaceutical unit dosage forms such as powders, tablets, coated tablets, capsules, suppositories or suspensions.

Furthermore, the above-mentioned compounds can be used for the treatment of obese animals such as dogs, and, as a consequence of their action reducing body fat (lypolysis), can be used to reduce undesired fatty deposits in fatstock rearing, that is to say to improve the quality of meat from fatstock such as pigs, cattle, sheep and poultry. The administration of the above-mentioned compounds to the animals can be affected orally or non-orally, for example as a feed supplement or by injection or by implanted minipumps. The daily dose for this purpose is between 0.01 and 100 mg/kg, but preferably between 0.1 and 10 mg/kg of body weight.

The present invention thus provides a method of treating an individual afflicted with diabetes mellitus which comprises administering to said individual an effective blood sugar lowering amount of a compound of Formula I (other than the lactams). The invention also provides a method of treating an individual afflicted with obesity, or an animal, which comprises administering to same an effective antiadipose amount of said compound.

The Examples which follow are intended to illustrate the invention in detail:

EXAMPLE A

2-Trifluoromethyl-4-bromoacetylthiazole 9.2 g (0.071 mol) of Trifluoromethylthioacetamide, dissolved in 200 ml of acetonitrile, are added dropwise in 2.5 hours to a boiling solution of 17.4 g (0.071 mol) of dibromodiacetyl in 200 ml of acetonitrile. The solvent is removed by distillation, and the remaining product is extracted with cyclohexane. The extract is concentrated, and the remaining oily residue is purified on a silica gel column using toluene/cyclohexane as eluant.
Yield: 8.2 g (42.7% of theory),
M.p.: 36°–37° C.

EXAMPLE B 2,4-Dimethyl-5-acetyl-thiazole

A mixture of 34 g (0.25 mol) of 3-chloroacetoacetone and 19 g (0.25 mol) of thioacetamide is slowly heated, with stirring. An exothermic reaction starts at about 60° C. The heating bath is removed, and the product is then stirred for 1 hour and allowed to cool during this. The precipitated hydrobromide is triturated with petroleum ether/ethanol=5/1 and filtered off with suction. For the conversion into the free base, the salt is dissolved in water and made alkaline with sodium bicarbonate. The mixture is then extracted several times with methylene chloride, the organic phase is dried over sodium sulphate and concentrated, and the residue is purified on a silica gel column using toluene as eluant.
Yield: 19.7 g (51% of theory)
$^1$H-NMR spectrum (CDCl$_3$): δ=2.50 ppm (s, CH$_3$)

EXAMPLE C 2,4-Dimethyl-5-bromoacetyl-thiazole

A solution of 20.8 g (0.13 mol) of bromine in 50 ml of glacial acetic acid is slowly added dropwise to a solution of 20.2 g (0.13 mol) of 2,4-dimethyl-5-acetyl-thiazole in glacial acetic acid, heated to reflux. After 1 hour, the mixture is evaporated to dryness, the residue is dissolved in water, and the solution is neutralised with sodium carbonate solution. The mixture is then extracted several times with methylene chloride, and the organic phase is dried and concentrated. The oil which was obtained in this way was used for further reactions without further purification.
Yield: 24 g (79% of theory).

EXAMPLE D 2-phenyl-4-formyl-thiazole-cyanohydrin 16.4 g (0.0607 mol) of 2-phenyl-4-formyl-thiazolhydrobromide in 230 ml of water and 150 ml of dioxan are heated to 30° C. on a steam bath, during which about 80-90% of the substance dissolves. The mixture is then cooled to 20° C. in an ice bath and, while stirring vigorously, 22 g (0.162 mol) of potassium dihydrogen phosphate are added in portions. Then 6.1 g (0.124 mol) of sodium cyanide is introduced in portions, and the mixture is stirred at room temperature for 1.5 hours. The precipitated product is extracted with ether, the organic phase is dried over sodium sulphate and concentrated, and the residue is dried in vacuo.
Yield: 13 g (100% of theory),
M.p.: 140°–141° C.
Calculated: C 62.20; H 3.72; N 12.95; S 14.82. Found: C 62.35; H 3.91; N 12.89; S 14.93.

EXAMPLE E 2-(2-Trifluoromethyl-thiazol-4-yl)glyoxal 3 g (0.011 mol) of 2-Trifluoromethyl-4-bromoacetyl-thiazole are dissolved in 30 ml of dimethyl sulphoxide and the solution is maintained at room temperature for 70 hours. It is then poured onto 100 g of ice, and the mixture is extracted several times with ether, the organic phase is dried over sodium sulphate and concentrated, and the residue is purified on a silica gel column using toluene/ethyl acetate=7/3 as eluant.
Yield: 1.3 g (56% of theory).

EXAMPLE F

2-Trifluoromethyl-5-methyl-4-bromoacetyl-oxazole (a) 3-Trifluoroacetamino-acetoacetone 10 g (0.0662 mol) of 3-Amino-acetoacetone hydrochloride are cautiously mixed with 56 g (0.266 mol) of trifluoroacetic anhydride. The reaction mixture foams vigorously and then a clear solution forms. The mixture is boiled under reflux for 30 minutes, and then the solvent is removed, the residue is taken up in 500 ml of ether, and the solution is shaken three times with 100 ml of saturated sodium bicarbonate solution each time. The ether phase is dried over sodium sulphate and concentrated.
Yield: 12 g (86% of theory),
M.p.: 44°–46° C.
Calculated: C 39.81; H 3.81; N 6.63. Found: C 39.80; H 3.67; N 6.87.

(b) 2-Trifluoromethyl-5-methyl-4-acetyl-oxazole 5 g (0.0237 mol) of 3-Trifluoroacetaminoacetoacetone are heated with 5 ml of trifluoroacetic anhydride on a steam bath for 4 hours. During this the solution changes colour and the trifluoroacetic anhydride almost completely evaporates. The residue is dissolved in 100 ml of chloroform, and the solutio is shaken three times with 50 ml of saturated sodium bicarbonate solution each time. The chloroform phase is dried over sodium sulphate and evaporated.

Yield: 3.2 g (70% of theory),
$^1$H-NMR spectrum (CDCl$_3$): δ=2.52 ppm (s, CH$_3$); 2.65 ppm (s, CH$_3$).

(c) 2-Trifluoromethyl-5-methyl-4-bromoacetyl-oxazole 3.8 g (0.02 mol) of 2-Trifluoromethyl-5-methyl-4-acetyl-oxazole are dissolved in 30 ml of glacial acetic acid, and 3 ml of a 33% strength solution of hydrogen bromide in glacial acetic acid are added. The mixture is heated to 80° C. and, over the course of 1 hour, a solution of 3.2 g (0.02 mol) of bromine in 10 ml of glacial acetic acid is added. After a further 30 minutes the glacial acetic acid is removed. The residue which remains is a dark oil which is reacted further as the crude product.

Yield: 4.4 g (81% of theory), $^1$H-NMR spectrum (CDCl$_3$/CD$_3$OD): δ=2.72 ppm (s, CH$_3$); 4.52 ppm (s, CH$_2$).

EXAMPLE G

2,5-Dimethyl-4-bromoacetyl-oxazole 2.8 g (0.02 mol) of 2,5-Dimethyl-4-acetyl-oxazole are dissolved in 30 ml of glacial acetic acid, and 3 ml of a 35% strength solution of hydrogen bromide in glacial acetic acid are added. The mixture is heated to 100° C. and, over the course of 1 hour, a solution of 3.2 g (0.02 mol) of bromine in 10 ml of glacial acetic acid is added. After a further 2 hours the solvent is removed, and the residue is triturated with 50 ml of ether and filtered off with suction.

Yield: 4.4 g (74% of theory),

M.p.: 175°–176° C.

Calculated: C 28.12; H 3.03; N 4.68; Br 53.45. Found: C 28.29; H 2.93; N 4.78; Br 53.37.

EXAMPLE H

2-Methyl-4-formyl-thiazole-cyanohydrin

Prepared analogously to Example D by reaction of 2-methyl-4-formyl-thiazole with sodium cyanide and potassium dihydrogen phosphate in dimethylformamide/water=1/1. After extraction with ethyl acetate and drying of the extract with sodium sulphate, purification is carried out on a silica gel column using toluene/ethyl acetate=8/2 as eluant.

Yield: 41% of theory,

M.p.: 116°–117° C.

$^1$H-NMR spectra (DMSO/CD$_3$OD): δ=7.580 ppm (s,1H)

EXAMPLE I

4-Formyl-thiazole-cyanohydrin

Prepared analogously to Example D by reaction of 4-formyl-thiazole-hydrobromide with sodium cyanide and potassium dihydrogen phosphate in water. The precipitate which has separated out is filtered off with suction and washed with water. After drying in a vacuum dessicator, almost colourless crystals are obtained and are reacted without further purification.

Yield: 53% of theory,

M.p.: 113°–115° C.

EXAMPLE K

2-Trifluoromethyl-5-methyl-4-bromoacetyl-thiazole (a) 2-Trifluoromethyl-5-methyl-4-acetyl-thiazole 5.8 g (0.0275 mol) of 3-Trifluoroacetaminoacetoacetone are heated at 100° C. with 6.4 g (0.0158 mol) of 2,4-bis-(4-methoxyphenyl)-1,3-dithia-2,4-diphosphetan-2,4-disulphide in 35 ml of absolute toluene, with stirring and under nitrogen, for 10 hours. The resulting clear solution is concentrated, and the residue is purified on a silica gel column using methylene chloride as eluant.

Yield: 3.1 g (54% of theory),

Calculated: C 40.19; H 2.88; N 6.69; S 15.32. Found: C 40.45; H 2.69; N 6.87; S 15.33.

(b) 2-Trifluoromethyl-5-methyl-4-bromoacetyl-thiazole 3 g (0.0144 mol) of 2-Trifluoromethyl-5-methyl-4-acetyl-thiazole are dissolved in 30 ml of glacial acetic acid, and 2.1 ml of a 33% strength solution of hydrogen bromide in glacial acetic acid are added. The mixture is heated to 80° C. and, over the course of 30 minutes, a solution of 2.3 g (0.0144 mol) of bromine in 15 ml of glacial acetic acid is added. After a further 20 minutes, the glacial acetic acid is removed. The residue which remains is a dark oil which is reacted further as the crude product.

Yield: 3.8 g (92% of theory), $^1$H-NMR spectrum (CDCl$_3$/CD$_3$OD): δ=2.90 (s,CH$_3$); 4.70 (s,CH$_2$).

EXAMPLE L

2-Hydroxy-2-(2-propyl-thiazol-4-yl)ethanamine

Prepared analogously to Example P by reduction of 4-(α-cyano-α-hydroxy-methyl)-2-propyl-thiazole (melting point: 68°–70° C.) with sodium borohydride in a mixture of tetrahydrofuran and trifluoroacetic acid. For working up, water is added while cooling, and the mixture is stirred until the precipitate which has formed has dissolved, then the solution is acidified with concentrated hydrochloric acid and heated at 20° C. for 30 minutes and at 100° C. for 60 minutes. After cooling and addition of water, the organic phase is separated off and discarded. The acidic aqueous phase is extracted once more with ethyl acetate, which is discarded. Then, while cooling in ice, the solution is made strongly alkaline with 6N sodium hydroxide solution. Extraction with chloroform several times and drying, filtration and evaporation of the chloroform solution in vacuo are followed by crystallisation from ether of the residue from evaporation.

Yield: 75% of theory,

M.p.: 73°–75° C.

EXAMPLE M

2-Hydroxy-2-(2-isopropyl-thiazol-4-yl)ethanamine

Prepared analogously to Example L by reduction of 4-(α-cyano-α-hydroxymethyl)-2-isopropyl-thiazole (melting point: 56°–58° C.) with sodium borohydride in a mixture of tetrahydrofuran and trifluoroacetic acid.

Yield: 72% of theory,

Melting point: 82°–85° C.

EXAMPLE N

2-Hydroxy-2-(2-trifluoromethyl-thiazol-4-yl)ethanamine 4.6 g (0.033 mol) of Urotropine are added to a solution of 9 g (0.033 mol) of 2-trifluoromethyl-4-bromoacetyl-thiazole in 30 ml of methylene chloride at 10° C., while stirring and cooling. A dense paste of crystals separates out after a few seconds. The mixture is cooled to 0°–3° C. and, after 20 minutes, the precipitate is filtered off with suction and washed with ether. Colourless crystals are obtained after drying at 40° C.

Yield: 11.1 g (81.3% of theory),

M.p.: 134°–137° C.

This urotropine salt is dissolved in 330 ml of ethanol and heated to boiling together with a solution of 70 ml of concentrated hydrochloric acid in 600 ml of water for 2 hours. The mixture is then evaporated to dryness. The solid residue which is thus obtained is dissolved in 300 ml of methanol, cooled to 0° C. and 2.4 g of sodium hydrogen carbonate and, in small portions, 4.2 g of sodium borohydride are successively added. After 2 hours 30 ml of 30% strength sodium hydroxide solution are added, and the mixture is then stirred for 20 minutes. After dilution with 200 ml of water and extraction by shaking several times with methylene chloride, the organic phase is dried over sodium sulphate, and concentrated, and the residue is purified on a silica gel column using methanol as eluant.

Yield: 2.9 g (51% of theory),
$^1$H-NMR spectrum (CDCl$_3$/CD$_3$OD): δ=7.675 ppm (s, 1H).

EXAMPLE O 2-(2-Trifluoromethyl-thiazol-4-yl)morpholine

A solution of 0.9 g (0.036 mol) of 2-(2-trifluoromethyl-thiazol-4-yl)morpholin-5-one in 40 ml of tetrahydrofuran at 3° C. is mixed with 1.35 g (0.036 mol) of sodium borohydride. Then, at 5°-8° C., very slowly and with vigorous stirring 2.43 g (0.036 mol) of glacial acetic acid dissolved in 20 ml of tetrahydrofuran are added dropwise. The cooling is removed after 2 hours, and the mixture is stirred at room temperature for 16 hours. After evaporation to dryness, the resulting residue is mixed with 15 ml of 20% strength hydrochloric acid, and the mixture is heated at 90° C. for 30 minutes. It is then evaporated to dryness, the resulting product is taken up in water, and the solution is made alkaline with sodium carbonate solution. The mixture is then extracted several times with methylene chloride, the organic phase is dried over sodium sulphate and concentrated, and the residue is purified on a silica gel column using ethyl acetate/methanol=8:2 as eluant.

Yield: 0.56 g (65% of theory),
$^1$H-NMR spectrum (CDCl$_3$/CD$_3$OD): δ=4.750 ppm (dd, =C$\underline{H}$—O).

EXAMPLE P

2-Hydroxy-2-(2-phenyl-thiazol-4-yl)ethanamine 34.2 g (0.3 mol) of Trifluoroacetic acid in 60 ml of absolute tetrahydrofuran are added dropwise to a suspension of 11.4 g (0.3 mol) of sodium borohydride in 200 ml of absolute tetrahydrofuran while cooling in ice. Then 13 g (0.06 mol) of 2-phenyl-4-formylthiazolecyanohydrin are introduced in portions, and the mixture is then stirred at room temperature for 20 hours. The solvent is removed, 100 g of ice are cautiously added to the residue, and the mixture is acidified with dilute hydrochloric acid and heated on a steam bath for 1 hour. The mixture is cooled to room temperature, made alkaline with ammonia solution and extracted with chloroform. The extract is dried over sodium sulphate and concentrated and the residue is purified on a silica gel column using methanol as eluant.

Yield: 10.2 g (77.3% of theory),
M.p.: 92°-94° C.
Calculated: C 59.97; H 5.49; N 12.71. Found: C 60.15; H 5.61; N 12.83.

EXAMPLE Q

2-Hydroxy-2-(thiazol-4-yl)ethanamine

Prepared analogously to Example P by reaction of 4-formyl-thiazole with sodium borohydride and trifluoroacetic acid in tetrahydrofuran. The product obtained by extraction with methylene chloride is purified on a silica gel column using methanol as eluant.

Yield: 19% of theory
$^1$H-NMR spectrum (CDCl$_3$/CD$_3$OD): δ=4.880 ppm (dd, =C$\underline{H}$OH)

EXAMPLE R

2-Hydroxy-2-(2-methyl-thiazol-4-yl)ethanamine

Prepared analogously to Example P by reaction of 2-methyl-4-formyl-thiazole with sodium borohydride and trifluoroacetic acid in tetrahydrofuran.

Yield: 63% of theory,
$^1$H-NMR spectrum (CDCl$_3$/CD$_3$OD): δ=7.150 ppm (s, 1H)

EXAMPLE S 2-(2-Trifluoromethyl-thiazol-4-yl)morpholin-5-one 0.3 g (0.0064 mol) of a dispersion of sodium hydride (50–55% in oil) is added in small portions to a stirred solution of 1 g (0.0047 mol) of 2-hydroxy-2-(2-trifluoromethyl-thiazol-4-yl)ethanamine in 15 ml of toluene at 30° C. After 1 hour a solution of 0.55 g (0.0045 mol) of ethyl chloroacetate in 2 ml of toluene is added dropwise. After 2 hours first 1 ml of ethanol and then 4 ml of water are added dropwise. The mixture is then acidified with hydrochloric acid and extracted several times with methylene chloride, and the extract is dried over sodium sulphate. The resulting product is purified on a silica gel column using ethyl acetate/methanol=1/1 as eluant and, after evaporation to dryness, digested with a little ether.

Yield: 0.36 g (32% of theory),
Melting point: 139°-141° C.

EXAMPLE T 2-(2-Methyl-thiazol-4-yl)morpholin-5-one

Prepared analogously to Example S by reaction of 2-hydroxy-2-(2-methyl-thiazol-4-yl)ethanamine with ethyl chloroacetate and purification on a silica gel column using ethyl acetate/methanol=19:1 as eluant.

Yield: 29% of theory,
M.p.: 125°-126° C.
Calculated: C 48.47; H 5.08; N 14.13; S 16.17. Found: C 48.63; H 5.07; N 14.10; S 16.47.

EXAMPLE U 2-(2-Methyl-thiazol-4-yl)morpholine

Prepared analogously to Example O by reduction of 2-(2-methyl-thiazol-4-yl)morpholin-5-one with lithium aluminium hydride and purification of the base on a silica gel column with chloroform/methanol/ammonia=93:7:0.7 as eluant.

Yield: 46% of theory,
Calculated: C 52.15; H 6.56; N 15.20; S 17.40. Found: C 52.37; H 6.52; N 15.27; S 17.32.

EXAMPLE V

2-Hydroxy-2-(2-methyl-thiazol-5-yl)ethanamine (a) 2-Methyl-5-formyl-thiazole-cyanohydrin 0.5 g (0.004 mol) of 2-Methyl-5-formyl-thiazole is dissolved in 3 ml of water and the solution is cooled to 15° C. 1 g of potassium dihydrogen phosphate and 0.4 g of sodium cyanide are successively added. A colourless product precipitates out almost immediately and is stirred at 10° C. for 25 minutes and then filtered off with suction. The resulting crude product is further reacted without further purification.

Yield: 0.5 g (81% of theory).

(b) 2-Hydroxy-2-(2-methyl-thiazol-5-yl)ethanamine

Prepared analogously to Example P by reaction of 2-methyl-5-formyl-thiazole-cyanohydrin in tetrahydrofuran with sodium borohydride and trifluoroacetic acid. The base is purified on a silica gel column using methanol as eluant and is used as the crude product for further reactions.

Yield: 87% of theory.

EXAMPLE W

2-(N,N-Dimethylamino)-4-bromoacetyl-thiazole 133.5 g of Dibromodiacetyl in 2.5 l of ether are boiled under reflux in a soxhlet apparatus with 57 g of N,N-dimethylthiourea for 2.5 days. After the reaction mixture has been cooled and concentrated, the resulting residue is taken up in water, and the solution is neutralised with saturated sodium bicarbonate solution and extracted several times with methylene chloride. The combined extracts are dried, filtered and concentrated, and then purification is carried out on a silica gel column using toluene/ethyl acetate=8:2 as eluant.

Yield: 50 g (27.7% of theory),
M.p.: 113°–115° C.
Calculated: C 33.75; H 3.64; N 11.26; S 12.87; Br 32.08. Found: C 33.90; H 3.63; N 11.25; S 12.69; Br 32.25.

EXAMPLE X

2-Hydroxy-2-(2-methyl-oxazol-4-yl)ethanamine (a) 2-Methyl-4-formyl-oxazole-cyanohydrin Prepared analogously to Example V by reaction of 6 g (0.0543 mol) of 2-methyl-4-formyl-oxazole with 5.45 g (0.112 mol) of sodium cyanide and 14.4 g (0.1 mol) of potassium dihydrogen phosphate in 180 ml of water and 60 ml of dioxan.

Yield: 6.2 g (83% of theory),
The substance is oily.
Calculated: C 52.17. H 4.37; N 20.28. Found: C 52.08; H 4.50; N 19.98.

(b) 2-Hydroxy-2-(2-methyl-oxazol-4-yl)ethanamine

Prepared analogously to Example P by reaction of 6 g (0.0435 mol) of 2-methyl-4-formyl-oxazole-cyanohydrin with 8.25 g (0.217 mol) of sodium borohydride in tetrahydrofuran and 24.6 g (0.214 mol) of trifluoroacetic acid.

Yield: 2.7 g (44% of theory),
The substance is oily.
Calculated: C 50.69; H 7.09; N 19.70. Found: C 50.32; H 7.22; N 19.68.

$^1$H-NMR spectrum (80 MHz) (CDCl$_3$): δ=7.55 ppm (s,1H).

EXAMPLE Y

2-Chloro-4-bromoacetyl-thiazole 7.6 g (6.0344 mol) of 2-Amino-4-bromoacetyl-thiazole are dissolved in 20 ml of water and 50 ml of concentrated hydrochloric acid. Now, at 0° C. and with stirring, a solution of 3.44 g (0.0499 mol) of sodium nitrite in 15 ml of water is added dropwise. The resulting diazonium salt solution is then introduced in portions into a vigorously stirred cold solution of 4.93 g (0.0449 mol) of copper(I) chloride in 15 ml of concentrated hydrochloric acid, and the mixture is stirred at room temperature for 20 hours. It is then diluted with 100 ml of water and extracted with ether. The ether extract is dried over sodium sulphate and evaporated. For purification, the crude product is purified on a silica gel column using methylene chloride as the eluant.

Yield: 4 g (48% of theory),
M.p.: 72° C.
Calculated: C 24.96; H 1.25; N 5.82. Found: C 25.12; H 1.30; N 6.00.

EXAMPLE Z

2-Piperidino-4-bromoacetyl-thiazole 7.2 g (0.05 mol) of piperidino-thiourea are heated to reflux in a soxhlet apparatus for 10 hours with a solution of 12.2 g (0.05 mol) of dibromodiacetyl in 1 l of ether. The precipitated yellow compound is filtered off with suction and dissolved in 500 ml of chloroform, and the chloroform solution is extracted with 400 ml of saturated sodium bicarbonate solution. The chloroform solution is then dried over sodium sulphate and evaporated. The crude product is purified on a silica gel column using toluene as eluant.

Yield: 7.5 g (52% of theory),
M.p.: 78°–80° C.
Calculated: C 41.53; H 4.52; N 9.68; Br 27.63. Found: C 41.80; H 4.47; N 9 40; Br 27.57.

EXAMPLE ZA

2-Methoxy-2-(2-methyl-thiazol-4-yl)ethanamine

Prepared analogously to Example L by reduction of 4-(α-cyano-α-methoxymethyl)-2-methyl-thiazole [obtained from 4-dimethoxymethyl-2-methyl-thiazole by reaction with trimethylsilyl cyanide in ether in the presence of boron trifluoride etherate] using sodium borohydride in a mixture of tetrahydrofuran and trifluoroacetic acid.

Yield: 80% of theory (oil),
Mass spectrum: Calculated (M+H$^+$)=173. Found (M+H$^+$)=173.

EXAMPLE ZB

2-(2-Trifluoromethyl-thiazol-4-yl)ethylene oxide (a) 1-(2-Trifluoromethyl-thiazol-4-yl)-1-hydroxy-2-bromoethane 6 g (0.022 mol) of 2-Trifluoromethyl-4-bromoacetyl-thiazole are dissolved in 150 ml of methanol, and the solution is cooled to 10° C. and 0.63 g of sodium borohydride is added. After 15 minutes ice is added, and the mixture is acidified with hydrochloric acid, made alkaline with ammonia and extracted by shaking with methylene chloride. The organic phase is dried over sodium sulphate, filtered and concentrated. An oil is obtained and is reacted further as the crude product.

Yield: 5.4 g (89% of theory).
$^1$H NMR spectrum (80 MHz) (CDCl$_3$): δ=7.7 ppm (s,1H).

(b) 2-(2-Trifluoromethyl-thiazol-4-yl)ethylene oxide 5 g (0.018 mol) of 1-(2-Trifluoromethyl-thiazol-4-yl)-1-hydroxy-2-bromoethane are suspended in 4 ml of 50% strength sodium hydroxide solution and stirred for 5 minutes. The mixture is then diluted with ice-water and extracted by shaking with methylene chloride. The organic phase is dried over sodium sulphate and concentrated in vacuo at 20° C., and the resulting oil is purified on a silica gel column using methylene chloride as eluant.
Yield: 2.15 g (67% of theory),
$^1$H NMR spectrum (80 MHz) (CDCl$_3$): δ=7.5 ppm (s, 1H).

EXAMPLE ZC 2-(2-Methyl-thiazol-4-yl)ethylene oxide 10.2 g (0.048 mol) of Trimethylsulphonium iodide are dissolved in 42 ml of dimethyl sulphoxide and added dropwise to a stirred solution, which is maintained at 0° C., of 1.14 g of sodium hydride in 50 ml of dimethyl sulphoxide/tetrahydrofuran (1:1). After 60 minutes, a solution of 6.1 g of 2-methyl-4-formylthiazole in 25 ml of tetrahydrofuran is added dropwise at 0° C., and the mixture is stirred at room temperature for 3 hours. It is then cooled to 0° C., 9.6 ml of water are added dropwise, and the mixture is extracted with ether. The ethereal phase is extracted by shaking 2× with water, dried and concentrated. The resulting oil is purified on a silica gel column using toluene/ethyl acetate (65:35) as eluant.
Yield: 1.6 g (24% of theory),
$^1$H NMR spectrum (80 MHz) (CDCl$_3$): δ=7.1 ppm (s, 1H).

EXAMPLE 1

N-[2-(4-Carbomethoxyphenyl)-1-methylethyl]-N-benzyl-2-hydroxy-2-(2-benzoylamino-thiazol-4-yl)ethanamine 3.5 g (0.011 mol) of 2-Benzoylamino-4-bromoacetyl-thiazole are dissolved in 20 ml of dimethylformamide and added dropwise to a stirred solution, at room temperature, of 2.6 g (0.092 mol) of N-benzyl-2-(4-carbomethoxyphenyl)-1-methylethylamine and 1.1 g (0.011 mol) of triethylamine dissolved in 40 ml of dimethylformamide. After 1.5 hours ice/water is added, and the mixture is extracted with methylene chloride. The extract is dried over sodium sulphate and concentrated. The resulting amino-ketone is taken up in 100 ml of methanol and at room temperature, 0.6 g of sodium borohydride is added. After 1 hour the mixture is evaporated to dryness, water is added, and hydrochloric acid is used to acidify. After 10 minutes the mixture is made alkaline with ammonia and extracted with methylene chloride. The extract is dried over sodium sulphate, concentrated and purified on a silica gel column using toluene/ethyl acetate=8:2 as eluant.
Yield: 1.4 g (29% of theory)
Calculated: C 68.03; H 5.901; N 7.93. Found: C 68.13; H 6.11; N 7.88.
$^1$H NMR spectrum (CDCl$_3$/CD$_3$OD): δ=6.875 ppm (s, 1H).

EXAMPLE 2

N-[2-(4-Carboxyphenyl)-1-methylethyl]-N-benzyl-2-hydroxy-2-(2-amino-thiazol-4-yl)ethanamine 13.6 ml (0.0136 mol) of 1N sodium hydroxide solution are added dropwise at room temperature to a solution of 1.5 g (0.0034 mol) of N-[2-(4-carbomethoxyphenyl)-1-methyl-ethyl]-N-benzyl-2-hydroxy-2-(2-aminothiazol-4-yl)ethanamine in dioxan/methanol=1:1 within 10 minutes, with stirring. After 1 hour 20 ml of water are added dropwise sufficiently slowly that a solution is always maintained. After 16 hours 13.5 ml (0.0136 mol) of 1N hydrochloric acid are added, and the mixture is extracted with methylene chloride which is dried over sodium sulphate and evaporated to dryness, and the resulting base is purified on a silica gel column using ethyl acetate/methanol=9:1.
Yield: 0.36 g (26% of theory),
Calculated: C 64.21; H 6.12; N 10.21. Found: C 64.12; H 6.12; N 9.99.
$^1$NMR spectrum (DMSO): δ=250 ppm (s, 1H).

EXAMPLE 3

N-[2-(4-Carboethoxyphenyl)ethyl]-2-hydroxy-2-(2-benzoylamino-thiazol-4-yl)ethanamine 9.6 g (0.03 mol) of 2-Benzoylamino-4-bromoacetyl-thiazole are dissolved in 100 ml of methylene chloride and, while stirring at room temperature, added dropwise to a solution of 11.5 g (0.06 mol) of 2-(4-carboethoxyphenyl)ethylamine in 150 ml of methylene chloride. After 1.5 hours, the mixture is cooled to 5° C., diluted with 200 ml of methanol and, for the reduction of the resulting amino-ketone, 3 g of sodium borohydride are added in small portions at 0°–5° C. After 3 hours the solution is evaporated to dryness, ice/water is added, and hydrochloric acid is used to acidify. After 10 minutes the mixture is made alkaline with sodium bicarbonate solution and extracted with methylene chloride. The extract is dried over sodium sulphate, concentrated and purified on a silica gel column using chloroform-/methanol=9:1, with the addition of 2% ammonia-saturated ethanol, as eluant. The resulting product is induced to crystallise with petroleum ether.
Yield: 3.4 g (26% of theory),
M.p.: 83°–85° C.
Calculated: C 62.85; H 5.73; N 9.56. Found: C 62.75; H 5.78; N 9.41.

EXAMPLE 4

N-[2-(4-Carboxyphenyl)ethyl]-2-hydroxy-2-(2-benzoylamino-thiazol-4-yl)ethanamine Prepared analogously to Example 2 by reaction of N-[2-(4-carboethoxyphenyl)ethyl]-2-hydroxy-2-(2-benzoylamino-thiazol-4-yl)ethanamine with 1N sodium hydroxide solution, followed by purification of the crude product on a silica gel column using chloroform-/methanol=1:1 and trituration with water/ethanol=9:1.
Yield: 36% of theory,
M.p.: 143°–145° C. (decomp.)
Calculated: C 61.29; H 5.14; N 10.14. Found: C 61.19; H 5.18; N 10.06.

EXAMPLE 5

N-[2-(4-Carboethoxyphenyl)ethyl]-2-hydroxy-2-(2-benzoylamino-4-methyl-thiazol-5-yl)ethanamine Prepared analogously to Example 3 by reaction of 2-(4-carboethoxyphenyl)ethylamine and stoichiometric amounts of triethylamine with 2-benzoylamino-4-methyl-5-bromoacetyl-thiazole, followed by reduction and purification of the base on a silica gel column using chloroform/methanol=9:1 as eluant and trituration with petroleum ether.

Yield: 33% of theory,
M.p.: 96°–98° C.
Calculated: C 63.55; H 6.00; N 9.26. Found: C 63.45; H 5.85; N 9.19.

EXAMPLE 6

N-[2-(4-Carboethoxyphenyl)ethyl]-2-hydroxy-2-(2-acetylamino-4-methyl-thiazol-5-yl)ethanamine Prepared analogously to Example 3 by reaction of 2-(4-carboethoxyphenyl)ethylamine and stoichiometric amounts of triethylamine with 2-acetylamino-4-methyl-5-bromoacetyl-thiazole, followed by reduction and purification of the base on a silica gel column using ethyl acetate/methanol=19:1 as eluant and trituration with ether.

Yield: 33% of theory,
M.p.: 97°–99° C.
Calculated: C 58.29; H 6.44; N 10.73. Found: C 58.40; H 6.58; N 10.61.

EXAMPLE 7

N-[2-(4-Carboxyphenyl)ethyl]-2-hydroxy-2-(2-acetylamino-4- methyl-thiazol-5-yl)ethanamine Prepared analogously to Example 2 by reaction of N-[2-(4-carboethoxyphenyl)ethyl]-2-hydroxy-2-(2-acetylamino-4-methyl-thiazol-5-yl)ethanamine with 1N sodium hydroxide solution. After neutralisation with 1N hydrochloric acid, the mixture is evaporated to dryness, and the residue is recrystallised from 10 ml of water.

Yield: 80% of theory,
M.p.: 156°–158° C.
Calculated: C 56.18; H 5.83; N 11.56. Found: C 56.20; H 5.95; N 11.61.

EXAMPLE 8

N-[2-(4-Carboethoxyphenyl)ethyl]-2-hydroxy-2-(2-amino-4-methyl-thiazol-5-yl)ethanamine dihydrochloride 3 g (0.013 mol) of 2-Amino-4-methyl-5-bromoacetyl-thiazole are added in small portions to a stirred solution of 5.2 g (0.026 mol) of triethylamine in 300 ml of tetrahydrofuran at room temperature. After 2 hours the mixture is evaporated to dryness. The resulting residue is dissolved in ethanol and, for the reduction of the amino-ketone which has formed, 1.5 g of sodium borohydride are added in small portions while stirring at 15° C. After 16 hours the solution is evaporated to dryness, water is added, and the mixture is acidified with hydrochloric acid. It is then made alkaline with ammonia and extracted with methylene chloride. The extract is dried over sodium sulphate, concentrated and purified on a silica gel column using chloroform/methanol=8:2 as eluant. The resulting base is dissolved in ethanol, converted into the dihydrochloride with isopropanolic hydrochloric acid and acetone, and the product is washed with ether.

Yield: 3.5 g (64% of theory),
M.p.: 160° C.
Calculated: C 48.34; H 5.97; N 9.95. Found: C 48.23; H 6.20; N 9.97.

EXAMPLE 9

N-[2-(4-Carboxyphenyl)ethyl]-2-hydroxy-2-(2-amino-thiazol-4-yl)ethanamine dihydrochloride 1.5 g (0.0043 mol) of N-[2-(4-Carboxyphenyl)ethyl]-2-hydroxy-2-(2-acetylamino-thiazol-4-yl)ethanamine are dissolved in 30 ml of 1N hydrochloric acid, and the solution is heated at 90° C. for 2.5 hours and then evaporated to dryness. The remaining residue is recrystallised from a mixture of 50 ml of ethanol and 3 ml of water, and the resulting crystals are washed with ether.

Yield: 1.4 g (85% of theory),
M.p.: 218°–219° C.
Calculated: C 44.21; H 5.04; N 11.05. Found: C 44.40; H 5.17; N 10.94.

EXAMPLE 10

N-[2-(4-Carbomethoxyphenyl)-1-methylethyl]-2-hydroxy-2-(2-acetylamino-thiazol-4-yl)ethanamine hydrochloride Prepared analogously to Example 3 by reaction of 2-(4-carbomethoxyphenyl)-1-methyl-ethanamine and triethylamine in tetrahydrofuran with 2-acetylamino-4-bromoacetyl-thiazole, followed by reduction and purification of the base on a silica gel column using ethyl acetate/methanol=9:1 as eluant and precipitating the hydrochloride with isopropanolic hydrochloric acid.

Yield: 36% of theory,
M.p.: 118°–120° C.
Calculated: C 52.23; H 5.84; N 10.15. Found: C 51.98; H 6.01; N 9.97.

According to the $^1$H NMR spectrum (400 MHz), the product is an approximately 35:65 mixture of diastereomers.

EXAMPLE 11

N-[2-(4-Carboxyphenyl)-1-methylethyl]-2-hydroxy-2-(2-amino-thiazol-4-yl)ethanamine dihydrochloride Prepared analogously to Example 9 by reaction of N-[2-(4-carboxyphenyl)-1-methylethyl]-2-hydroxy-2-(2-acetylamino-thiazol-4-yl)ethanamine and 1N hydrochloric acid.

Yield: 79% of theory,
M.p.: 167° C.
Calculated: C 45.69; H 5.37; N 10.66. Found: C 45.49; H 5.51; N 10.54.

According to the $^1$H NMR spectrum (400 MHz) the product is an approximately 40:60 diastereomer mixture.

EXAMPLE 12

N-[2-(4-Carbomethoxyphenyl)-1-methylethyl]-2-hydroxy-2-(2-trifluoromethyl-thiazol-4-yl)ethanamine 1.3 g (0.0062 mol) of 2-(2-trifluoromethyl-thiazol-4yl)glyoxal and 1.2 g (0.0057 mol) of 2-(4-carboethoxyphenyl)-1-methyl-ethanamine are mixed at 50° C. and stirred at room temperature for 4 hours. For the reduction of the resulting Schiff's base, 0.75 g of sodium borohydride is added in portions at 20° C., and the mixture is stirred for 16 hours. It is then poured onto ice, and the mixture is acidified with hydrochloric acid, made alkaline with sodium bicarbonate solution and extracted with methylene chloride. The extract is dried over sodium sulphate, concentrated and purified on a silica gel column using methylene chloride/methanol=40:1 as eluant.

Yield: 1.5 g (68% of theory),

Calculated: C 52.57; H 4.93; N 7.21. Found: C 52.71; H 5.08; N 7.30.

$^1$H NMR spectrum (CDCl$_3$): $\delta$=4.735 ppm (dd, =CH—OH); $\delta$=4.895 ppm (dd, =CH—OH).

According to the $^1$H NMR spectrum (400 MHz) the product is an approximately 60:40 diastereomer mixture.

EXAMPLE 13

N-[2-(4-Carbomethoxymethoxyphenyl)-1-methylethyl]-2-hydroxy-2-(2-phenyl-thiazol-4-yl)ethanamine 1.32 g (0.006 mol) of 2-Hydroxy-2-(2-phenyl-thiazol-4-yl)ethanamine and 1.33 g (0.006 mol) of 1-(4-carbomethoxymethoxyphenyl)-propan-2-one are dissolved in 40 ml of absolute methanol, and 0.34 ml (0.006 mol) of glacial acetic acid and 0.37 g (0.006 mol) of sodium cyanoborohydride are added and the mixture is stirred at room temperature for 20 hours. It is then poured onto ice, and the mixture is acidified with hydrochloric acid, made alkaline with sodium bicarbonate solution and extracted with chloroform. The extract is dried over sodium sulphate, concentrated and purified on a silica gel column using ethyl acetate/methanol=9:1 as eluant.

Yield: 2.2 g (86% of theory)

Calculated: C 64.76; H 6.14; N 6.56; S 7.51. Found: C 64.50; H 6.42; N 6.39; S 7.30.

$^1$H NMR spectrum (CDCl$_3$): $\delta$=4.88 ppm (dd, =CH—OH); $\delta$=4.93 ppm (dd, =CH—OH).

According to the $^1$H NMR spectrum (400 MHz) the product is an approximately 50:50 diastereomer mixture.

EXAMPLE 14

N-[2-(4-Aminocarbonylmethoxyphenyl)-1-methylethyl]-2-hydroxy-2-(2-methyl-thiazol-4-yl)ethanamine 1 g (0.0027 mol) of N-[2-(4-Carbomethoxymethoxyphenyl)-1-methylethyl]-2-hydroxy-2-(2-methyl-thiazol-4-yl)ethanamine is dissolved in 5 ml of methanol and stirred with 5 ml of concentrated ammonia at room temperature for 3 hours. The mixture is then diluted with water and extracted with methylene chloride. The extract is dried over sodium sulphate, concentrated and purified on a silica gel column using ethyl acetate/methanol=9:1 as eluant.

Yield: 0.76 (81% of theory),

M.p.: 148° C.

Calculated: C 58.43; H 6.63; N 12.02. Found: C 58.62; H 6.69; N 12.00.

According to the $^1$H NMR spectrum (400 MHz) the product is an approximately 25:75 diastereomer mixture.

EXAMPLE 15

N-[2-(4-Methylaminocarbonylmethoxyphenyl)-1-methylethyl]-2-hydroxy-2-(2-trifluoromethyl-thiazol-4-yl)ethanamine prepared analogously to Example 3 by reaction of 2-trifluoromethyl-4-bromoacetylthiazole and 2-(4-methylaminocarbonylmethoxyphenyl)-1-methylethylamine, followed by reduction and purification of the base on a silica gel column using methylene chloride/methanol=9:1 as eluant.

Yield: 10% of theory,

Calculated: C 51.79; H 5.31; N 10.17. Found: C 51.79; H 5.55; N 10.91.

$^1$H NMR spectrum (CDCl$_3$/CD$_3$OD): $\delta$=7.575 ppm (s, 1H), $\delta$=7.595 ppm (s, 1H).

According to the $^1$H NMR spectrum (400 MHz) the product is an approximately 50:50 diastereomer mixture.

EXAMPLE 16

N-[2-(4-Carboxyphenyl)-1-methylethyl]-2-hydroxy-2-(2-trifluoromethyl-thiazol-4-yl)ethanamine Prepared analogously to Example 2 by reaction of N-[2-(4-carbomethoxyphenyl)-1-methylethyl]-2-hydroxy-2-(2-trifluoromethyl-thiazol-4-yl)ethanamine with 1N sodium hydroxide solution. After neutralisation with hydrochloric acid, the mixture is evaporated to dryness and the residue is treated with a mixture of ethyl acetate/ethanol=6:1. The extract is evaporated to dryness and the residue is triturated with 5 ml of water. The water is decanted off and the remaining residue is taken up in methanol, the solution is evaporated to dryness, and the residue is triturated with ether and filtered off with suction.

Yield: 52% of theory,

M.p.: 107°–109° C.,

Calculated: C 51.33; H 4.58; N 7.48. Found: C 51.41; H 4.74; N 7.42.

According to the $^1$NMR spectrum (400 MHz) the product is an approximately 60:40 diastereomer mixture.

EXAMPLE 17

N-[2-(4-Carbomethoxymethoxyphenyl)-1-methylethyl]-2-(2-trifluoromethyl-thiazol-4-yl)morpholine Prepared analogously to Example 13 by reaction of 2-(2-trifluoromethyl-thiazol-4-yl)morpholine with 1-(4-carbomethoxymethoxyphenyl)propan-2-one followed by purification of the base on a silica gel column using toluene/ethyl acetate=8:2 as eluant.

Yield: 54% of theory,

Calculated: C 54.04; H 5.22; N 6.30. Found: C 54.28; H 5.24; N 6.46.

$^1$H NMR spectrum (CDCl$_3$): $\delta$=7.610 ppm (s, 1H); $\delta$=7.575 ppm (s, 1H).

According to the $^1$H NMR spectrum (400 MHz) the product is an approximately 50:50 diastereomer mixture.

EXAMPLE 18

Methyl 3-[2-(4-Carbomethoxymethoxyphenyl)-1-methylethyl]-5-(2-trifluoromethyl-thiazol-4-yl)-2-oxazolidinecarboxylate 0.52 g (0.0012 mol) of N-[2-(4-carbomethoxymethoxyphenyl)-1-methylethyl]-2-hydroxy-2-(2-trifluoromethylthiazol-4-yl)ethanamine and 0.211 g (0.0024 mol) of methyl glyoxylate and 25 ml toluene are heated at 120° C. for 10 minutes and then boiled under a water trap for 1 hour. The solution is cooled, 50 ml of ethyl acetate are added, and the mixture is shaken with 30 ml of water. The organic phase is separated off, dried over sodium sulphate and concentrated. The residue is purified on a laboratory size B prepacked column (supplied by Merck) using toluene/ethyl acetate=20:1.5 as eluant. Frction A (diastereomer pairs A and B), Yield: 90 mg (15.4% of theory), $^1$H NMR spectrum (CDCl$_3$/CD$_3$OD): δ=5.10 ppm (s, 1H); δ=5.24 ppm (s, 1H).

According to $^1$H NMR spectrum (400 MHz) the product is an approximately 50:50 diastereomer mixture.

Fraction B (diastereomer pairs C and D):

Yield: 110 mg (18.8% of theory), $^1$H NMR spectrum (CDCl$_3$/CD$_3$OD): δ=4.97 ppm (s, 1H); δ=5.21 ppm (s, 1H).

According to 1H NMR spectrum (400 MHz) te product is an approximately 50:50 diastereomer mixture.

EXAMPLE 19

Methyl 3-[2-(4-carbomethoxyphenyl)-1-methylethyl]-5-(2-trifluoromethyl-thiazol-4-yl)-2-oxazolidine carboxylate Prepared analogously to Example 18 by reaction of N-[2-(4-carbomethoxyphenyl)-1-methylethyl]-2-hydroxy-2-(2-trifluoromethyl-thiazol-4-yl)ethanamine with methyl glyoxylate.

Fraction A (diastereomer pairs A and B):

Yield: 25% of theory, $^1$H NMR spectrum (CDCl$_3$/CD$_3$OD): δ=5.07 ppm (s, 1H) δ=5.26 ppm (s, 1H).

According to the $^1$H NMR spectrum (400 MHz) the product is an approximately 45:55 diastereomer mixture.

Fraction B (diastereomer pairs C and D):

Yield: 23% of theory, $^1$H NMR spectrum (CDCl$_3$/CD$_3$OD): δ=5.08 ppm (s, 1H); δ=5.22 ppm (s, 1H).

According to the $^1$H NMR spectrum (400 MHz) the product is an approximately 35:65 diastereomer mixture.

EXAMPLE 20

N-[2-(4-Carbomethoxymethoxyphenyl)-1-methylethyl]-2-hydroxy-2-(2-trifluoromethyl-thiazol-4-yl)ethanamine Prepared analogously to Example 3 by reaction of 2-(4-carbomethoxymethoxyphenyl)-1-methyl-ethanamine with 2-trifluoromethyl-4-bromoacetyl-thiazole followed by reduction and purification of the base on a silica gel column with methylene chloride/methanol=20:1 as eluant.

Yield: 51% of theory,

Calculated: C 51.66; H 5.06; N 6.70. Found: C 51.40; H 5.14; N 6.64.

$^1$H NMR spectrum (CDCl$_3$): δ=4.835 ppm (dd, =C$\underline{H}$—OH); δ=4.895 ppm (dd, =C$\underline{H}$—OH).

According to $^1$H NMR spectrum (400 MHz) the product is an approximately 60:40 diastereomer mixture.

EXAMPLE 21

N-[2-(4-Carbomethoxyphenyl)-1-methylethyl]-2-hydroxy-2-(4-methyl-oxazol-5-yl)ethanamine dihydrochloride 2.6 g (0.009 mol) of 4-Methyl-5-bromoacetyl-oxazole and 1.16 g (0.009 mol) of N,N-diisopropyl-ethylamine are dissolved in 50 ml of methylene chloride. This solution is added dropwise, within 20 minutes to 3.47 g (0.018 mol) of 2-(4-carbomethoxyphenyl)-1-methylethylamine in 100 ml of methylene chloride, and the mixture is stirred at room temperature for 2 hours and at 35° C. for 1 hour. The reaction solution is cooled in an ice bath, and 150 ml of methanol are added. Then, for the reduction of the resulting amino-ketone, 1 g of sodium borohydride is added in portions over 30 minutes, and the mixture is stirred at room temperature for 20 hours and then evaporated. Ice-water is then added to the residue, and the mixture is acidified with hydrochloric acid, made alkaline with concentrated aqueous ammonia and extracted with chloroform. The extract is dried over sodium sulphate, concentrated and purified on a silica gel column using ethyl acetate/methanol=9:1 as eluant. The hydrochloride is then precipitated with ethereal hydrochloric acid.

Yield: 1.1 g (31% of theory),

M.p.: 80° C. (decomp.)

Calculated: C 52.17; H 6.18; N 7.13; Cl 18.14. Found: C 52.00; H 6.10; N 6.90; Cl 17.90.

According to the 1H NMR spectrum (400 MHz) the product is an approximately 50:50 diastereomer mixture.

EXAMPLE 22

N-[2-(4-Carbomethoxyphenyl)-1-methylethyl]-2-hydroxy-2-(thiazol-4-yl)ethanamine

Prepared analogously to Example 3 by reaction of 2-(4-carbomethoxyphenyl)-1-methylethylamine with 4-bromoacetyl-thiazole, followed by reduction and purification of the base on a silica gel plate using ethyl acetate/methanol=8:2 as eluant.

Yield: 9% of theory,

Calculated: C 59.97; H 6.29; N 8.75. Found: C 60.09; H 6.01; N 8.56.

$^1$H NMR spectrum (CDCl$_3$): δ=4.900–4.970 ppm (m, =C$\underline{H}$—OH).

According to the $^1$H NMR spectrum (400 MHz) the product is an approximately 60:40 diastereomer mixture.

EXAMPLE 23

N-[2-(4-Carbomethoxymethoxyphenyl)-1-methylethyl]-N-methyl-2-hydroxy-2-(2-trifluoromethyl-thiazol-4-yl)ethanamine Prepared analogously to Example 3 by reaction of 2-trifluoromethyl-4-bromoacetyl-thiazole and N-methyl-2-(4-carbomethoxymethoxyphenyl)-1-methylethylamine, followed by reduction and purification of the base on a silica gel column using ethyl acetate/methanol=40:1 as eluant.

Yield: 53% of theory,

Calculated: C 52.77; H 5.36; N 6.48. Found: C 53.00; H 5.06; N 6.64.

$^1$H NMR spectrum (CDCl$_3$/CD$_3$OD): δ=7.555 ppm (s, 1H); δ=7.575 ppm (s, 1H).

According to the $^1$H NMR spectrum (400 MHz) the product is an approximately 50:50 diastereomer mixture.

EXAMPLE 24

N-[2-(4-Aminocarbonylmethoxyphenyl)-1-methylethyl]-2-hydroxy-2-(2-trifluoromethyl-thiazol-4-yl)ethanamine Prepared analogously to Example 14 by reaction of N-[2-(4-carbomethoxymethoxyphenyl)-1-methylethyl]-2-hydroxy-2-(2-trifluoromethyl-thiazol-4-yl)ethanamine with concentrated ammonia followed by purification of the base on a silica gel column using methylene chloride/methanol=9:1 as eluant.

Yield: 65% of theory,

Calculated: C 50.61; H 5.00; N 10.42. Found: C 50.43; H 5.19; N 10.37.

$^1$H NMR spectrum (CDCl$_3$): δ=4.850 ppm (dd, =CH—OH); δ=4.775 ppm (dd, =CH—OH).

According to the $^1$H NMR spectrum (400 MHz) the product is an approximately 60:40 diastereomer mixture.

EXAMPLE 25

N-[2-(4-Carbomethoxymethoxyphenyl)-1-methylethyl]-2-hydroxy-2-(2-methyl-thiazol-4-yl)ethanamine Prepared analogously to Example 13 by reaction of 2-hydroxy-2-(2-methyl-thiazol-4-yl)ethanamine with 1-(4-carbomethoxymethoxyphenyl)propan-2-one followed by purification of the base on a silica gel column using ethyl acetate/methanol=9:1 as eluant.

Yield: 55% of theory,

Calculated: C 59.32; H 6.64; N 7.69. Found: C 59.20; H 6.45; N 7.91.

$^1$H NMR spectrum (CDCl$_3$): δ=4.825 ppm (dd, =CH—OH); δ=4.775 ppm (dd, =CH—OH).

According to the $^1$H NMR spectrum (400 MHz) the product is an approximately 50:50 diastereomer mixture.

EXAMPLE 26

N-[2-(4-Carbomethoxymethoxyphenyl)-1-methylethyl]-2-hydroxy-2-(thiazol-4-yl)ethanamine Prepared analogously to Example 13 by reaction of 2-hydroxy-2-(thiazol-4-yl)ethylamine with 1-(4-carbomethoxymethoxyphenyl)propan-2-one followed by purification of the base on a silica gel column using ethyl acetate/methanol=8:2 as eluant.

Yield: 48% of theory,

Calculated: C 58.26; H 6.33; N 8.00. Found: C 58.41; H 6.36; N 8.22.

$^1$H NMR spectrum (CDCl$_3$): δ=4.945 ppm (dd, =CH—OH); δ=4.900 ppm (dd, =CH—OH).

According to the $^1$H NMR spectrum (400 MHz) the product is an approximately 50:50 diastereomer mixture.

EXAMPLE 27

N-[2-(4-Carbomethoxyphenyl)-1-methylethyl]-2-hydroxy-2-(2,5-dimethyl-oxazol-4-yl)ethanamine dihydrochloride Prepared analogously to Example 21 by reaction of 2,5-dimethyl-4-bromoacetyl-oxazole with 2-(4-carbomethoxyphenyl)-1-methylethylamine, followed by reduction and precipitation of the dihydrochloride using ethereal hydrochloric acid.

Yield: 47% of theory,

Melting point: 78° C. (decomp.)

Calculated: C 53.33; H 6.46; N 6.90; Cl 17.51. Found: C 53.10; H 6.50; Cl 6.80.

According to the $^1$H NMR spectrum (400 MHz) the product is an approximately 50:50 diastereomer mixture.

EXAMPLE 28

N-[2-(4-Carbomethoxymethoxyphenyl)-1-methylethyl]-2-hydroxy-2-(2,5-dimethyl-oxazol-4-yl)ethanamine dihydrochloride Prepared analogously to Example 21 by reaction of 2,5-dimethyl-4-bromoacetyl-oxazole with 2-(4-carbomethoxymethoxyphenyl)-1-methylethylamine, followed by reduction and precipitation of the dihydrochloride using ethereal hydrochloric acid.

Yield: 47% of theory,

M.p.: 82° C. (decomp.)

Calculated: C 52.41; H 6.48; N 6.43; Cl 16.28. Found: C 52.21; H 6.55; N 6.50; Cl 16.40.

According to the $^1$H NMR spectrum (400 MHz) the product is an approximately 50:50 diastereomer mixture.

EXAMPLE 29

N-[2-(4-Carbomethoxymethoxyphenyl)-1-methylethyl]-2-hydroxy-2-(2,4-dimethyl-thiazol-5-yl)ethanamine Prepared analogously to Example 3 by reaction of 2,4-dimethyl-5-bromoacetyl-thiazole with 2-(4-carbomethoxymethoxyphenyl)-1-methylethylamine, followed by reduction and purification of the base on a silica gel column using ethyl acetate/methanol=17:3.

Yield: 45% of theory,

Calculated: C 60.29; H 6.92; N 7.40. Found: C 60.53; H 6.85; N 7.60.

$^1$H NMR spectrum (CDCl$_3$/CD$_3$OD): δ=4.890–4.970 ppm (m, =CH—OH).

According to the $^1$H NMR spectrum (400 MHz) the product is an approximately 53:47 diastereomer mixture.

EXAMPLE 30

N-[2-(4-Carbomethoxymethoxyphenyl)-1-methylethyl]-N-(2-hydroxyethyl)-2-hydroxy-2-(2-trifluoromethyl-thiazol-4-yl)ethanamine Prepared analogously to Example 3 by reaction of 2-trifluoromethyl-4-bromoacetyl-thiazole and N-(2-hydroxyethyl)-2-(4-carbomethoxymethoxyphenyl)-1-methylethylamine. Before the reduction with sodium borohydride, the mixture is heated to boiling for 3 hours to complete the reaction. The base is then purified on a silica gel column using ethyl acetate as mobile phase.

Yield: 50% of theory,

Calculated: C 51.94; H 5.45; N 6.06. Found: C 52.00; H 5.33; N 6.09.

$^1$H NMR spectrum (CDCl$_3$):

$^1$H NMR spectrum (CDCl$_3$):

δ = 0.930 ppm (d, —CH—);

δ = 0.970 ppm (d, —CH—)
$\quad$ CH$_3$
$\quad$ CH$_3$

EXAMPLE 31

N-[2-(4-Carbomethoxymethoxyphenyl)-1-methylethyl]-2-hydroxy-2-(2-trifluoromethyl-5-methyl-oxazol-4-yl)ethanamine hydrochloride Prepared analogously to Example 21 by reaction of 2-trifluoromethyl-5-methyl-4-bromoacetyl-oxazole with 2-(4-carbomethoxymethoxyphenyl)-1-methylethylamine followed by reduction. The compound is purified on a silica gel column using ethyl acetate/methanol=20:1 as eluant, and then the hydrochloride is precipitated with ethereal hydrochloric acid.

Yield: 0.43 g (10% of theory),
M.p.: 58° C.
Calculated: C 50.38; H 5.34; N 6.18; Cl 7.82. Found: C 50.58; H 5.33; N 5.93; Cl 8.20.

EXAMPLE 32

N-[2-(4-Carbomethoxymethoxyphenyl)-1-methylethyl]-2-(2-trifluoromethyl-thiazol-4-yl)morpholine Prepared analogously to Example 3 by reaction of 11.6 g (0.043 mol) of 2-trifluoromethyl-4-bromoacetylthiazole with 23 g (0.086 mol) of N-(2-hydroxyethyl)-2-(4-carbomethoxymethoxyphenyl)-1-methylethylamine. To complete the reaction the mixture is heated to boiling for 6 hours. It is then concentrated in vacuo, and the resulting residue is dissolved in 85 ml of trifluoroacetic acid and, at room temperature, 7 g (0.06 mol) of triethylsilane are added. After 90 hours the solution is poured onto ice, and concentrated ammonia is added, and the mixture is extracted several times with methylene chloride. The organic phase is dried over sodium sulphate and concentrated, and the residue is purified on a silica gel column using toluene/ethyl acetate=8/2 as eluant.

Yield: 11 g (58% of theory),
$^1$H NMR spectrum: δ=7.610 ppm (s, 1H); 7.578 ppm (s, 1H).

According to the $^1$H NMR spectrum (400 MHz) the product is an approximately 43:57 diastereomer mixture.

EXAMPLE 33

N-[2-(4-Carbomethoxymethoxyphenyl)-1-methylethyl]-2-hydroxy-2-(2-trifluoromethyl-5-methyl-thiazol-4-yl)ethanamine Prepared analogously to Example 3 by reaction of 2-trifluoromethyl-5-methyl-4-bromoacetyl-thiazole with 2-(4-carbomethoxymethoxyphenyl)-1-methylethylamine followed by reduction. The compound is purified on a silica gel column using ethyl acetate/methanol=9/1 as eluant.

Yield: 8% of theory,
Calculated: C 52.77; H 5.36; N 6.47. Found: C 52.60; H 5.44; N 6.55.

$^1$N NMR spectrum (CDCl$_3$): δ=4.765 ppm (dd, =CH—OH); δ=4.810 ppm (dd, =CH—OH).

According to the $^1$H-NMR spectrum (400 MHz) the product is an approximately 54:46 diastereomer mixture.

EXAMPLE 34

N-[3-(4-Carboxamidophenyl)-1-methylpropyl]-2-hydroxy-2-(2-trifluoromethyl-thiazol-4-yl)ethanamine Prepared analogously to Example 13 by reaction of 2-hydroxy-2-(2-trifluoromethyl-thiazol-4-yl)ethanamine with 1-(4-carboxamidophenyl)butan-3-one followed by purification of the base on a silica gel column using ethyl acetate/methanol=5/1 as eluant.

Yield: 26% of theory,
M.p.: 119°-121° C.
Calculated: C 52.70; H 5.20; N 10.85. Found: C 52.61; H 5.35; N 10.84.

According to $^1$H NMR spectrum (400 MHz), the product is an approximately 50:50 diastereomer mixture.

EXAMPLE 35

N-[2-(4-Carboxymethoxyphenyl)-1-methylethyl]-2-(2-trifluoromethyl-thiazol-4-yl)morpholine Prepared analogously to Example 16 by reaction of N-[2-(4-carbomethoxymethoxyphenyl)-1-methylethyl]-2-(2-trifluoromethyl-thiazOl-4-yl)morphOline in methanol with 1N sodium hydroxide solution. After neutralisation with 1N hydrochloric acid, the mixture is extracted by shaking with methylene chloride, the extract is evaporated to dryness, and the remaining residue is triturated with petroleum ether and filtered off with suction.

Yield: 94% of theory,
M.p.: 86° C.
Calculated: C 53.01; H 4.92; N 6.51. Found: C 53.14; H 4.85; N 6.54.

EXAMPLE 36

N-[2-(4-Carboxymethoxyphenyl)-1-methylethyl]-2-hydroxy-2-(2-trifluoromethyl-thiazol-4-yl)ethanamine Prepared analogously to Example 16 by reaction of N-[2-(4-carbomethoxymethoxyphenyl)-1-methylethyl]-2-(2-trifluoromethyl-thiazol-4-yl)ethanamine in methanol with 1N sodium hydroxide solution. After neutralisation with 1N hydrochloric acid, the mixture is extracted by shaking with methylene chloride, the extract is evaporated to dryness, and the remaining residue is triturated with petroleum ether and filtered off with suction.

Yield: 50% of theory,
M.p.: 80°-82° C. (decomp.)
Calculated: C 50.49; H 4.74; N 6.93. Found: C 50.60; H 4.61; N 7.04.

EXAMPLE 37

N-[2-(4-Carbomethoxymethoxyphenyl)-1-methylethyl]-2-hydroxy-2-(2-chloro-thiazol-4-yl)ethanamine hydrochloride Prepared analogously to Example 13 by reaction of 2-hydroxy-2-(2-chloro-thiazol-4-yl)ethanamine with 1-(4-carbomethoxymethoxyphenyl)-propan-2-one followed by precipitation of the hydrochloride with ethereal hydrochloric acid.

Yield: 43% of theory,

M.p.: 58° C. (decomp.)
Calculated: C 48.45; H 5.26; N 6.64; Cl 16.82; S 7.60.
Found: C 48.48; H 5.23; N 6.61; Cl 16.67; S 7.87.

EXAMPLE 38

N-[2-(4-(2-Carbomethoxy-1-methylethenyl)phenyl)-1-methylethyl]-2-hydroxy-2-(2-trifluoromethyl-thiazol-4-yl)ethanamine Prepared analogously to Example 13 by reaction of 2-hydroxy-2-(2-trifluoromethyl-thiazol-4-yl)ethanamine with 1-[4-(2-carbomethoxy-1-methylethenyl)-phenyl]-propan-2-one followed by purification of the base on a silica gel column using chloroform/methanol/methanolic ammonia=9.5/0.4/0.1 as eluant.

Yield: 43% of theory,

Calculated: C 56.00; H 5.41; N 6.54; S 7.48. Found: C 56.00; H 5.57; N 6.37; S 7.76.

According to $^1$H NMR spectrum (400 MHz) the product is an approximately 3:4 diastereomer mixture.

EXAMPLE 39

N-[2-(4-(2-Carbomethoxy-1-methylethenyl)phenyl)-1-methylethyl]-2-(2-trifluoromethyl-thiazol-4-yl)morpholine Prepared analogously to Example 13 by reaction of 2-(2-trifluoromethyl-thiazol-4-yl)morpholine with 1-[4-(2-carbomethoxy-1-methylethenyl)phenyl]propan-2-one followed by purification of the base on a silica gel column using chloroform/ethyl acetate=19:1 as eluant.

Yield: 29% of theory,

Calculated: C 58.14; H 5.54; N 6.16; S 7.05. Found: C 58.38; H 5.49; N 5.96; S 7.40.

According to the $^1$H NMR spectrum (400 MHz) the product is an approximately 50:50 diastereomer mixture.

EXAMPLE 40

N-[2-(4-(2-Carbomethoxy-1-methylethenyl)phenyl)-1-methylethyl]-2-hydroxy-2-(2-methyl-thiazol-4-yl)ethanamine Prepared analogously to Example 13 by reaction of 2-hydroxy-2-(2-methyl-thiazol-4-yl)ethanamine with 1-[4-(2-carbomethoxy-1-methylethenyl)phenyl]propan-2-one followed by purification of the base on a silica gel column using toluene/methanol=19:1 as eluant.

Yield: 32% of theory,

Calculated: C 65.97; H 7.05; N 6.99; S 8.01. Found: C 65.70; H 7.16; N 6.88; S 8.05.

According to the $^1$H NMR spectrum (400 MHz) the product is an approximately 50:50 diastereomer mixture.

EXAMPLE 41

N-[2-(4-(2-Carbomethoxy-1-methylethenyl)phenyl)-1-methylethyl]-2-(2-methyl-thiazol-4-yl)morpholine Prepared analogously to Example 13 by reaction of 2-(2-methyl-thiazol-4-yl)morpholine with 1-[4-(2-carbomethoxy-1-methyl-ethenyl)phenyl]propan-2-one followed by purification of the base on a silica gel column using chloroform/methanol/ammonia=9:1:0.1 as eluant.

Yield: 59% of theory,

Calculated: C 64.13; H 7.00; N 7.48; S 8.56. Found: C 63.90; H 6.86; N 7.20; S 8.28.

According to the $^1$H NMR spectrum (400 MHz) the product is an approximately 50:50 diastereomer mixture.

EXAMPLE 42

N-[2-(4-Hydroxyphenyl)-1-methylethyl]-2-(2-methyl-thiazol-4-yl)morpholine

Prepared analogously to Example 13 by reaction of 2-(2-methyl-thiazol-4-yl)morpholine with 1-4-hydroxyphenyl)-propan-2-one followed by purification of the base on a silica gel column using toluene/methanol=9:1 as eluant.

Yield: 46% of theory,

Calculated: C 64.12; H 6.96; N 8.80; S 10.07. Found: C 63.90; H 7.03; N 8.73; S 9.83.

According to the $^1$H NMR spectrum (400 MHz) the product is an approximately 50:50 diastereomer mixture.

EXAMPLE 43

N-[2-(4-Carbomethoxymethoxyphenyl)ethyl]-2-hydroxy-2-(2-trifluoromethyl-thiaol-4-yl)ethanamine Prepared analogously to Example 3 by reaction of 2-trifluoromethyl-4-bromoacetyl-thiazole with 2-(4-carbomethoxymethoxyphenyl)ethanamine, followed by reduction.

Yield: 15% of theory,

M.p.: 91°–92° C.

Calculated: C 50.49; H 4.74; N 6.93; S 7.93. Found: C 50.74; H 4.94; N 6.84; S 8.10.

EXAMPLE 44

N-[3-(4-Carboxamidophenyl)-1-methylpropyl]-2-hydroxy-2-(2-methyl-thiazol-4-yl)ethanamine Prepared analogously to Example 13 by reaction of 2-hydroxy-2-(2-methyl-thiazol-4-yl)ethanamine with 1-(4-carboxamidophenyl)butan-3-one.

Yield: 46% of theory,

M.p.: 94°–95° C.

Calculated: C 61.24; H 6.95; N 12.60; S 9.61. Found: C 61.50; H 7.15; N 12.34; S 9.65.

According to the $^1$H NMR spectrum (400 MHz) the product is a 50:50 mixture of diastereomers.

EXAMPLE 45

N-[3-(4-Carboxamidophenyl)-1-methylpropyl]-2-(2-trifluoromethyl-thiazol-4-yl)morpholine Prepared analogously to Example 32 by reaction of N-(2-hydroxyethyl)-3-(4-carboxamidophenyl)-1-methylpropylamine with 2-trifluoromethyl-4-bromoacetyl-thiazole followed by reduction with triethylsilane.

Yield: 19.7% of theory,

M.p.: 95°–105° C.

Calculated: C 55.19; H 5.36; N 10.16; S 7.76. Found: C 55.20; H 5.45; N 9.98; S 7.91.

$^1$H NMR spectrum (CDCl$_3$): δ=4.74 ppm (dd, 1H); δ=4.815 ppm (dd, 1H).

According to the $^1$H NMR spectrum (400 MHz) the product is a 48:52 mixture of diastereomers.

EXAMPLE 46

N-[2-(4-Carbomethoxymethoxyphenyl)ethyl]-2-hydroxy-2-(2-methyl-thiazol-4-yl)ethanamine hydrochloride (a)

N-(4-Hydroxyphenyl-acetyl)-2-hydroxy-2-(2-methyl-thiazol-4-yl)ethanamine 3.16 g (20 mmol) of 2-Hydroxy-2-(2-methyl-thiazol-4-yl)ethanamine are dissolved in 80 ml of absolute tetrahydrofuran and, successively, 3.84 g (20 mmol) of 4-hydroxy-phenylacetic acid, 6.3 g (24 mmol) of triphenylphosphine, 5.6 ml (40 mmol) of triethylamine and 2 ml (20 mmol) of carbon tetrachloride are added. After stirring overnight, the mixture is concentrated, the residue is taken up in 2N hydrochloric acid and the solution is extracted three times with methylene chloride. The aqueous phase is then adjusted to pH 7 with 2N sodium hydroxide solution and evaporated to dryness. The residue from evaporation is extracted by boiling several times with a mixture of chloroform/methanol (1:1). The extracts are concentrated, and the residue is purified on a silica gel column using ethyl acetate/methanol=50:1 as eluant.

Yield: 4.4 g of oil (75.9% of theory),
Calculated: C 57.51; H 5.52; N 9.58. Found: C 57.63; H 5.59; N 9.41.

(b)

N-[2-(4-Hydroxyphenyl)ethyl]-2-hydroxy-2-(2-methyl-thiazol-4-yl)ethanamine hydrochloride 4.2 g (14.4 mmol) of N-(4-Hydroxyphenyl-acetyl)-2-hydroxy-2-(2-methyl-thiazol-4-yl)ethanamine are dissolved in 30 ml of absolute tetrahydrofuran, and the solution is added dropwise to a suspension, which is boiling under reflux, of 1.37 g (36 mmol) of lithium aluminium hydride in 30 ml of absolute tetrahydrofuran. After 1 hour the mixture is cooled, decomposed with 2N sodium hydroxide solution and concentrated. The residue is then taken up in 20 ml of 2N hydrochloric acid, and the solution is made alkaline with aqueous ammonia. After renewed concentration, the residue is extracted with hot chloroform/methanol=10:1. The extracts are concentrated and purified on a silica gel column using ethyl acetate/methanol=4:1 as eluant. Subsequently the hydrochloride is precipitated in ethyl acetate using ethereal hydrochloric acid.

Yield: 760 mg (19% of theory),
M.p.: 110°-113° C.
Calculated: C 53.41; H 6.08; N 8.90; Cl 11.26. Found: C 53.12; H 6.04; N 8.80; Cl 11.31.

(c)

N-[2-(4-Carbomethoxymethoxyphenyl)ethyl]-2-hydroxy-2-(2-methyl-thiazol-4-yl)ethanamine hydrochloride 100 mg (2.1 mmol) of Sodium hydride dispersion (50% in paraffin oil) are added to 280 mg (1 mmol) of N-[2-(4-hydroxyphenyl)ethyl]-2-hydroxy-2-(2-methyl-thiazol-4-yl)ethanamine hydrochloride dissolved in 7 ml of absolute dimethyl formamide. After stirring at room temperature for 15 minutes, the solution of 153 mg (1 mmol) of ethyl bromoacetate in 3 ml of absolute dimethylformamide is rapidly added dropwise. The mixture is then stirred overnight, 20 ml of saturated sodium bicarbonate solution are added, and extraction with methylene chloride is carried out. The extracts are dried, concentrated and, after dissolution in ether/methanol, the hydrochloride is precipitated with ethereal hydrochloric acid.

Yield: 20 mg (21% of theory),
M.p.: 163°-165° C. (decomp.)
Calculated: C 52.78; H 5.99; N 7.24. Found: C 52.41; H 5.76; N 7.32.

EXAMPLE 47

N-[2-(4-Carbomethoxymethoxyphenyl)ethyl]-2-(2-trifluoromethyl-thiazol-4-yl)morpholine (a)

N-[2-(4-Methoxy-phenyl)ethyl]-2-(2-trifluoromethyl-thiazol-4-yl)morpholine

Prepared analogously to Example 32 by reaction of N-(2-hydroxyethyl)-2-(4-methoxyphenyl)ethanamine with 2-trifluoromethyl-4-bromoacetyl-thiazole followed by reduction with triethylsilane.

Yield: 24% of theory, oil,
Calculated: C 54.82; H 5.14; N 7.52; S 8.61. Found: C 55.00; H 5.24; N 7.42; S 8.86.

(b)

N-[2-(4-Carbomethoxymethoxyphenyl)ethyl]-2-(2-trifluoromethyl-thiazol-4-yl)morpholine 0.6 g (1.6 mmol) of N-[2-(4-Methoxyphenyl)ethyl]-2-(2-trifluoromethyl-thiazol-4-yl)morpholine are heated on a steam bath with 6 ml of 48% strength aqueous hydrobromic acid for 3 hours. The mixture is then concentrated, toluene is added, and the mixture is again evaporated to dryness. The foamy residue is boiled under reflux in 15 ml of acetone with 1.2 g (8.7 mmol) of potassium carbonate and 0.3 ml (1.65 mmol) of methyl bromoacetate for 1 hour. The mixture is then filtered, the filtrate is concentrated, and the residue is purified on a silica gel column using toluene/acetone=4:1.

Yield: 0.5 g (72% of theory),
Calculated: C 53.01; H 4.92; N 6.51; S 7.45. Found: 53.07; H 4.88; N 6.72; S 7.62.

EXAMPLE 48

N-[2-(4-Carboethoxymethoxyphenyl)-1-methylethyl]-2-(2-trifluoromethyl-thiazol-4-yl)morpholine (a)

N-[2-(4-Hydroxyphenyl)-1-methylethyl]-2-(2-trifluoromethylthiazol-4-yl)morpholine Prepared by analogy to Example 22 by reaction of 2-trifluoromethyl-4-bromoacetyl-thiazole with N-[2-(4-hydroxyphenyl)-1-methylethyl]-2-hydroxyethanamine followed by purification of the base on a silica gel column using chloroform/ethyl acetate=3:1 as eluant.

Yield: 29% of theory,
Calculated: C 54.83; H 5.14; N 7.52. Found: C 53.83; H 5.07; N 6.93.

According to the $^1$H-NMR spectrum (400 MHz) the product is a 50:50 mixture of the diastereomers.

(b)

N-[2-(4-Carboethoxymethoxyphenyl)-1-methylethyl]-2-(2-trifluoromethyl-thiazol-4-yl)morpholine 280 mg (0.75 mmol) of N-[2-(4-hydroxyphenyl-1-methylethyl]-2-(2-trifluoromethyl-thiazol-4-yl)morpholine are boiled under reflux for 6 hours with 101 mg (0.82 mmol) of ethyl chloroacetate and 113 mg (0.82 mmol) of potassium carbonate in 2 ml of anhydrous acetone. The mixture is then filtered with suction, the residue is washed twice with acetone, and the filtrate is concentrated. The crude base is purified on a silica gel column using chloroform/methanol=20:1 as eluant.

Yield: 50% of theory,

Calculated: C 55.01; H 5.50; N 6.11; S 6.99. Found: C 55.48; H 5.62; N 5.85; S 6.62.

EXAMPLE 49

N-[2-(4-Carbomethoxymethoxyphenyl)-1-methylethyl]-2-(2-isopropyl-thiazol-4-yl)morpholin-6-one hydrochloride 0.194 g (1.27 mmol) of methyl bromoacetate, 0.175 g (1.27 mmol) of potassium carbonate and a small crystal of potassium iodide are successively added to a solution of 0.50 g (1.27 mmol) of N-[2-(4-methoxy-carbonylmethoxyphenyl)-1-methylethyl]-2-hydroxy-2-(2-isopropyl-thiazol-4-yl)ethanamine in 5 ml of anhydrous dimethyl formamide. After stirring at 20° C. for 4 hours, the dimethyl formamide is removed by distillation in vacuo. and the residue is partitioned between chloroform and water. The dried and filtered chloroform extract is concentrated in vacuo and the residue is purified by column chromatography on silica gel (toluene/acetone=4/1).

Yield: 0.20 g (36% of theory), viscous oil.

According to the $^1$H-NMR spectrum (400 MHz, CDCl$_3$/CD$_3$OD) the product is a 50:50 mixture of the diastereomers.

$\delta$=5.59 ppm (dd, =C$\underline{H}$—O—CO—); $\delta$=5.62 ppm (dd, =C$\underline{H}$—O—CO—).

A hydrochloride is obtained in the form of a foam by treatment of the base with hydrogen chloride/ether followed by drying at 20° C. and 0.1 Torr.

Melting range: 40°-50° C.

Calculated: (x 1.2 HCl) C 54.44; H 6.27; Cl 8.77. Found: C 54.70; H 6.57; Cl 8.48.

EXAMPLE 50

N-[2-(4-Carbomethoxymethoxyphenyl)-1-methylethyl]-2-(2-isopropyl-thiazol-4-yl)morpholine (a)

N-[2-(4-Carbomethoxymethoxyphenyl)-1-methylethyl]-2-(2-isopropyl-thiazol-4-yl)morpholin-5-one 0.60 ml (7.89 mmol) of chloroacetyl chloride is added dropwise to a stirred solution of 3.10 g (7.89 mmol) of N-[2-(4-methoxycarbonylmethoxyphenyl)-1-methylethyl-[-2-hydroxy-2-(2-isopropyl-thiazol-4-yl)-ethanamine and 1.10 ml (7.89 mmol) of triethylamine in 20 ml of chloroform at 25° C. internal temperature. After the mixture has stood overnight at 20° C., it is concentrated in vacuo, and the resudue is dissolved in 30 ml of anhydrous dimethyl formamide. To this is added 0.888 g (15.78 mmol) of a 55% dispersion of sodium hydride in oil, during which brief foaming is observed. The mixture is stirred at 20° C. for 3 hours, concentrated in vacuo. and the residue is partitioned between water and ether. The ether solution is dried, filtered and concentrated in vacuo, and the oily residue is purified on silica gel (toluene/acetone=4:1).

Yield: 1.40 g (41% of theory),

Melting range: 60°-70° C.

Calculated: C 61.10; H 6.53; N 6.48; S 7.41. Found: C 61.20; H 6.57; N 6.77; S 7.58.

According to the $^1$H-NMR spectrum (400 MHz, CDCl$_3$) the product is a 50:50 mixture of the diastereomers.

$\delta$=4.72 ppm (dd, =C$\underline{H}$—O—); $\delta$=4.85 ppm (dd, =C$\underline{H}$—O—).

(b)

N-[2-(4-Carbomethoxymethoxyphenyl)-1-methylethyl]-2-(2-isooropyl-thiazol-4-yl)morpholine 0.200 g (0.462 mmol) N-[2-(4-carbomethoxymethoxyphenyl)-1-methylethyl]-2-(2-isopropyl-thiazol-4-yl)-morpholin-5-one is added to 0.425 ml (4.56 mmol) of phosphorus oxychloride. After the mixture has been stirred at 20° C. for 15 minutes it is concentrated in vacuo, and the residue is dissolved in 4 ml of 1,2-dimethoxyethane. After addition of 0.052 g (1.39 mmol) of sodium borohydride and stirring overnight at 20° C., the mixture is concentrated in vacuo and the residue is partitioned between chloroform and water. After the chloroform solution has been dried and filtered and concentrated it is heated with hydrogen chloride solution at 100° C. for one hour. After concentration in vacuo the residue is partioned between chloroform and aqueous sodium carbonate solution, and the chloroform extract is purified on silica gel (toluene/acetone=3:1).

Yield: 0.028g (14.5% of theory),

Calculated: Molecular peak m/e=418; Found: Base peak m/e=239.

According to the $^1$H-NMR spectrum (400 MHz, CDCl$_3$/CD$_3$OD) the product is a 50:50 mixture of the diasetereomers.

$\delta$=4.72 ppm (dd, =C$\underline{H}$—O—); $\delta$=4.74 ppm (dd, =C$\underline{H}$—O—).

EXAMPLE 51

N-[2-Carbomethoxyethoxyphenyl)-1-methylethyl]-2-hydroxy-2-(2-isopropyl-thiazol-4-yl)ethanamine dihydrochloride Prepared by analogy to Example 13 by reaction of 2-hydroxy-2-(2-isopropyl-thiazol-4-yl)ethanamine with 1-(4-carbomethoxyethoxyphenyl)-propan-2-one followed by purification of the base by column chromatography on silica gel (chloroform/methanol=10:1).

Yield: 89% of theory,

Calculated: Molecular peak m/e=418; Found: Base peak m/e=239.

$^1$H-NMR spectrum (400 MHz, CDCl$_3$): $\delta$=4.80 ppm (dd, =C$\underline{H}$—OH); $\delta$=4.84 ppm (dd, =C$\underline{H}$—OH).

According to the $^1$H-NMR spectrum the product is an approximately 50:50 mixture of the diastereomers.

To convert the base into the dihydrochloride it it treated with hydrogen chloride/diethyl ether. After the ether has been evaporated off in vacuo the product is dried at 20° C. and 0.1 Torr for 3 days.

Melting range: 55°-70° C.

Calculated: C 51.61; H 6.49; N 6.02; S 6.88. Found: C 51.40; H 6.64; N 5.86; S 6.88.

EXAMPLE 52

N-[2-(4-Carbomethoxymethoxyphenyl)-1-methylethyl]-2-hydroxy-2-(2-propylthiazol-4-yl)ethanamine dihydrochloride Prepared by analogy to Example 13 by reaction of 2-hydroxy-2-(2-propyl-thiazol-4-yl)ethanamine with 1-(4-carbomethoxymethoxyphenyl)propan-2-one followed by purification of the base by column chromatography on silica gel (chloroform/methanol=10:1).

Yield: 52% of theory,
$^1$H-NMR spectrum (400 MHz, CDCl$_3$/CD$_3$OD): δ=4.72 ppm (dd, =C$\underline{\text{H}}$—OH); δ=4.78 ppm (dd, =C$\underline{\text{H}}$—OH).

According to the $^1$H-NMR spectrum the product is an approximately 50:50 mixture of the diastereomers.

To convert the viscous base into the dihydrochloride it is treated with hydrogen chloride/methanol. After the methanol has been evaporated off in vacuo, the product is dried first at 0.1 Torr and 40°–50° C. and then overnight at 35° C. and 0.1 Torr over phosphorus pentoxide.

Melting range: 50°–70° C.
Calculated: C 51.61; H, 6.49; N 6.02; S 6.88.
Found: C 51.38; H 6.13; N 6.28; S 7.00.

EXAMPLE 53

N-[2-(4-Carboxymethoxyphenyl)-1-methylethyl]-2-hydroxy-2-(2-propyl-thiazol-4-yl)ethanamine Prepared by analogy to Example 16 by reaction of N-[2-(4-carbomethoxymethoxyphenyl)-1-methylethyl]-2-hydroxy-2-(2-propyl-thiazolyl-4-yl)ethanamine in methanol and 1N sodium hydroxide solution. After the mixture has been neutralised with 1N hydrochloric acid it is concentrated in vacuo. and the residue is then partitioned between chloroform and water. The chloroform extract is dried over sodium sulphate, filtered and evaporated in vacuo. The residue from evaporation provides on trituration with ether a powdery solid which is dried at 50° C. and 0.1 Torr for 6 hours.

Yield: 79% of theory,
Melting range: 79°–85° C.
Calculated: (x 0.75 H$_2$O): C 58.23; H 7.07; N 7.15; S 8.18. Found: C 58.10; H 6.75; N 6.91; S 8.56.

According to the $^1$H-NMR spectrum (400 MHz, CDCl$_3$/CD$_3$OD) the product is a 50:50 mixture of the diastereomers.

δ=5.14 ppm (dd, =C$\underline{\text{H}}$—OH); δ=5.17 ppm (dd, =C$\underline{\text{H}}$—OH).

EXAMPLE 54

N-[2-(4-Carboxymethoxyphenyl)-1-methylethyl]-2-hydroxy-2-(2-isopropyl-thiazol-4-yl)ethanamine hydrochloride Prepared by analogy to Example 16 by reaction of N-[2-(4-carbomethoxymethoxyphenyl)-1-methylethyl]-2-hydroxy-2-(2-isopropyl-thiazolyl-4-yl)ethanamine in methanol and 1N sodium hydroxide solution. After 1N hydrochloric acid has been added until pH 6 has been reached, the mixture is concentrated in vacuo, and the residue is partitioned between chloroform and water. The dried and filtered chloroform extract is evaporated in vacuo. Trituration of the residue from evaporation with ether results in a foam-like solid which still contains about 5% chloroform even after drying for several hours at 30° C. and 0.1 Torr over phosphorous pentoxide.

Yield: 22% of theory,
Melting range: 80°–90° C.
Calculated: (+5% CHCl$_3$): C 54.35; H 6.48; N 6.66; S 9.69. Found: C 54.19; H 6.27; N 6.53; S 9.26.

According to the $^1$H-NMR spectrum (400 MHz, d$_6$-DMSO) the product is an approximately 50:50 mixture of the diastereomers.

δ=5 00 ppm (dd, =C$\underline{\text{H}}$—OH); δ=5.04 ppm (dd, =C$\underline{\text{H}}$—OH).

EXAMPLE 55

N-[2-(4-Methoxyphenyl)-1-methylethyl]-2-hydroxy-2-(2-trifluoromethyl-thiazol-4-yl)ethanamine hydrochloride Prepared by analogy to Example 13 by reaction of 2-hydroxy-2-(2-trifluoromethyl-thiazolyl-4-yl)-ethanamine with 4-methoxyphenyl-propan-2-one, followed by purification of a base on a silica gel column using ethyl acetate/methanol=92:8 as eluant and precipitation of the hydrochloride with ethereal hydrochloric acid.

Yield: 57% of theory,
Melting range: 147°–149° C. (decomp.)
Calculated: C 48.42; H 5.08; N 7.06; Cl 8.93. Found: C 48.65; H 5.39; N 7.11; Cl 9.19.

According to the $^1$H-NMR spectrum (400 MHz) the product is a 1:1 mixture of the diastereomers.

EXAMPLE 56

3-[2-(4-Methoxyphenyl)-1-methylethyl]-5-(2-trifluoromethyl-thiazol-4-yl)-2-oxazolidine carboxylate Prepared by analogy to Example 18 by reaction of N-[2-(4-methoxyphenyl)-1-methylethyl]-2-hydroxy-2-(2-trifluoromethyl-thiazol-4-yl)ethanamine with methyl glyoxylate followed by purification of the base on a silica gel column using chloroform/petroleum ether/ethyl acetate=5:4.5:0.5 as eluant.

Yield: 25% of theory,
Calculated: C 53.02; H 4.92; N 6.51; Cl 7.45. Found: C 53.29; H 4.86; N 6.32; Cl 7.54.

EXAMPLE 57

N-[2-(4-Hydroxyphenyl)-1-methylethyl]-2-hydroxy-2-(2-trifluoromethylthiazol-4-yl)ethanamine Prepared by analogy to Example 13 by reaction of 2-hydroxy-2-(2-trifluoromethyl-thiazol-4-yl)ethanamine with 4-hydroxyphenyl-propan-2-one followed by purification of the base on a silica gel column using chloroform/methanol=9:1 as eluant.

Yield: 63% of theory,
Melting point: from 77° C., clear melt from 97° C.
Calculated: C 52.01; H 4.95; N 8.09; S 9.26. Found: C 52.05; H 4.98; N 8.17; S 9.19.

According to the $^1$H-NMR spectrum (400 MHz) the product is a 1:1 mixture of the diastereomers.

EXAMPLE 58

N-[2-(4-Hydroxyphenyl)-1-methylethyl]-2-hydroxy-2-(2-methylthiazol-4-yl)ethanamine Prepared by analogy to Example 13 by reaction of 2-hydroxy-2-(2-methyl-thiazol-4-yl)ethanamine with 4-hydroxyphenyl-propan-2-one followed by purification of the base on a silica gel column using chloroform/methanol/ammonia=9:1:1 as eluant.

Yield: 52% of theory,
Melting point: 146°–154° C.
Calculated: C 61.62; H 6.89; N 9.58; S 10.97. Found: C 61.96; H 6.90; N 9.65; S 11.24.

According to the $^1$H-NMR spectrum (400 MHz) the product is a 70:30 mixture of the diasteromers.

EXAMPLE 59

N-[2-(4-Methoxyphenyl)-1-methylethyl]-2-(2-trifluoromethylthiazol-4-yl)morpholine Prepared by analogy to Example 13 by reaction of 2-(2-trifluoromethyl-thiazol-4-yl)morpholine with 4- methoxyphenyl-propan-2-one followed by purification of the base on a silica gel column using chloroform-/ethyl acetate=9:1 as eluant.

Yield: 80% of theory,
Melting point: 146°–154° C.
Calculated: C 55.95; H 5.48; N 7.25. Found: C 56.09; H 5.62; N 6.83.

According to the $^1$H-NMR spectrum (400 MHz) the product is a 50:50 mixture of the diasteromers.

EXAMPLE 60

Methyl 3-[2-(4-(2-carbomethoxy-1-methylethenyl)phenyl)-1-methylethyl]-5-(2-trifluoromethyl-thiazol-4-yl)-2-oxazolidine carboxylate Prepared by analogy to Example 18 by reaction of N-[2-(4-(2-carbomethoxy-1-methylethenyl)phenyl)-1-methyl-ethyl]-2-hydroxy-2-(2-trifluoromethyl-thiazol-4-yl)ethanamine with methyl glyoxylate followed by purification of the base on a silica gel column using chloroform/petroleum ether/ethyl acetate=5:4.5:0.5 as eluant.

Yield: 66% of theory,
Calculated: C 55.41; H 5.05; N 5.62; S 6.43. Found: C 55.3; H 5.23; N 4.96; S 6.64.

$^1$H-NMR spectrum (CDCl$_3$/CD$_3$OD):

$\delta$=5.10 ppm (s, 2H); $\delta$=5.23 ppm (s, 1H); $\delta$=5.27 ppm (s, 1H).

According to the $^1$H-NMR spectrum (400 MHz) the product is a 1:1:1:1 mixture of the diasteromers.

EXAMPLE 61

Methyl 3-[2-(4-Hydroxyphenyl)-1-methylethyl]-5-(2-trifluoromethylthiazol-4-yl)-2-oxazolidine carboxylate Prepared by analogy to Example 18 by reaction of N-[2-(4-hydroxyphenyl)-2-methylethyl]-2-hydroxy-2-(2-trifluoromethyl-thiazol-4-yl)ethanamine with methyl glyoxylate, followed by purification of the base on a silica gel column using chloroform/ethyl acetate=9:1 as eluant and precipitation of the hydrochloride with ethereal hydrochloric acid.

Yield: 37% of theory,
Melting point: from 158° C. (decomp.)
Calculated: C 47.74; H 4.45; N 6.19; S 7.08; Cl 7.88. Found: C 47.49; H 4.72; N 6.38; S 7.22; Cl 7.98.

EXAMPLE 62

Methyl 3-[2-(4-(2-Carbomethoxy-1-methylethenyl)phenyl)-1-methylethyl]-5-(2-methyl-thiazol-4-yl)-2oxazolidine carboxylate Prepared by analogy to Example 18 by reaction of N-[2-(4-(2-carbomethoxy-1-methylethenyl)phenyl)-1-methylethyl]-2-hydroxy-2-(2-methyl-thiazol-4-yl)ethanamine with methyl glyoxylate, followed by purification of the base on a silica gel column using petroleum ether/ethyl acetate=7:3 as eluant.

Yield: 18% of theory, oil,
Calculated: C 62.14; H 6.35; N 6.30; S 7.21. Found: C 61.90; H 6.60; N 6.34; S 7.03.

EXAMPLE 63

Methyl 3-[2-(4-hydroxyphenyl)-1-methylethyl]-5-(2-methyl-thiazol-4-yl)-2-oxazolidine carboxylate Prepared by analogy to Example 18 by reaction of N-[2-(4-hydroxyphenyl)-1-methylethyl]-2-hydroxy-2-(2-methyl-thiazol-4-yl)ethanamine with methyl glyoxylate, followed by purification of the base on a silica gel column using ether/petroleum ether=8:2 as eluant.

Yield: 25% of theory, oil,
Calculated: C 59.65; H 6.12; N 7.73; S 8.85. Found: C 60.00; H 5.98; N 7.23; S 8.97.

EXAMPLE 64

N-[2-(4-Carbomethoxymethoxyphenyl)-1-methylethyl]-2-(2-trifluoromethyl-thiazol-4-yl)morpholin-6-one 2.1 g (0.0005 mol) of N-[2-(4-carbomethoxymethoxyphenyl-1-methylethyl)-2-hydroxy-2-(2-trifluoromethylthiazol-4-yl)ethanamine are dissolved in 70 ml of acetone, and while stirring 5 ml of methyl bromoacetate and 5 g of potassium carbonate are added. The mixture is initially stirred at room temperature for 16 hours then heated under reflux for 4 hours. The inorganic products are removed by filtration, the solvent is removed by distillation, and the resulting residue is purified on a silica gel column using toluene/ethyl acetate=8.1:1.5 as eluant.

Yield: 0.8 g of oil (35% of theory),
Calculated: C 52.39, H 4.62; N 6.11. Found: C 52.50; H 4.51; N 5.85.

$^1$H-NMR spectrum (400 MHz) (CDCl$_3$/CD$_3$OD):
$\delta$=7.596 ppm (d, 1H); $\delta$=7.686 ppm (d, 1H).

According to this, the product is a 50:50 mixture of the diastereomers.

EXAMPLE 65

N-[2-(4-Carboethoxymethoxyphenyl)-1-methylethyl]-2-(2-trifluoromethyl-thiazol-4-yl)morpholine hydrochloride 0.5 g (0.0012 mol) of N-[2-(4-carboxymethoxyphenyl)-1-methylethyl]-2-(2-trifluoromethyl-thiazol-4-yl)morpholine is dissolved in 150 ml of chloroform and, while stirring, 2 ml ethanol and 0.25 g of concentrated sulphuric acid are added, and the the mixture is heated to reflux with a water trap for one hour. The mixture is then cooled, ice-water is added, the mixture is made alkaline with ammonia and the phases are separated. The aqueous phase is then extracted again by shaking with chloroform, and the organic phase is dried over sodium sulphate, filtered and evaporated to dryness. The resulting residue is dissolved in ether, ethereal hydrochloric acid is added, the mixture is evaporated to dryness, and the residue is triturated with acetone and filtered off with suction.

Yield 0.37 g (63% of theory),
Melting point: 122°–123° C.
Calculated: C 50.95; H 5.30; N 5.66. Found: C 50.85; H 5.49; N 5.68.

According to the $^1$H-NMR spectrum (400 MHz) the product is a 50:50 mixture of the diasteromers.

EXAMPLE 66

N-[2-(4-Carbomethoxymethoxyphenyl)-1-methylethyl]-2-hydroxy-2-(2-methyl-thiazol-5-yl)ethanamine dihydrochloride Prepared by analogy to Example 13 by reaction of 2-hydroxy-2-(2-methyl-thiazol-5-yl)ethanamine with 1-(4-carbomethoxymethoxyphenyl)propan-2-one, purification of the base on a silica gel column using ethyl acetate/ethanol=8:2 as eluant and then precipitation of the dihydrochloride using ethereal hydrochloric acid.

Yield 32% of theory,
Melting point: 190°–192° C.
Calculated: C 49.43; H 5.99; N 6.40. Found: C 49.43; H 5.90; N 6.49.

According to the $^1$H-NMR spectrum (400 MHz) the product is an approximately 50:50 mixture of the diastereomers.

EXAMPLE 67

N-[2-(4-Carbomethoxymethoxyphenyl)-1-methylethyl]-2-hydroxy-2-(2-trifluoromethyl-thiazol-4-yl)ethanamine (Diastereomer B)

Prepared by analogy to Example 13 by reaction of 2-hydroxy-2-(2-trifluoromethyl-thiazol-4-yl)ethanamine with 1-(4-carbomethoxymethoxyphenyl)propan-2-one and sodium cyanoborohydride in methanol (reaction time: 5 hours) followed by purification on a silica gel column using methylene chloride/methanol=20:1. This results in a 50:50 diastereomer mixture of the base. This is recrystallised from a mixture of ether/ethyl acetate=65:10. The mother liquor resulting from this is mixed with ethereal hydrochloric acid, and the mixture is evaporated to dryness. The residue resulting from this is recrystallised from a mixture of ether/ethyl acetate/methanol=100:60:1. The mother liquor obtar,ned after the crystals have been removed by filtration is evaporated to dryness, and the base is liberated by shaking with alkali and methylene chloride and purified on a silica gel column using methylene chloride/methanol=20:1 as eluant. This results in diastereomer B as an oil approximately 92–94% pure.

Yield: 4% of theory,
Calculated: C 54.66; H 5.06; N 6.70. Found: C 54.43; H 5.13; N 6.88.
$^1$H-NMR spectrum (400 MHz) (CDCl$_3$/CD$_3$OD): δ=7.56 ppm (s, 1H).

EXAMPLE 68

N-[2-(4-Carbomethoxymethoxyphenyl)-1-methylethyl]-2-hydroxy-2-(2-trifluoromethyl-thiazol-4-yl)ethanamine (Diastereomer A)

Prepared by analogy to Example 13 by reaction of 2-hydroxy-2-(2-trifluoromethyl-thiazol-4-yl)ethanamine with 1-(4-carbomethoxymethoxyphenyl)propan-2-one and sodium cyanoborohydride in methanol=- (reaction time: 5 hours) followed by purification on a silica gel column using methylene chloride/methanol 20:1. This results in an approximately 50:50 diastereomer mixture of the base. This is recrystallised from a mixture of ether/ethyl acetate=65:10, and twice more from ethyl acetate. This results in diastereomer A in 98–99% purity.

Yield: 14% of theory,
Melting point: 104°–105° C.
Calculated: C 51.66; H 5.06; N 6.70. Found: C 51.90; H 4.82; N 6.82.
$^1$H-NMR spectrum (400 MHz) (CDCl$_3$/CD$_3$OD): δ=7.59 ppm (s, 1H).

EXAMPLE 69

N-[2-(4-Carboxymethoxyphenyl)-1-methylethyl]-2-(2-trifluoromethyl-thiazol-4-yl)morpholine (Diastereomer A)

Prepared by analogy to Example 16 by reaction of N-[2-(4-carbomethoxymethoxyphenyl)-1-methylethyl]-2-(2-trifluoromethyl-thiazol-4-yl)morpholine (diastereomer A) in methanol with 1N sodium hydroxide solution. After the mixture has been neutralised with 1N hydrochloric acid it is extracted by shaking with methylene chloride, the extract is evaporated to dryness, and the remaining residue is triturated with petroleum ether and is filtered off with suction.

Yield: 96% of theory,
Melting point: from 70° C. (sintering)
Calculated: C 53.01; H 4.92; N 6.51. Found: C 53.15; H 4.97; N 6.53.
$^1$H-NMR spectrum (400 MHz) (CDCl$_3$/CD$_3$OD): δ=7.757 ppm (s, 1H).

EXAMPLE 70

N-[2-(4-Carboxymethoxyphenyl)-1-methylethyl]-2-(2-trifluoromethyl-thiazol-4-yl)moroholine (Diastereomer B)

Prepared by analogy to Example 16 by reaction of N-[2-(4-carbomethoxymethoxyphenyl)-1-methylethyl]-2-(2-trifluoromethyl-thiazol-4-yl)morpholine (diastereomer B) in methanol with 1N sodium hydroxide solution. After the mixture has been neutralised with 1N hydrochloric acid it is extracted by shaking with methylene chloride, the extract is evaporated to dryness, and the remaining residue is triturated with petroleum ether and is filtered off with suction.

Yield: 88% of theory,
Melting point: from 70° C. (sintering)
Calculated: C 53.01; H 4.92; N 6.51. Found: C 53.19; H 5.19; N 6.48.
$^1$H-NMR spectrum (400 MHz) (CDCl$_3$/CD$_3$OD): δ=7.786 ppm (s, 1H).

According to this the compound still contains about 6–7% of diastereomer A.

EXAMPLE 71

N-[2-(4-(2-Hydroxyethoxy)phenyl)-1-methylethyl]-2-(2-trifluoromethyl-thiazol-4-yl)morpholine (Diastereomer A) 1 g (0.0022 Mol) of N-[2-(4-carbomethoxymethoxyphenyl)-1-methylethyl]-2-(2-trifluoromethyl-thiazol-4-yl)morpholin-5-one (diastereomer A) is dissolved in 6 ml of absolute tetrahydrofuran. At room temperature 15 ml (0.015 Mol) of a one molar solution of diborane in tetrahydrofuran is added dropwise within 15–20 minutes. During this the solution heated up to about 35°–40° C. After 30 minutes the mixture is evaporated to dryness and the remaining residue is dissolved in 40 ml of methanol and 2 ml of concentrated hydrochloric acid, and the mixture is left to stand for 30 minutes. While cooling in ice, the mixture is made alkaline with ammonia and is extracted several times by shaking with methylene chloride. The organic phase is dried over sodium sulphate and the base is purified on a silica gel column using toluene/ethyl acetate=7.5:2.5 as eluant.

Yield: 0.28 g (31% of theory),
Melting point: 76°–78° C.
Calculated: C 54.79; H 5.57; N 6.73. Found: C 54.90; H 5.71; N 6.54.
$^1$H-NMR spectrum (400 MHz) (CDCl$_3$/CD$_3$OD): $\delta$=7.614 ppm (s, 1H).

EXAMPLE 72

N-[2-(4-Carboxymethoxyphenyl)-1-methylethyl]-2-hydroxy-2-(2-trifluoromethyl-thiazol-4-yl)ethanamine (Diastereomer A)

Prepared by analogy to Example 16 by reaction of N-[2-(4-carbomethoxymethoxyphenyl)-1-methylethyl]-2-(2-trifluoromethyl-thiazol-4-yl)ethanamine (diastereomer A) in methanol with 1N sodium hydroxide solution. After the mixture has been neutralised with 1N hydrochloric acid it is extracted by shaking with methylene chloride, the extract is evaporated to dryness, and the remaining residue is triturated with petroleum ether and filtered off with suction.

Yield: 89% of theory,
Melting point: 119°–121° C.
Calculated: C 50.49; H 4.74; N 6.93. Found: C 50.62; H 4.69; N 6.90.
$^1$H-NMR spectrum (400 MHz) (CDCl$_3$/CD$_3$OD): $\delta$=7.771 ppm (s, 1H).

EXAMPLE 73

N-[2-(4-Carboxymethoxyphenyl)-1-methylethyl]-N-(2-hydroxyethyl)-2-hydroxy-2-(2-trifluoromethyl-thiazol-4-yl)ethanamine Prepared by analogy to Example 16 by reaction of N-[2-(4-carbomethoxymethoxyphenyl)-1-methylethyl]-N-(2-hydroxyethyl)-2-hydroxy-2-(2-trifluoromethyl-thiazol-4yl)ethanamine in methanol with 1N sodium hydroxide solution. After the mixture has been neutralised with 1N hydrochloric acid it is evaporated to dryness, treated with 10 ml of ethanol, and the inorganic residues are removed by filtration. The ethanol phase is diluted with 60 ml of methylene chloride and again filtered. The mother liquor is evaporated to dryness, and the residue is triturated with ether and filtered off with suction.

Yield: 90% of theory,
Melting point: 83°–85° C.
Calculated: C 50.88; H 5.17; N 6.25. Found: C 50.70; H 5.44; N 6.11.

According to the $^1$H-NMR spectrum (400 MHz) the product is an approximately 60:40 diastereomer mixture.

EXAMPLE 74

N-[2-(4-Carbomethoxymethoxyphenyl)-1-methylethyl]-2-(2-trifluoromethyl-thiazol-4-yl)morpholine (Diastereomer A)

(a)

N-[2-(4-Carbomethoxymethoxyohenyl)-1-methylethyl]-2-(2-trifluoromethyl-thiazol-4-yl)morpholin-5-one (Diastereomer A)

1.2 g (0.0029 mol) of N-[2-(4-Carbomethoxymethoxyphenyl)-1-methylethyl]-2-hydroxy-2-(2-trifluoromethyl-thiazol-4-yl)ethanamine (diastereomer A) are dissolved in 12 ml of methylene chloride, and the solution is cooled to 12° C. and 0.4 ml (0.0029 mol) of triethylamine is added. While stirring, 0.22 ml (0.0029 mol) of chloroacetyl chloride is added dropwise. The temperature rises to 24° C. during this. After 30 minutes the organic phase is extracted by shaking with water, dried over sodium sulphate and evaporated to dryness. The oil which results from this is taken up in 12 ml of dimehylformamide and, while stirring, reacted at 22°–24° C. with 130 mg of 50% sodium hydride dispersion in oil. After one hour a further 90 mg of 50% sodium hydride dispersion are added to complete the reaction. After a total of 1.5 hours the mixture is neutralised with ethereal hydrochloric acid, and 100 ml of methylene chloride are added. The organic phase is extracted by shaking with water, and the latter is extracted a further 2 x with methylene chloride. After the organic phases have been dried over sodium sulphate they are evaporated to dryness. The resulting oil is purified on a silica gel column using toluene/ethyl acetate=6:4 as eluant.

Yield 1.2 g (90% of theory).

(b)

N-[2-(4-Carbomethoxymethoxyphenyl)-1-methylethyl]-2-(2-trifluoromethyl-thiazol-4-yl)morpholine (Diastereomer A)

1.2 g (0.0026 mol) of N-[2-(4-Carbomethoxymethoxyphenyl)-1-methylethyl]-2-(2-trifluoromethyl-thiazol-4-yl)morpholin-5-one (diastereomer A) are dissolved in 10 ml of absolute tetrahydrofuran at 22° C. Three portions of 2.8 ml (0.0028 mol) of a 1 molar solution of diborane in tetrahydrofuran are added dropwise to this solution at intervals of 30 minutes in each instance. The mixture is evaporated to dryness after 1.5 hours. The resulting residue is taken up in 80 ml of methanol and the solution is left to stand at room temperature for 16 hours. It is again evaporated to dryness and the resulting residue is taken up in methylene chloride, and the organic phase is extracted with a cold aqueous ammonia solution. The methylene chloride phase is extracted 2 x with water, and the organic phase is dried over sodium sulphate and concentrated. The resulting residue is purified on a silica gel column using toluene/ethyl acetate=8:2 as eluant. This results in a colourless oil.

Yield: 0.8 g (69.3% of theory),
Calculated: C 54.04; H 5.22; N 6.30. Found: C 54.20; H 5.53; N 6.41.
$^1$H-NMR spectrum (400 MHz) (CDCl$_3$/CD$_3$OD): $\delta$=4.807 ppm (dd, 1H).

EXAMPLE 75

N-[2-(4-Carbomethoxymethoxyphenyl)-1-methylethyl]-2-(2-trifluoromethyl-thiazol-4-yl)morpholine (Diastereomer B)

(a)

N-[2-(4-Carbomethoxymethoxyphenyl)-1-methylethyl]-2-(2-trifluoromethyl-thiazol-4-yl)morpholin-5-one (Diastereomer B)

Prepared by analogy to Example 74a by reaction of N-[2-(4-Carbomethoxymethoxyphenyl)-1-methylethyl]-2-hydroxy-2-(2-trifluoromethyl-thiazol-4-yl)ethanamine (diastereomer B), chloroacetyl chloride and sodium hydride, and purification of the base on a silica gel column using toluene/ethyl acetate=6:4 as eluant.
Yield: 71% of theory.

(b)

N-[2-(4-Carbomethoxymethoxyphenyl)-1-methylethyl]-2-(2-trifluoromethyl-thiazol-4-yl)morpholine (Diastereomer B)

Prepared by analogy to Example 74b by reaction of N-[2-(4-carbomethoxymethoxyphenyl)-1-methylethyl]-2-(2-trifluoromethyl-thiazol-4-yl)morpholin-5-one (diastereomer B) with diborane in tetrahydrofuran, followed by purification of the base on a silica gel column using toluene/ethyl acetate=8:2 as eluant.
Yield: 53% of theory,
Calculated: C 54.04; H 5.22; N 6.20. Found: C 54.31; H 5 35; N 6.22.
$^1$H-NMR spectrum (400 MHz) (CDCl$_3$/CD$_3$OD): $\delta$=4.829 ppm (dd, 1H).

EXAMPLE 76

N-[2-(4-Carbomethoxymethoxyphenyl)-1-methylethyl]-N-(carboethoxymethyl)-2-hydroxy-2-(2-trifluoromethylthiazol-4-yl)ethanamine 0.21 g (0.005 mol) of N-[2-(4-Carbomethoxymethoxyphenyl)-1-methylethyl]-2-hydroxy-2-(2-trifluoromethylthiazol-4-yl) ethanamine is dissolved in 10 ml of butan-2-one, and 0.5 ml of ethyl bromoacetate and 0.5 g of potassium carbonate are added, and the mixture is stirred at room temperature for 16 hours. The inorganic products are removed by filtration, and the solvent is removed by distillation. The remaining oil is purified on a silica gel column using toluene/ethyl acetate=85:15 as eluant. A colourless oil is obtained.
Yield: 0.14 g (56% of theory),
Calculated: C 52.47; H 5.41; N 5.56. Found: C 52.71; H 5.42; N 5.57.
According to the $^1$H-NMR spectrum (400 MHz) the product is an approximately 50:50 mixture of the diastereomers.

EXAMPLE 77

N-[2-(4-Carbomethoxymethoxyohenyl)-1-methylethyl]-N-(carboxymethyl)-2-hydroxy-2-(2-trifluoromethyl-thiazol-4-yl)ethanamine 1.4 g (0.0031 mol) of N-[2-(4-Carbomethoxymethoxyphenyl)-1-methylethyl]-2-(2-trifluoromethyl-thiazol-4-yl)morpholin-6-one are dissolved in 10 ml of methanol. 3 ml (0.003 mol) of 1N sodium hydroxide solution are added to this stirred solution at room temperature. After 5 minutes 15 ml of ice-water are added, and the mixture is neutralised with 3 ml of 1N hydrochloric acid. The aqueous phase is extracted by shaking 3 x with methylene chloride. The organic phase is dried over sodium sulphate, filtered and evaporated to dryness. The resulting residue is purified on a silica gel column using methylene chloride methanol=20:1 as eluant. This results, after concentration, in colourless crystals.
Yield: 0.29 g (21% of theory),
Melting point: 128° C.
Calculated: C 50.41; H 4.86; N 5.88. Found: C 50.19; H 4.89; N 5.74.
According to the $^1$H-NMR spectrum (400 MHz) the product is an approximately 50:50 mixture of the diastereomers.

EXAMPLE 78

N-[2-(4-(2-(1-piperidino)ethoxy)phenyl)-1-methylethyl]-2-hydroxy-2-(2-methyl-thiazol-4-yl)ethanamine Prepared by analogy to Example 13 by reaction of 2-hydroxy-2-(2-methyl-thiazol-4-yl)ethanamine with 1-(4-(2-(1-piperidino)ethoxy)phenyl)propan-2-one followed by purification on a silica gel column using methanol as eluant.
Yield: 13% of theory,
Melting point: 128° C.
Calculated: C 65.48; H 8.24; N 10.41; S 7.94. Found: C 65.39; H 8.17; N 10.29; S 7.79.
$^1$H-NMR spectrum (400 MHz) (CDCl$_3$): $\delta$=4.75 (dd, CH—OH); $\delta$=4.70 (dd, C$\underline{\text{H}}$—OH).
According to the 1H-NMR spectrum (400 MHz) the product is an approximately 1:1 mixture of the diastereomers.

EXAMPLE 79

N-[2-(4-(2-Hydroxyethoxy)phenyl)-1-methylethyl]-2-hydroxy-2-(2-methyl-thiazol-4-yl)ethanamine Prepared by analogy to Example 13 by reaction of 2-hydroxy-2-(2-methyl-thiazol-4-yl)ethanamine with 1-[4-(2-hydroxyethoxy)phenyl)propan-2-one followed by purification on a silica gel column using methylene chloride/methanol=9:1 as eluant.
Yield: 61% of theory,
Calculated: C 60.69; H 7.19; N 8.33; S 9.53. Found: C 60.59; H 7.13; N 8.25; S 9.47.
$^1$H-NMR spectrum (400 MHz) (CDCl$_3$): $\delta$=4.78 (dd, CH—OH), $\delta$=4.83 (dd, C$\underline{\text{H}}$—OH).
According to the $^1$H-NMR spectrum (400 MHz) the product is an approximately 1:1 mixture of the diastereomers.

EXAMPLE 80

N-[2-(4-Carbomethoxyphenyl)-1-methylethyl]-2-hydroxy-2-(2-dimethylamino-thiazol-4-yl)ethanamine 5 g of 2-(N,N-dimethylamino)-4-bromoacetylthiazole in 250 ml of acetone are heated to reflux with 10 g of potassium hydrogen carbonate and 9.5 g of 2-(4-carbomethoxyphenyl)-1-methylethylamine-hydrochloride for 3 hours. After the reaction mixture has been cooled the inorganic products are removed by filtration, and the filtrate is concentrated in a rotary evaporator. The resulting oil residue is taken up in 150 ml of absolute methanol and, at 0°-5° C., 1.75 g of sodium borohydride are added in small poritons. The mixture is then stirred at 0°-5° C. for one hour and at room temperature for 24 hours. Then ice-water are added to the reaction mixture, and it is acidified with concentrated hydrochloric acid, made alkaline with ammonia, while cooling in ice, and extracted with methylene chloride. The extract is dried over sodium sulphate, concentrated and purified on a silica gel column using ethyl acetate/methanol=8:2 as eluant.

Yield: 0.5 g (6.8% of theory),

Calculated: C 59.43; H 6.93; N 11.56; S 8.82. Found: C 59.38; H 7.07; N 11.39; S 9.04.

1H-NMR spectrum (400 MHz) (CDCl3/CD3OD): δ=6.39 ppm (s, 1H); δ=6.37 ppm (s, 1H).

According to tee 1H-NMR spectrum (400 MHz) the product is an approximately 2:1 mixture of the diastereomers.

EXAMPLE 81

N-[2-(Carbomethoxymethoxyphenyl)-1-methylethyl]-2-(2-methyl-thiazol-4-yl)morpholine Prepared by analogy to Example 13 by reaction of 2-(2-methyl-thiazol-4-yl)morpholine with 1-(4-carbomethoxymethoxyphenyl)propan-2-one followed by purification on a silica gel column using toluene/ethyl acetate=6:4 as eluant.

Yield: 22% of theory,

Calculated: 61.52; H 6.71; N 7.171; S 8.21. Found: 61.68; H 6.89; N 6.98; S 8.32.

1H-NMR spectrum (400 MHz) (CDCl3/CD3OD): δ=2.71 ppm (s, 1H); δ=2.72 ppm (s, 1H).

According to the 1H-NMR spectrum (400 MHz) the product is an approximately 1:1 mixture of the diastereomers.

EXAMPLE 82

N-[2-(4-(2-Hydroxyethoxy)phenyl)-1-methylethyl]-2-hydroxy-2-(2-trifluoromethyl-thiazol-4-yl)ethanamine Prepared by analogy to Example 13 by reaction of 2-hydroxy-2-(2-trifluoromethyl-thiazol-4-yl)ethanamine with 1-(4-(2-hydroxyethoxy)phenyl)propan-2-one followed by purification on a silica gel column using ethyl acetate/methanol=9:1 as eluant.

Yield: 27.6% of theory,

Calculated: C 52.30; H 5.42; N 7.18; S 8.21. Found: C 52.19; H 5.57; N 7.13; S 8.40.

1H-NMR spectrum (400 MHz) (CDCl3/CD3OD): δ=7.60 ppm (s, 1H) δ=7.57 ppm (s, 1H).

According to the 1H-NMR spectrum (400 MHz) the product is an approximately 1:1 mixture of the diastereomers.

EXAMPLE 83

N-[2-(4-(2-Methylaminoethoxy)phenyl)-1-methylethyl]-2-hydroxy-2-(2-trifluoromethyl-thiazol-4-yl)ethanamine 1.2 ml of borane/dimethyl sulfide complex are added to a solution of 0.38 g of N-[2-(4-methylaminocarbonylmethoxyphenyl)-1-methylethyl]-2-hydroxy-2-(2-trifluoromethyl-thiazol-4-yl)ethanamine in 20 ml of absolute tetrahydrofuran, and the mixture is heated to reflux for three hours. The 4 ml of methanol are cautiously added dropwise to the reaction mixture, and the mixture is heated to reflux for one hour. After cooling to room temperature, ethereal hydrochloric acid is added. The resulting solution is evaporated, the resulting residue is taken up in 15 ml of water, and the solution is made alkaline with concentrated ammonia and extracted several times with methylene chloride. The combined extracts are dried with sodium sulphate, evaporated and purified on a silica gel column using methylene chloride/methanol=8:2 as eluant.

Yield: 0.06 g (13.6% of theory),

Calculated: C 53.59; H 6.001; N 10.42. Found: C 53.40; H 6.19; N 10.20.

1H-NMR spectrum (400 MHz) (CDCl3/CD3OD): δ=7.60 ppm (s, 1H); δ=7.57 ppm (s, 1H).

According to the 1H-NMR spectrum (400 MHz) the product is an approximately 1:1 mixture of the diastereomers.

EXAMPLE 84

N-[2-(4-Methylaminocarbonylmethoxyphenyl)-1-methylethyl]-2-(2-trifluoromethyl-thiazol-4-yl)morpholine Prepared by analogy to Example 32 by reaction of 2-trifluoromethyl-4-bromoacetyl-thiazole with N-(2-hydroxyethyl)-2-(4-methylaminocarbonylmethoxyphenyl)-1-methylethylamine and potassium hydrogen carbonate in acetone at room temperature, followed by reduction with sodium borohydride in trifluoroacetic acid. The resulting crude product is purified on a silica gel column using toluene/ethyl acetate=2:8 as eluant.

Yield: 47.4% of theory,

Melting point: 96°–98° C.

Calculated: C 54.17; H 5.46; N 9.48; S 7.23. Found: C 53.99; H 5.42; N 9.38; S 7.39.

1H-NMR spectrum (400 MHz) (CDCl3/CD3OD): δ=7.61 ppm (s, 1H); δ=7.59 ppm (s, 1H).

According to the 1H-NMR spectrum (400 MHz) the product is an approximately 1:1 mixture of the diastereomers.

EXAMPLE 85

N-[2-(4-(2-Hydroxyethoxy)phenyl)-1-methylethyl]-2-(2-methyl-thiazol-4-yl)morpholine Prepared by analogy to Example 13 by reaction of 2-hydroxy-2-(2-methyl-thiazol-4-yl)morpholine with 1-[4-(2-hydroxyethyoxy)phenyl]propan-2-one followed by purification on a silica gel column using methylene chloride as eluant.

Yield: 42% of theory,

Calculated: C 63.13; H 6.97; N 7.75. Found: C 63.03; H 6.95; N 7.68.

1H-NMR spectrum (CDCl3/CD3OD): δ=7.14 ppm (s, 1H); δ=7.13 ppm (s, 1H).

According to the 1H-NMR spectrum (400 MHz) the product is an approximately 2:3 mixture of the diastereomers.

EXAMPLE 86

N-[2-(4-Carboxymethoxyphenyl)-1-methylethyl]-2-(2-methyl-thiazol-4-yl)morpholine Prepared by analogy to Example 13 by reaction of 2-(2-methyl-thiazol-4-yl)morpholine with 1-[4-carbomethoxyphenyl]propan-2-one followed by purification on a silica gel column using methylene chloride/ethyl acetate/methanol/ammonia=4:4:2:1 as eluant.

Yield: 28% of theory,

Calculated: C 60.62; H 6.42; N 7.44; S 8.52. Found: C 60.58; H 6.40; N 7.40; S 8.50.

1H-NMR spectrum (CDCl3/CD3OD): δ=7.13 ppm (s, 1H); δ=7.14 ppm (s, 1H).

According to the 1H-NMR spectrum (400 MHz) the product is an approximately 1:1 mixture of the diastereomers.

EXAMPLE 87

N-[2-(4-(6-Hydroxyhexoxy)phenyl)-1-methylethyl]-2-(2-trifluoromethyl-thiazol-4-yl)morpholine Prepared by analogy to Example 32 by reaction of N-(2-hydroxyethyl)-2-(4-(6-hydroxyhexoxy)phenyl)-1-methylethylamine with 2-trifluoromethyl-4-bromoacetyl-thiazole and potassium hydrogen carbonate in acetone at room temperature, followed by reduction with sodium borohydride in trifluoroacetic acid. The resulting crude product is purified on a silica gel column using toluene/ethyl acetate=6:4 as eluant.

Yield: 10.8% of theory,

Calculated: C 58.46; H 6.61; N 5.93; S 6.78. Found: C 58.57; H 6.49; N 5.79; S 6.91.

$^1$H-NMR spectrum (CDCl$_3$/CD$_3$OD): $\delta$=7.61 ppm (s, 1H); $\delta$=7.57 ppm (s, 1H).

According to the $^1$H-NMR spectrum (400 MHz) the product is an approximately 1:1 mixture of the diastereomers.

EXAMPLE 88

N-[2-(4-Methylaminocarbonylmethoxyphenyl)-1-methylethyl]-2-(2-methyl-thiazol-4-yl)morpholin Prepared by analogy to Example 13 by reaction of 2-(2-methyl-thiazol-4-yl)morpholine with 1-(4-methylaminocarbonylmethoxyphenyl)propan-2-one followed by purification on a silica gel column using ethyl acetate as eluant.

Yield: 22.3% of theory,

Calculated: C 61.67; H 6.99; N 10.79; S 8.23. Found: C 61.70; H 6.97; N 10.67; S 8.42.

$^1$H-NMR spectrum (CDCl$_3$/CD$_3$OD): $\delta$=2.72 ppm (s, 3H); $\delta$=2.71 ppm (s, 3H).

According to the $^1$H-NMR spectrum (400 MHz) the product is an approximately 1:1 mixture of the diastereomers.

EXAMPLE 89

N-[2-(4-Aminocarbonylmethoxyphenyl)-1-methylethyl]-2-(2-trifluoromethyl-thiazol-4-yl)morpholine Prepared by analogy to Example 24 by reaction of N-[2-(4-carbomethoxymethoxyphenyl)-1-methylethyl]-2-(2-trifluoromethyl-thiazol-4-yl)morpholine with ammonia followed by purification on a silica gel column using ethyl acetate/toluene=8:2 as eluant.

Yield: 51.7% of theory,

Calculated: C 53.14; H 5.16; N 9,78; S 7.47. Found: C 53.26; H 5.34; M 9.63; S 7.59.

$^1$H-NMR spectrum (CDCl$_3$/CD$_3$OD): $\delta$=7.71 ppm (s, 1H); $\delta$=7.69 ppm (s, 1H).

According to the $^1$H-NMR spectrum (400 MHz) the product is an approximately 1:1 mixture of the diastereomers.

EXAMPLE 90

N-[2-(4-(2-Methylaminoethoxy)phenyl)-1-methylethyl]-2-(2-trifluoromethyl-thiazol-4-yl)morpholine Prepared by analogy to Example 83 by reaction of N-[2-(4-methylaminocarbonylmethoxyphenyl)-1-methylethyl]-2-(2-trifluoromethyl-thiazol-4-yl)morpholine with borane dimethylsulfide complex followed by purification on a silica gel column using ethyl acetate/methanol (8:2) as eluant.

Yield: 26% of theory,

Calculated: C 55.93; H 6.10; N 9.78. Found: C 56.08; H 6.21; N 9.65.

$^1$H-NMR spectrum (CDCl$_3$/CD$_3$OD): $\delta$=7.63 ppm (s, 1H); $\delta$=7.59 ppm (s, 1H).

According to the 1H-NMR spectrum (400 MHz) the product is an approximately 1:1 mixture of the diastereomers.

EXAMPLE 91

N-[2-(4-(6-Hydroxyhexoxy)phenyl)-1-methylethyl]-2-(2-trifluoromethyl-thiazol-4-yl)ethanamine Prepared by analogy to Example 13 by reaction of 2-hydroxy-2-(2-trifluoromethyl-thiazol-4-yl)ethanamine with 1-(4-(6-hydroxyhexoxyphenyl)propan-2-one followed by purification on a silica gel column using ethyl acetate/methanol (9.5:0.5) as eluant.

Yield: 17.4% of theory.

Calculated: C 56.49; H 6.55; N 6.27; S 7.18. Found: C 56.32; H 6.47; N 6.34; S 7.28.

$^1$H-NMR spectrum (CDCl$_3$/CD$_3$OD): $\delta$=7.59 ppm (s, 1H); $\delta$=7.55 ppm (s, 1H).

According to the $^1$H-NMR spectrum (400 MHz) the product is an approximately 1:1 mixture of the diastereomers.

EXAMPLE 92

N-[2-(4-Carbomethoxyphenyl)-1-methylethyl]-2-(2-trifluoromethyl-5-methyl-thiazol-4-yl)morpholine Prepared by analogy to Example 32 by reaction of 4.2 g (0.0146 mol) of 2-trifluoromethyl-5-methyl-4-bromoacetyl-thiazole with 8 g (0.03 mol) of N-(2-hydroxyethyl)-2-(4-carbomethoxymethoxyphenyl)-1-methylethylamine in methylene chloride by stirring at room temperature for 20 hours and heating under reflux for 2 hours. The reduction is carried out in 28 ml of trifluoroacetic acid using 2.4 g (0.02 mol) of triethylsilane. The crude product is purified on a silica gel column using toluene/ethyl acetate=7:3 as eluant.

Yield: 1.7 g (28% of theory),

Calculated: C 55.01; H 5.49; N 6.10; S 6.99. Found: C 55.20; H 5.60; N 6.30; S 7.20.

$^1$H-NMR spectrum (CDCl$_3$/CD$_3$OD): $\delta$=4.775 ppm (t, 1H); $\delta$=4.810 ppm (t, 1H).

According to the 1H-NMR spectrum (400 MHz) the product is an approximately 3:2 mixture of the diastereomers.

EXAMPLE 93

N-[2-(4-Carbomethoxymethoxyphenyl)-1-methylethyl]-2-(2-acetamino-thiazol-4-yl)morpholine Prepared by analogy to Example 32 by reaction of 2.23 g (0.0085 mol) of 2-acetylamino-4-bromoacetyl-thiazole with 2.26 g of (0.0085 mol) of N-(2-hydroxyethyl)-2-(4-carbomethoxymethoxyphenyl)-1-methylethylamine and 0.86 g (0.0085 mol) of triethylamine in 30 ml of methylene chloride and 30 ml of methanol for 20 hours at room temperature. The reduction is carried out in 9 ml of trifluoroacetic acid using 1.48 g (0.0128 mol) of triethylsilane. The crude product is purified on a silica gel column using ethyl acetate/methanol=9:1 as eluant.

Yield: 1 g (27% of theory),

Melting point: 65°–70° C.

Calculated: C 58.18; H 6.27; N 9.69; S 7.33. Found: C 57.90; H 6.40; N 9.49; S 7.48.

¹H-NMR spectrum (CDCl₃/CD₃OD): δ=6.875 ppm (d, 1H); δ=6.850 ppm (d, 1H).

According to the ¹H-NMR spectrum (400 MHz) the product is an approximately 2:1 mixture of the diastereomers.

EXAMPLE 94

N-[2-(4-Carbomethoxymethoxyphenyl)-1-methylethyl]-2-hydroxy-2-(2-methyl-oxazol-4-yl)ethanamine dihydrochloride Prepared by analogy to Example 13 by reaction of 0.7 g (0.005 mol) of 2-hydroxy-2-(2-methyl-oxazol-4-yl)-ethanamine and 1.1 g (0.005 mol) of 1-(4-carbomethoxymethoxyphenyl)propan-2-one in 40 ml absolute methanol with 0.3 g (0.005 mol) of acetic acid and 0.32 g (0.005 mol) of sodium cyanoborohydride. The crude product is purified on a silica gel column using ethyl acetate/methanol=9:1 as eluant, and the dihydrochloride is prepared by precipitation with ethereal hydrochloric acid.

Yield: 0.6 g (28% of theory),

Melting point: 160° C. sintering, above 168° C. decomp.

Calculated: C 51.30; H 6.21; N 6.64; S 16.84; Found: C 51.50; H 6.10; N 6.76; S 16.57.

¹H-NMR spectrum (CDCl₃/CD₃OD): δ=7.49 ppm (d, 1H); δ=7.51 ppm (d, 1H).

According to the ¹H-NMR spectrum (400 MHz) the product is an approximately 50:50 mixture of the diastereomers.

EXAMPLE 95

N-[2-(4-Carbomethoxymethoxyphenyl)-1-methylethyl]-2-(2-chloro-thiazol-4-yl)morpholine Prepared by analogy to Example 32 by reaction of 5 g (0.0208 mol) of 2-chloro-4-bromoacetyl-thiazole with 5.6 g (0.021 mol) of N-(2-hydroxyethyl)-2-(4-carbomethoxymethoxyphenyl)-1-methylethylamine in 200 ml of acetone and 6.3 g (0.063 mol) of potassium hydrogen carbonate over 20 hours at room temperature. The reduction is carried out in 41 ml of trifluoroacetic acid using 3.5 g (0.029 mol) of triethylsilane for 24 hours. The crude product is purified on a silica gel column using methylene chloride/methanol=20:1 as eluant.

Yield: 1.2 g (16% of theory),

Calculated: C 55.53; H 5.64; N 6.81. Found: C 55.41; H 5.70; N 6.57.

¹H-NMR spectrum (CDCl₃/CD₃OD): δ=7.21 ppm (d, 1H); δ=7.22 ppm (d, 1H).

According to the ¹H-NMR spectrum (400 MHz) the product is an approximately 2:3 mixture of the diastereomers.

EXAMPLE 96

N-[2-(4-Carboxymethoxyohenyl)-1-methylethyl]-2-(2-amino-thiazol-4-yl)morpholine dichloride 1.6 g (0.0037 mol) of N-[2-(4-carbomethoxymethoxyphenyl)-1-methylethyl]-2-(2-acetamino-thiazol-4-yl)-morpholine in 100 ml of 18% strength hydrochloric acid are heated to reflux under nitrogen for 48 hours. 1.5 g of active charcoal are added to the reaction solution which is throughly stirred and filtered. The solution is then concentrated, and the product is dried in vacuo over potassium hydroxide.

Yield: 1.66 g (100% of theory),

Calculated: C 47.99; H 9.32; N 8.32; S 7.11; Cl 15.76. Found: C 48.20; H 9.45; N 8.99; S 7.18; Cl 15.78.

According to the ¹H-NMR spectrum (400 MHz) the product is a 2:1 mixture of the diastereomers.

EXAMPLE 97

N-[2-(4-Carboxymethoxyphenyl)-1-methylethyl]-2-(2-chloro-thiazol-4-yl)morpholine 0.55 g (0.0013 mol) of N-[2-(4-carbomethoxymethoxy-phenyl)-1-methylethyl]-2-(2-chloro-thiazol-4-yl)morpholine are stirred in 4 ml of methanol and 4 ml of 1N sodium hydroxide solution at room temperature for 10 minutes. The mixture is then neutralised with 4 ml of 1N hydrochloric acid, and the product is obtained by extraction with methylene chloride.

Yield: 0.52 g (100% of theory),

Melting point: 80°–90° C. (decomp.)

Calculated: C 54.47; H 5.33; N 7.05; Cl 8.93. Found: C 54.40; H 5.42; N 7.00; Cl 8.90.

According to the ¹H-NMR spectrum (400 MHz) the product is a 2:3 mixture of the diastereomers.

EXAMPLE 98

N-[2-(4-(2-Hydroxyethoxy)phenyl)-1-methylethyl]-2-(2-chloro-thiazol-4-yl)morpholine Prepared by analogy to Example 71 by reaction of N-[2-(4-carbomethoxymethoxyphenyl)-1-methylethyl]-2-(2-chloro-thiazol-4-yl)morpholine with borane/tetrahydrofuran complex (1 molar solution in tetrahydrofuran) for 60 hours.

Yield: 35% of theory,

¹H-NMR spectrum (CDCl₃/CD₃OD): δ=7.209 ppm (d, 1H); δ=7.228 ppm (d, 1H).

According to the ¹H-NMR spectrum (400 MHz) the product is a 2:3 mixture of the diastereomers.

EXAMPLE 99

N-[2-(4-(2-Hydroxyethoxy)phenyl)-1-methylethyl]-2-hydroxy-2-(2-chloro-thiazol-4-yl)ethanamine Prepared by analogy to Example 71 by reaction of N-[2-(4-carboxymethoxyphenyl)-1-methylethyl]-2-hydroxy-2-(2-chlorothiazol-4-yl)ethanamine with borane/tetrahydrofuran complex (1 molar solution in tetrahydrofuran) for 24 hours.

Yield: 20% of theory,

¹H-NMR spectrum (CDCl₃/CD₃OD): δ=7.195 ppm (d, 1H); δ=7.22 ppm (d, 1H).

According to the ¹H-NMR spectrum (400 MHz) the product is a 1:1 mixture of the diastereomers.

EXAMPLE 100

N-[2-(4-Carboxymethoxyphenyl)-1-methylethyl]-2-hydroxy-2-(2-chloro-thiazol-4-yl)ethanamine Prepared by analogy to Example 97 by reaction of N-[2-(4-carbomethoxymethoxyphenyl)-1-methylethyl]-2-hydroxy-2-(2-chloro-thiazol-4-yl)ethanamine with 1N sodium hydroxide solution in methanol Yield: 0.19 g (100% of theory), Melting point: 58°–63° C.

Calculated: C 51.82; H 5.16; N 7.55. Found: C 51.75; H 5.22; N 7.58.

EXAMPLE 101

N-[2-(4-(2-Hydroxyethoxy)-phenyl)-1-methylethyl]-N-(2-hydroxyethyl)-2-hydroxy-2-(2-trifluoromethyl-thiazol-4-yl)ethanamine Prepared by analogy to Example 71 by reaction of N-[2-(4-carboxymethoxyphenyl)-1-methylethyl]-N-(2-hydroxyethyl)-2-hydroxy-2-(2-trifluoromethyl-thiazol-4-yl)-ethanamine in tetrahydrofuran with diborane in tetrahydrofuran and purification of the base on a silica gel column using an ethyl acetate/methanol=20:1 as eluant.

Yield: 54% of theory, oil,

Calculated: C 52.52; H 5.80; N 6.45. Found: C 52.19; H 5.72; N 6.39.

$^1$H-NMR spectrum (400 MHz) (CDCl$_3$/CD$_3$OD): δ=7.828 ppm (s, 1H); δ=7.839 ppm (s, 1H).

The product is a 60:40 mixture of the diastereomers.

EXAMPLE 102

N-[2-(4-Carbomethoxymethoxyphenyl)-1-methylethyl]-2-(2-oiperidino-thiazol-4-yl)morpholine Prepared by analogy to Example 32 by reaction of 2.9 g (0.1 mol) of 2-piperidino-4-bromoacetyl-thiazol with 3.2 g (0.012 mol) of N-(2-Hydroxyethyl)-2-(4-carbomethoxyphenyl)-1-methylethylamine in 200 ml acetone in the presence of 3 g (0.03 mol) of potassium hydrogen carbonate followed by a reduction in 60 ml of trifluoroacetic acid with 2.9 g (0.076 mol) of sodium borohydride for 24 hours. The substance is purified on a silica gel column using ethyl acetate as eluant, a yellow oil being obtained.

Yield: 0.8 g (17% of theory),

Calculated: C 62.71; H 7.23; N 9.14; S 6.97. Found: C 62.50; H 7.33; N 9.40; S 6.92.

According to the $^1$H-NMR spectrum (400 MHz) the product is an approximately 33:66 mixture of the diastereomers: δ=6.33 ppm (d, 1H); δ=6.44 ppm (d, 1H).

EXAMPLE 103

N-[2-(4-Carbomethoxymethoxyphenyl)-1-methylethyl]-2-hydroxy-2-(2-piperidino-thiazol-4-yl)ethanamine hydrochloride Prepared by analogy to Example 3 by reaction of 2-piperidino-4-bromoacetyl-thiazole with 2-(4-carbomethoxymethoxyphenyl)-1-methylethylamine followed by reduction. The compound is purified on a silica gel column using ethyl acetate/methanol=9:1 as eluant, and the base is converted into the hydrochloride using ethereal hydrochloric acid.

Yield: 13% of theory,

Melting point: above 100° C. decomp.

Calculated: C 52.16; H 6.56; N 8.29; S 6.32; Cl 14.01. Found: C 51.80; H 6.83; N 8.17; S 6.48; Cl 13.72.

According to the $^1$H-NMR spectrum (400 MHz) the product is an approximately 50:50 mixture of the diastereomers.

EXAMPLE 104

N-[2-(4-Carbomethoxyphenyl)-1-methylethyl]-2-hydroxy-2-(2-trifluoromethyl-thiazol-4-yl)ethanamine 0.54 g (0.030 mol) of 2-(2-trifluoromethyl-thiazol-4-yl)ethylene oxide is dissolved in 5 ml of ethanol, and the solution is added dropwise within 10 minutes to a boiling solution of 0.58 g (0.0030 mol) of 2-(4-carbomethoxyphenyl)-1-methylethylamine in 13 ml ethanol. The mixture is then boiled under reflux for 5 hours, the solvent is removed by distillation, and the base is purified on a silica gel column using methylene chloride/methanol=20:1 as eluant.

Yield 0.45 g (38% of theory),

Calculated: C 52.57; H 4.93; N 7.21. Found: C 52.34; H 5.11; N 7.11.

$^1$H-NMR spectrum (400 MHz) (CDCl$_3$/CD$_3$OD): δ=7.58 ppm (s, 1H); δ=7.61 ppm (s, 1H).

The product is an approximately 50:50 mixture of the diastereomers.

EXAMPLE 106

N-[2-(4-Carbomethoxymethoxyphenyl)-1-methylethyl]-2-hydroxy-2-(2-trifluoromethyl-thiazol-4-yl)ethanamine Prepared by analogy to Example 104 by reaction of 2-(2-trifluoromethyl-thiazol-4-yl)ethylene oxide with 2-(4-carbomethoxymethoxyphenyl)-1-methylethylamine and dimethyl sulfoxide at 90° C. for 16 hours. The base is obtained by extraction by shaking with ether and purification on a silica gel column using methylene chloride/methanol 20:1 as eluant.

Yield 24% of theory,

Calculated: C 51.66; H 5.06; N 6.70. Found: C 51.50; H 4.99; N 6.71.

$^1$H-NMR spectrum (400 MHz) (CDCl$_3$/CD$_3$OD): δ=7.57 ppm (d, 1H); δ=7.61 ppm (d, 1H).

The product is an approximately 50:50 mixture of the diastereomers.

EXAMPLE 106

N-[2-(4-(2-Hydroxyethoxy)phenyl)-1-methylethyl]-N-(2-hydroxy-ethyl)-2-hydroxy-2-(2-chloro-thiazol-4-yl)ethanamine Prepared by analogy to Example 30 by reaction of 2-chloro-4-bromoacetyl-thiazole with N-(2-hydroxyethyl)-2-(4-carbomethoxymethoxyphenyl)-1-methylethylamine followed by reduction in methanol with sodium borohydride at room temperature. The crude product is purified on a silica gel column using chloroform/ethyl acetate/methanol=10:9:1 as eluant.

Yield: 15% of theory,

Calculated: C 53.92; H 6.29; N 6.99; S 8.00; Cl 8.84. Found: C 53.68; H 6.30; N 6.57; S 7.61; Cl 8.72.

$^1$H-NMR spectrum (400 MHz) (CDCl$_3$/CD$_3$OD): δ=7.22 ppm (d, 1H); δ=7.11 ppm (d, 1H).

According to the $^1$H-NMR spectrum (400 MHz) the product is an approximately 1:1 mixture of the diastereomers.

EXAMPLE 107

N-[2-(4-Methoxycarbonylmethoxyphenyl)-1-methylethyl]-2-methoxy-2-(2-methyl-thiazol-4-yl)ethanamine dihydrochloride×1.5 H$_2$O Prepared by analogy to Example 13 by reaction of 2-methoxy-2-(2-methyl-thiazol-4-yl)ethanamine with 1-(4-methoxycarbonylmethoxyphenyl)propan-2-one followed by purification of the base by column chromatography on silica gel using chloroform/methanol=10/1 as eluant.

Yield: 58% of theory, $^1$H-NMR spectrum (400 MHz) (CDCl$_3$): δ=4.40 ppm (dd, =CH—OMe); δ=4.44 ppm (dd, =CH—OMe).

According to the $^1$H-NMR spectrum the product is an approximately 50:50 mixture of the diastereomers.

The oily base is converted into a foam-like dihydrochloride using hydrogen chloride/methanol.

Melting point: 60°–80° C.

Calculated: (x1.5 H₂O): C 47.69; H 6.53; N 5.86; S 6.70; Cl 14.82. Found: C 47.77; H 6.68; N 6.01; S 7.07; Cl 14.98.

EXAMPLE I

Coated tablet containing 10 mg of N-[2-(4-carbomethoxymethoxyphenyl)-1-methylethyl]-2-hydroxy-2-(2-trifluoromethyl-thiazol-4-yl)-ethanamine Composition:
1 Coated tablet contains:

| (1) Active substance | 10.0 mg |
|---|---|
| (2) Lactose | 69.0 mg |
| (3) Maize starch | 35.0 mg |
| (4) Polyvinylpyrrolidone | 5.0 mg |
| (5) Magnesium stearate | 1.0 mg |
| | 120.0 mg |

Preparation:

(1)+(2)+(3) are mixed and moistened with (4) in an aqueous solution. The moist composition is beaten through a screen of mesh width 1.6 mm and is dried in a circulating drier at 45° C. The dry granules are passed through a screen of mesh with 1 mm and mixed with (5). The finished mixture is compressed to form tablet cores.

Core weight: 120.0 mg
Diameter: 7.0 mm
Radius of curvature: 6.0 mm

The tablet cores which have been prepared in this way are coated in known manner with a layer essentially composed of sugar and talc. This layer can also contain colouring extracts. The finished coated tablets are polished with wax.

Weight of coated tablet: 180.0 mg

EXAMPLE II

Coated methoxyphenyl)-1-methylethyl]-2-hydroxy-2-(2-trifluoromethyl-thiazol-4-yl)-ethanamine Composition:
1 Coated tablet contains:

| (1) Active substance | 5.0 mg |
|---|---|
| (2) Lactose | 10.8 mg |
| (3) Maize starch | 50.0 mg |
| (4) Polyvinylpyrrolidone | 8.0 mg |
| (5) Magnesium stearate | 1.2 mg |
| | 220.0 mg |

Preparation:
The preparation is carried out by analogy to Example I.

Core weight: 220.0 mg
Diameter: 9.0 mm
Radius of curvature: 8.0 mm
Weight of coated tablet: 300.0 mg

EXAMPLE III

Tablets containing 150 mg of N-[2-(4-carbomethoxymethoxyphenyl)-1-methylethyl]-2-hydroxy-2-(2-trifluoromethyl-thiazol-4-yl)-ethanamine Composition:
1 tablet contains:

| (1) Active substance | 150.0 mg |
|---|---|
| (2) Lactose | 86.0 mg |
| (3) Maize starch | 50.8 mg |
| (4) Microcrystalline cellulose | 25.0 mg |
| (5) Polyvinylpyrrolidone | 7.0 mg |
| (6) Magnesium stearate | 1.2 mg |
| | 320.0 mg |

Preparation:

(1)+(2)+(3)+(4)+(5) are mixed and moistened with water. The moist composition is beaten through a screen of mesh width 1.6 mm and is dried at 45° C. The dry granules are passed once more through the same screen, and are mixed with (6). Tablets are compressed from the finished mixture.

Tablet weight: 320.0 mg
Diameter: 10.0 mm

The tablets are provided with a dividing groove to allow them to be halved.

EXAMPLE IV

Hard gelatine capsules containing 100 mg of N-[2-(4-carbomethoxymethoxyphenyl)-1-methylethyl]-2-hydroxy-2-(2-trifluoromethyl-thiazol-4-yl)-ethanamine Composition:
1 Capsule contains:
Capsule shell: Size 3 hard gelatine capsules
Capsule contents:

| (1) Active substance | 100.0 mg |
|---|---|
| (2) Lactose × 1H₂O | 38.0 mg |
| (3) Maize starch (dried) | 60.0 mg |
| (4) Magnesium stearate | 2.0 mg |
| Weight of capsule contents: | 200.0 mg |
| (5) Distilled water | q.s. |

Preparation:

An approximately 10% solution in distilled water is prepared with a small portion of the lactose (granulating liquid). The active substance, the remaining lactose and the maize starch are mixed and thoroughly moistened with the granulating liquid. The composition is screened, dried and, after another screening is homogeneously mixed with magnesium sterate. The fine-grained granules are dispensed into capsules in a suitable machine.

EXAMPLE V

Hard gelatine capsules containing 200 mg of N-[2-(4-carbomethoxymethoxyphenyl)-1-methylethyl]-2-hydroxy-2-(2-trifluoromethyl-thiazol-4-yl)-ethanamine Composition:
1 Capsule contains:
Capsule shell: Size 1 hard gelatine capsules

| | |
|---|---|
| (1) Active substance | 200.0 mg |
| (2) Lactose × 1H$_2$O | 47.0 mg |
| (3) Maize starch (dried) | 70.0 mg |
| (4) Magnesium stearate | 3.0 mg |
| Weight of capsule contents: | 320.0 mg |
| (5) Distilled water | q.s. |

Preparation:

An approximately 10% solution in distilled water is prepared with a small portion of the lactose (granulating liquid). The active substance, the remaining lactose and the maize starch are mixed and thoroughly moistened with the granulating liquid. The composition is screened, dried and, after another screening is homogeneously mixed with magnesium sterate. The fine-grained granules are dispensed into capsules in a suitable machine. It has also been found that the new 2-hydroxy-morpholines of general formula

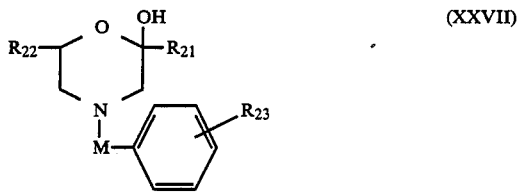 (XXVII)

and the optical isomers, diastereomers and acid addition salts thereof, particularly the physiologically acceptable acid addition salts thereof for pharmaceutical use, have valuable pharmacological properties, namely a superior effect on metabolism, and preferably a superior effect of lowering blood sugar and reducing body fat, and lowering the atherogenic lipoproteins VLDL and LDL.

In general formula I above

M represents an n-alkylene group containing 2 or 3 carbon atoms optionally mono- or disubstituted by methyl or ethyl groups, $R_{21}$ represents a thiazolyl group optionally substituted by a halogen atom or by a trifluoromethyl or alkyl group, a phenyl group optionally substituted by one or two halogen atoms or by a trifluoromethyl, cyano, alkyl or alkoxy group, a phenyl group substituted by a halogen atom and by an alkyl or alkoxy group, a phenyl group substituted by an alkyl group and by an alkoxy group, or an aminophenyl group which is substituted by one or two halogen atoms or by a cyano group or by a halogen atom and a cyano group, $R_{22}$ represents a hydrogen atom or a thiazolyl group optionally substituted by a halogen atom or by a trifluoromethyl or alkyl group and $R_{23}$ represents a hydroxy, alkoxy, carboxy, alkoxycarbonyl, aminocarbonyl, alkylaminocarbonyl or dialkylaminocarbonyl group, an alkoxy group containing 1 to 6 carbon atoms which is substituted in the end position by a carboxy, alkoxycarbonyl, aminocarbonyl, alkylaminocarbonyl or dialkylaminocarbonyl group, an alkoxy group containing 2 to 7 carbon atoms substituted in the end position by a hydroxy, alkoxy, phenylalkoxy, amino, alkylamino, dialkylamino, pyrrolidino, piperidino or hexamethyleneimino group, or an ethenylene group optionally substituted by an alkyl group and substituted in the end position by a carboxy, alkoxycarbonyl, aminocarbonyl, alkylaminocarbonyl or dialkylaminocarbonyl group, whilst the alkyl or alkoxy groups mentioned in the definitions of groups $R_{21}$, $R_{22}$ and $R_{23}$ may each contain 1 to 3 carbon atoms.

As examples of definitions of the groups given hereinbefore:

M may represent an ethylene, 1-methyl-ethylene, 2-methyl-ethylene, 1-ethyl-ethylene, 2-ethyl-ethylene, 1,2-dimethyl-ethylene, 1,1-dimethyl-ethylene, 1,1-diethyl-ethylene, 1-ethyl-1-methyl-ethylene, 2,2-dimethyl-ethylene, 2,2-diethyl-ethylene, 2-ethyl-2-methyl-ethylene, n-propylene, 1-methyl-n-propylene, 2-methyl-n-propylene, 3-methyl-n-propylene, 1-ethyl-n-propylene, 2-ethyl-n-propylene, 3-ethyl-n-propylene, 1,1-dimethyl-n-propylene, 1,1-diethyl-n-propylene, 2,3-dimethyl-n-propylene, 3,3-dimethyl-n-propylene or 3-ethyl-3-methyl-n-propylene group, $R_{21}$ may represent a thiazolyl, 2-methyl-thiazolyl, 2-ethyl-thiazolyl, 2-n-propyl-thiazolyl, 2-chloro-thiazolyl, 2-bromo-thiazolyl, 2-trifluoromethyl-thiazolyl, phenyl, fluorophenyl, chlorophenyl, bromophenyl, dichlorophenyl, trifluoromethylphenyl, cyanophenyl, methylphenyl, ethylphenyl, isopropylphenyl, methoxyphenyl, ethoxyphenyl, n-propoxyphenyl, methylmethoxyphenyl, chloro-methylphenyl, bromo-methylphenyl, chloro-methoxyphenyl, bromo-methoxyphenyl, amino-chlorophenyl, amino-dichlorophenyl, amino-bromophenyl, amino-chloro-fluorophenyl, amino-chloro-bromophenyl, amino-dibromophenyl, amino-cyanophenyl, amino-fluoro-cyanophenyl or amino-cyano-chlorophenyl group, $R_{22}$ may represent a hydrogen atom, a thiazolyl, 2-methyl-thiazolyl, 2-ethyl-thiazolyl, 2-n-propylthiazolyl, 2-chloro-thiazolyl, 2-bromo-thiazolyl or 2-trifluoromethyl-thiazolyl group and $R_{23}$ may represent a hydroxy, methoxy, ethoxy, n-propoxy, isopropoxy, carboxy, methoxycarbonyl, ethoxycarbonyl, n-propoxycarbonyl, aminocarbonyl, methylaminocarbonyl, ethylaminocarbonyl, isopropylaminocarbonyl, dimethylaminocarbonyl, diethylaminocarbonyl, di-n-propylaminocarbonyl, N-ethyl-methylaminocarbonyl, N-ethyl-isopropyl- aminocarbonyl, 2-hydroxy-ethoxy, 3-hydroxy-n-propoxy, 4-hydroxy-n-butoxy, 5-hydroxy-n-pentyloxy, 6-hydroxy-n-hexyloxy, 7-hydroxy-n-heptyloxy, 2-methoxy-ethoxy 2-ethoxy-ethoxy, 2-n-propoxy- ethoxy, 3-ethoxy-n-propoxy, 4-methoxy-n-butoxy, 6-ethoxy-n-hexyloxy, 2-phenethoxy-ethoxy, 2-amino-ethoxy, 2-methylamino-ethoxy, 2-dimethylamino-ethoxy, 2-isopropylamino-ethoxy, 2-di-n-propylamino-ethoxy, 2-(1-pyrrolidino)ethoxy, 2-(1-piperidino)ethoxy, 2-(1-hexamethyleneimino)-ethoxy, 3-amino-n-propoxy, 6-amino-n-hexyloxy, 7-methylamino-n-heptyloxy, 3-diethylamino-n-propoxy, 3-(1-piperidino)-n-propoxy, 4-dimethylamino-n-butoxy, carboxymethoxy, 2-carboxyethoxy, 3-carboxy-n-propoxy, 4-carboxy-n-butoxy, methoxycarbonylmethoxy, 2-methoxycarbonyl-ethoxy, 6-methoxycarbonyl-hexyloxy, ethoxycarbonylmethoxy, 2-ethoxycarbonyl-ethoxy, 3-ethoxycarbonyl-n-propoxy, n-propoxycarbonylmethoxy, 2-isopropoxycarbonyl-ethoxy, 4-n-propoxycarbonyl-n-butoxy, aminocarbonylmethoxy, 2-aminocarbonyl-ethoxy, 4-aminocarbonyl-n-butoxy, methylamino-carbonylmethoxy, 2-methylaminocarbonyl-ethoxy, dimethylaminocarbonyl-methoxy, 2-dimethyl-aminocarbonyl-ethoxy, 4-dimethylaminocarbonyl-n-butoxy, diethylaminocarbonylmethoxy, 2-diethylaminocarbonyl-ethoxy, 2-di-n- pfopylaminocarbonyl-ethoxy, 2-carboxy-ethenyl, 2-carboxy-1-methyl-ethenyl, 2-carboxy-2-methyl-ethenyl, 2-carboxy-1-ethyl-ethenyl, 2-carboxy-1-n-propyl-ethenyl, 2-methoxy-carbonyl-ethenyl, 2-methoxycarbonyl-1-methyl-ethenyl, 2-ethoxycarbonyl-ethenyl, 2-ethoxycarbonyl-1-methyl-ethenyl or 2-isopropoxycarbonyl-ethenyl group.

In addition to the compounds mentioned in the Examples, the following compounds may also be cited, which are covered by general formula XXVII above:

N-[2-(4-Aminocarbonylmethoxyphenyl)-1-methylethyl]-2-hydroxy-2-(2-trifluoromethyl-thiazol-4-yl)morpholine, N-[2-(4-Carbomethoxyphenyl)-1-methylethyl]-2-hydroxy-2-(2-trifluoromethyl-thiazol-4-yl)morpholine, N-[2-(4-(2-Carbomethoxy-1-methyl-ethenyl)-phenyl)-1-methylethyl]-2-hydroxy-2-(2-trifluoromethyl-thiazol-4-yl)morpholine, N-[2-(4-(2-Methylamino-ethoxy)phenyl)-1-methylethyl]-2-hydroxy-2-(2-trifluoromethyl-thiazol-4-yl)morpholine, N-[2-(4-(2-(1-piperidino)ethoxy)phenyl)-1-methylethyl]-2-hydroxy-2-(2-trifluoromethyl-thiazol-4-yl)morpholine, N-[3-(4-Carboxamidophenyl)-1-methylpropyl]-2-hydroxy-(2-trifluoromethyl-thiazol-4-yl)morpholine, N-[2-(4-Aminocarbonylmethoxyphenyl)-1-methylethyl]-2-hydroxy-2-(2-chloro-thiazol-4-yl)morpholine, N-[2-(4-Methylaminocarbonylmethoxyphenyl)-1-methylethyl]-2-hydroxy-2-(2-chloro-thiazol-4-yl)morpholine, N-[2-(4-(2-Hydroxy-ethoxy)phenyl)-1-methylethyl]-2-hydroxy-2-(2-chloro-thiazol-4-yl)morpholine, N-[2-(4-(6-Hydroxy-n-hexyloxy)phenyl)-1-methylethyl]-2-hydroxy-2-(2-chloro-thiazol-4-yl)morpholine, N-[2-(4-Carbomethoxyphenyl)-1-methylethyl]-2-hydroxy-2-(2-chloro-thiazol-4-yl)morpholine, N-[2-(4-(2-Ethoxy-ethoxy)phenyl)-1-methylethyl]-2-hydroxy-2-(2-chloro-thiazol-4-yl)morpholine, N-[2-(4-(2-(2-phenylethoxy)ethoxy)phenyl)-1-methylethyl]-2-hydroxy-2-(2-chloro-thiazol-4-yl)morpholine, N-[2-(4-(2-Carbomethoxy-1-methyl-ethenyl)phenyl)-1-methylethyl]-2-hydroxy-2-(2-chloro-thiazol-4-yl)-morpholine, N-[2-(4-Carbomethoxymethoxyphenyl)-1-methylethyl]-2-hydroxy-2-(2-methyl-thiazol-4-yl)morpholine, N-[2-(4-Aminocarbonylmethoxyphenyl)-1-methylethyl]-2-hydroxy-2-phenyl-morpholine, N-[2-(4-(2-(2-phenylethoxy)ethoxy)phenyl)-1-methylethyl]-2-hydroxy-2-phenyl-morpholine, N-[2-(4-Carbethoxyphenyl)-1-methylethyl]-2-hydroxy-2-(3-chlorophenyl)morpholine, N-[2-(4-(6-Hydroxy-n-hexyloxy)phenyl)-1-methylethyl]-2-hydroxy-2-(3-chlorophenyl)morpholine, N-[2-(4-(2-Methylamino-ethoxy)phenyl)-1-methylethyl]-2-hydroxy-2-(3-chlorophenyl)morpholine, N-[2-(4-(2-(1-Piperidino)ethoxy)phenyl)-1-methylethyl]-2-hydroxy-2-(3-chlorophenyl)morpholine, N-[2-(4-(2-(2-phenylethoxy)ethoxy)phenyl)-1-methylethyl]-2-hydroxy-2-(3-chlorophenyl)morpholine, N-[2-(4-(2-Ethoxy-ethoxy)phenyl)-1-methylethyl]-2-hydroxy-2-(3-chlorophenyl)morpholine, N-[2-(4-(2-Carbomethoxy-1-methyl-ethenyl)phenyl)-1-methylethyl]-2-hydroxy-2-phenyl-morpholine, N-[2-(4-Aminocarbonylmethoxyphenyl)-1-methylethyl]-2-hydroxy-2-(3-methylphenyl)morpholine, N-[2-(4-Methylaminocarbonylmethoxyphenyl)-1-methylethyl]-2-hydroxy-2-(3-methylphenyl)morpholine, N-[2-(4-(2-Hydroxy-ethoxy)phenyl)-1-methylethyl]-2-hydroxy-2-(3-methylphenyl)morpholine, N-[2-(4-(6-Hydroxy-n-hexyloxy)phenyl)-1-methylethyl]-2-hydroxy-2-(3-methylphenyl)morpholine, N-[2-(4-(2-(2-Phenylethoxy)ethoxy)phenyl)-1-methylethyl]-2-hydroxy-2-(3-methylphenyl)morpholine, N-[2-(4-(2-(2-Phenylethoxy)ethoxy)phenyl)-1-methylethyl]-2-hydroxy-2-(2-trifluoromethyl-thiazol-4-yl)morpholine, N-[2-(4-(2-Ethoxy-ethoxy)phenyl)-1-methylethyl]-2-hydroxy-2-(3-methylphenyl)morpholine, N-[2-(4-Carbomethoxyphenyl)-1-methylethyl]-2-hydroxy-2-(3-methylphenyl)morpholine, N-[2-(4-(2-Carbomethoxy-1-methyl-ethenyl)phenyl)-1-methylethyl]-2-hydroxy-2-(3-methylphenyl)morpholine, N-[2-(4-Aminocarbonylmethoxyphenyl)-1-methylethyl]-2-hydroxy-2-(3-trifluoromethylphenyl)morpholine, N-[2-(4-Methylaminocarbonylmethoxyphenyl)-1-methylethyl]-2-hydroxy-2-(3-trifluoromethylphenyl)morpholine, N-[2-(4-(2-Hydroxy-ethoxy)phenyl)-1-methylethyl]-2-hydroxy-2-(3-trifluoromethylphenyl)morpholine, N-[2-(4-(6-Hydroxy-n-hexyloxy)phenyl)-1-methylethyl]-2-hydroxy-2-(3-trifluoromethylphenyl)morpholine, N-[2-(4-(2-(2-phenylethoxy)ethoxy)phenyl)-1-methylethyl]-2-hydroxy-2-(3-trifluoromethylphenyl)morpholine, N-[2-(4-(2-Ethoxy-ethoxy)phenyl)-1-methylethyl]-2-hydroxy-2-(3-trifluoromethylphenyl)morpholine, N-[2-(4-Carbethoxyphenyl)-1-methylethyl]-2-hydroxy-2-(3-trifluoromethylphenyl)morpholine, N-[2-(4-(2-Carbomethoxy-1-methyl-ethenyl)phenyl)-1-methylethyl]-2-hydroxy-2-(3-trifluoromethylphenyl)-morpholine and N-[2-(4-(2-Carbomethoxy-1-methyl-ethenyl)phenyl)-1-methylethyl]-2-hydroxy-2-(4-amino-3-cyano-5-fluorophenyl)morpholine, and the optical isomers, diastereomers and acid addition salts thereof.

However, the preferred compounds of general formula XXVII are those wherein

M represents an ethylene or n-propylene group optionally substituted by a methyl group, $R_{21}$ represents a thiazolyl group optionally substituted in the 2-position by a halogen atom or by a trifluoromethyl or methyl group, a phenyl group optionally substituted by a halogen atom or by a trifluoromethyl, methyl or methoxy group, or an aminophenyl group which is substituted by a cyano group, a halogen atom, two halogen atoms or by a halogen atom and a cyano group, $R_{22}$ represents a hydrogen atom or a thiazolyl group optionally substituted in the 2-position by a halogen atom or by a trifluoromethyl or methyl group, and $R_{23}$ represents a hdyroxy, methoxy, carboxy, methoxycarbonyl, ethoxycarbonyl, aminocarbonyl, carboxymethoxy, methoxycarbonylmethoxy, ethoxycarbonylmethoxy, aminocarbonylmethoxy, methylaminocarbonylmethoxy, 2-hydroxy-ethoxy, 2-ethoxy-ethoxy, 2-phenethoxy-ethoxy, 2-(1-piperidino)ethoxy, 6-hydroxy-n-hexyloxy or 2-carbomethoxy-1-methyl-ethenyl group, and the optical isomers, diastereomers and acid addition salts thereof.

However, particularly preferred compounds are the compounds of general formula

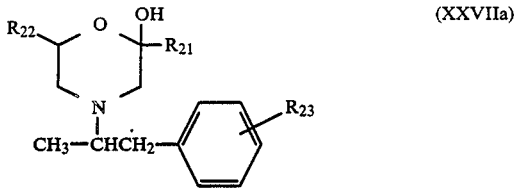

(XXVIIa)

wherein $R_{21}$ represents a thiazol-4-yl group substituted in the 2-position by a chlorine atom or by a trifluoromethyl group, a phenyl group optionally substituted by a chlorine atom or by a trifluoromethyl or methyl group, or a 4-amino-3-fluoro-5-cyano-phenyl group, $R_{22}$ represents a hydrogen atom and $R_{23}$ represents a carboxymethoxy, carbomethoxy- methoxy, ethoxycarbonylmethoxy, aminocarbonyl- methoxy, methylaminocarbonylmethoxy, 2-ethoxy- ethoxy, 2-hydroxy-ethoxy or 2-carbomethoxy-1- methyl-ethenyl group, and the optical isomers, diastereomers and acid addition salts thereof.

According to the invention, the new compounds are obtained by the following process:

Reaction of a compound of general formula

(XXVIII)

wherein $R_{21}$ is defined as hereinbefore and $Z_1$ represents a nucleophilic leaving group, with an amine of general formula

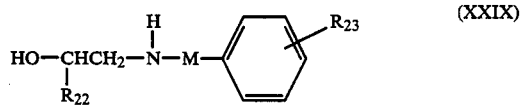

(XXIX)

wherein

M, $R_{22}$ and $R_{23}$ are defined as hereinbefore.

Examples of nucleophilic leaving groups include halogen atoms or sulphonyloxy groups, e.g. a chlorine, bromine or iodine atom or a methanesulphonyloxy, p-toluenesulphonyloxy or ethoxysulphonyloxy group.

The reaction is appropriately carried out in a suitable solvent such as acetone, methylene chloride, tetrahydrofuran or dioxan and preferably in the presence of an acid binding agent such as potassium hydrogen carbonate, potassium carbonate, sodium hydrogen carbonate, sodium carbonate, triethylamine, pyridine or in an excess of the amine of general formula XXIX used, whilst the organic binding agents may simultaneously also be used as solvent, at temperatures of between 0° and 100° C., preferably at temperatures of between 5° and 50° C.

It may also be advantageous for any reactive groups such as hydroxy, carboxy, amino or alkylamino groups, but particularly amino or alkylamino groups, to be protected during the reaction by conventional protecting groups.

Examples of protecting groups for a hydroxy group include the benzyl, benzyloxycarbonyl, tetrahydropyranyl, trimethylsilyl and tert.butyldimethylsilyl groups, protecting groups for a carboxy group include the benzyl, tert.butyl, trimethylsilyl and benzyloxymethyl groups and protecting groups for an amino or alkylamino group include the acetyl, benzoyl, tert-.butoxycarbonyl, benzyloxycarbonyl, ethoxycarbonyl and benzyl groups.

The optional subsequent cleavage of any protecting group used is preferably carried out hydrolytically in an aqueous solvent, e.g. in water, isopropanol/water, tetrahydrofuran/water or dioxan/water, in the presence of an alkali metal base such as sodium hydroxide or potassium hydroxide or an acid such as hydrochloric, sulphuric or trifluoro- acetic acid at temperatures of between 0° and 100° C., preferably at temperatures of between 20° and 50° C.

If according to the invention a compound of general formula XXVII is obtained wherein $R_{23}$ represents or contains an alkoxycarbonyl, aminocarbonyl, alkylaminocarbonyl or dialkylaminocarbonyl group, this may be converted by hydrolysis into a corresponding compound of general formula XXVII wherein $R_{23}$ represents or contains a carboxy group, or If a compound of general formula XXVII is obtained wherein $R_{23}$ represents or contains an alkoxycarbonyl group, this may be converted by amidation into a corresponding compound of general formula XXVII wherein $R_{23}$ represents or contains an aminocarbonyl, alkylaminocarbonyl or dialkylaminocarbonyl group.

Subsequent hydrolysis is carried out in the presence of a base such a sodium hydroxide or potassium hydroxide in a suitable solvent such as water, methanol, ethanol, ethanol/water, water/isopropanol or water/dioxan at temperatures of between −10° C. and 100° C., e.g. at temperatures of between ambient temperature and 50° C.

Subsequent amidation is carried out in a suitable inert solvent such as diethyl ether, tetrahydrofuran, dioxan or in an excess of the amine used, optionally in a pressurised vessel at temperatures of between 0° and 100° C. but preferably at temperatures of between 20° and 80° C.

As already mentioned hereinbefore, the new compounds may occur in the form of their enantiomers, mixtures of enantiomers or racemates or, if they contain at least 2 asymmetric carbon atoms, in the form of their diastereomers or mixtures of diastereomers.

Thus, the compounds of general formula XXVII obtained which contain only one optically active centre may be resolved by known methods (see Allinger N. L. and Elich W. L. in "Topics in Stereochemistry", Vol. 6, Wiley Interscience, 1971) into their optical enantiomers, e.g. by recrystallisation from an optically active solvent or by reaction with an optically active substance which forms a salt with the racemic compound, particularly an acid, and separating the resultant salt mixture, e.g. by means of the differential solubilities, into the diastereomeric salts from which the free enantiomers can be liberated by the use of suitable reagents. Examples of optically active acids in common use include the D and L forms of tartaric acid, di-o-toluoyltartaric acid, malic acid, mandelic acid, camphorsulphonic acid, glutamic acid, aspartic acid and quinic acid.

Furthermore, the compounds of general formula XXVII obtained having at least 2 asymmetric carbon atoms may be resolved into their diastereomers on the basis of their physical/chemical differences using known methods, e.g. by chromatography and/or fractional crystallisation. A pair of enantiomers thus obtained may subsequently be resolved into their optical antipodes as described above. If for example a compound of general formula I contains two optically active carbon atoms the corresponding (R R', S S') and (R S', S R') forms are obtained.

The compounds of general formulae XXVIII and XXIX used as starting materials may be obtained by methods known per se.

Thus, for example, a corresponding thiazole derivative of general formula XXVIII is obtained by bromination of the corresponding acetyl compounds in glacial acetic acid or hydrogen bromide/glacial acetic acid at temperatures of between 20° and 100° C. or by cyclisation of the corresponding thioamides with dibromodiacetyl in a solvent such as diethyl ether, acetonitrile or toluene.

A compound of general formula XXIX used as starting material may, of course, also be used in its optically pure form.

Moreover, the compounds of general formula XXVII obtained may be converted into their acid addition salts, particularly, for pharmaceutical use, their physiologically acceptable salts with inorganic or organic acids. Examples of acids include hydrochloric, hydrobromic, sulphuric, phosphoric, fumaric, succinic, lactic, citric, tartaric and maleic acid.

As already mentioned hereinbefore, the new compounds of general formula XXVII, the enantiomers, mixtures of enantiomers or, if they have at least 2 asymmetric carbon atoms, the diastereomers or mixtures of diastereomers and the acid addition salts thereof, particularly the physiologically acceptable acid addition salts for pharmaceutical use, have valuable pharmacological properties, particularly an effect on metabolism, preferably the effect of lowering blood pressure and reducing body fat and the effect of lowering the atherogenic lipoproteins VLDL and LDL. Moreover, some of the compounds mentioned above also have an anabolic activity.

For example, the following compounds were investigated for their biological properties as follows:

AA = N-[2-(4-Carbomethoxymethoxyphenyl)-1-methylethyl]-2-hydroxy-2-(3-chlorophenyl)morpholine, BB = N-[2-(4-Methylaminocarbonylmethoxyphenyl)-1-methyl-ethyl]-2-hydroxy-2-(3-chlorophenyl)morpholine, CC = N-[2-(4-(2-Hydroxy-ethoxy)phenyl)-1-methylethyl]-2-hydroxy-2-(3-chlorophenyl)morpholine and DD = N-[2-(4-Carbomethoxymethoxyphenyl)-1-methylethyl]-2-hydroxy-2-(2-trifluoromethyl-thiazol-4-yl)-morpholine 1. Antidiabetic activity:

The antidiabetic activity of the compounds according to the invention can be measured as a blood sugarlowering activity in experimental animals. The test substances are suspended in 1.5% methylcellulose and administered by stomach tube to female mice bred by the applicants. 30 minutes later 1 g of glucose per kg of body weight is dissolved in water and administered subcutaneously. Another 30 minutes later blood is taken from the retroorbital venous plexus. From the serum, the amount of glucose is determined by the hexokinase method using an analytical photometer.

The following Table shows the lowering of blood pressure observed in this test, given as a percentage of a control group conducted in parallel. Statistical evaluation is carried out using the Student t test taking p=0.05 as the limit of significance.

| Compound | % change from the level of the control group Dosage [mg/kg] | | |
|---|---|---|---|
| | 0.1 | 0.3 | 1 |
| AA | −55 | −65 | −65 |
| BB | −39 | −55 | −67 |
| CC | −21 | −58 | −63 |
| DD | −13 | −35 | −49 |

2. Anti-obesity activity:

To determine the anti-obesity activity of the compounds according to the invention the increase in lipolysis is measured by the increase in the glycerine in the serum. The design of the test is identical to the test described above for testing the effect of lowering blood sugar. Glycerine is determined in a combined enzymatic/colorimetric test using an analytical photometer. The results are given in the following Table as a percentage of a control group conducted in parallel.

| Compound | % change from the level of the control group Dosage [mg/kg] | | |
|---|---|---|---|
| | 0.1 | 0.3 | 1 |
| AA | 296 | 456 | 552 |
| BB | 267 | 280 | 353 |
| CC | 224 | 574 | 652 |
| DD | 77 | 217 | 330 |

Moreover, in the tests on the substances according to the invention carried out as described above no effects on circulation were observed a the dosages used and no toxic side effects were observed at dosages up to 30 mg/kg p.o. These substances are therefore well tolerated.

In view of their pharmacological properties the new compounds of general formula XXVII and the physiologically acceptable acid addition salts thereof with organic or inorganic acids are therefore suitable for the treatment of both diabetes mellitus and also obesity, and hence particularly for the treatment of obese diabetics. Moreover, the new compounds may be used for the prevention and treatment of atherosclerotic changes in the blood vessels, which occur particularly in diabetics. The dosage required can be matched entirely to the metabolic-physiological requirements of the individual patient since the compounds are free from effects on the heart and circulation over a wide dosage range. In adults, therefore, the daily dosage is between 1 and 3000 mg, preferably from 1 to 1000 mg, divided into 1 to 4 doses per day. For this purpose, the compounds mentioned above, optionally combined with other active substances, may be incorporated in the conventional galenic preparations such as powders, plain and coated tablets, capsules, suppositories and suspensions.

Furthermore, the compounds mentioned above may be used for the treatment of fat animals and, as a consequence of their body fat-reducing (lipolytic) activity, they may be used for the reduction of undesirable fat deposits in animal rearing, i.e. to improve the quality of the meat of fattened animals such as pigs, cattle, sheep and poultry. In animals, the compounds mentioned above may be administered orally or non-orally, e.g. as a feed additive or by injection or by means of implanted minipumps. The daily dosage ranges from 0.01 to 100 mg/kg, but preferably from 0.1 to 10 mg/kg of body weight.

The Examples which follow are intended to illustrate the invention:

EXAMPLE AA

2-Trifluoromethyl-4-bromoacetyl-thiazole 9.2 g (0.071 mol) of trifluorothioacetamide dissolved in 200 ml of acetonitrile is added dropwise, over 2.5 hours, to a boiling solution of 17.4 g (0.071 mol) of dibromodiacetyl in 200 ml of acetonitrile. The solvent is distilled off and the product remaining is extracted with cyclohexane. The extract is evaporated down and the oily residue remaining is purified over a silica gel column using toluene/cyclohexane as eluant.

Yield: 8.2 g (42.7% of theory),
M.p.: 36°–37° C.

EXAMPLE BB

2-Chloro-4-bromoacetyl-thiazole 7.6 g (6.0344 mol) of 2-amino-4-bromoacetyl-thiazole is dissolved in 20 ml of water and 50 ml of concentrated hydrochloric acid. At 0° C., with stirring, a solution of 3.44 g (0.05 mol) of sodium nitrite in 15 ml of water is added dropwise. Then the diazonium salt solution formed is added in batches, with vigorous stirring, to a cold solution of 4.93 g (0.05 mol) of copper(I)chloride in 15 ml of concentrated hydrochloric acid and the mixture is stirred at ambient temperature for 20 hours. It is then diluted with 100 ml of water and extracted with ether. The ether extract is dried over sodium sulphate and evaporated down. For purification the crude product is purified over a silica gel column using methylene chloride as eluant.

Yield: 4 g (48% of theory),
M.p.: 72° C.
Calculated: C 24.96; H 1.25; N 5.82. Found: C 25.12; H 1 1.30; N 6.00.

EXAMPLE CC

N-[2-(4-Carbomethoxymethoxyphenyl)-1-methylethyl]-2-hydroxy-2-(2-trifluoromethyl-thiazol-4-yl)ethanamine (pair of diastereomers A)

1.27 g (6.0 mmol) of 2-hydroxy-2-(2-trifluoromethyl-thiazol-4-yl)ethanamine and 1.33 g (6.0 mmol) of (4-carbomethoxymethoxy)phenyl acetone are dissolved in 40 ml of absolute methanol, 0.34 ml (6.0 mmol) of glacial acetic acid and 0.37 g (6.0 mmol) of sodium cyanoborohydride are added and the mixture is stirred for 5 hours at ambient temperature. It is then poured onto ice, acidified with hydrochloric acid, made alkaline with sodium hydrogen carbonate solution and extracted with chloroform. The extracts are dried and purified by column chromatography on silica gel (eluant: methylene chloride/methanol=20:1). An approximately 50:50 diastereomeric mixture of the base is obtained. This is recrystallised from a mixture of ether and ethyl acetate=65:10 and then recrystallised twice more from ethyl acetate. The pair of diastereomers A is obtained in 98–99% purity.

Yield: 14% of theory,
M.p.: 104°–105° C.
Calculated: C 51.66; H 5.06; N 6.70. Found: C 51.90; H 4 82; N 6.82.
$^1$H NMR spectrum (400 MHz) (CDCl$_3$/CD$_3$OD): $\delta$=7.59 ppm (s, 1H).

EXAMPLE 118

N-[2-(4-Carbomethoxymethoxyphenyl)-1-methylethyl]-2-hydroxy-2-(3-chlorophenyl)morpholine 1.1 g (4.1 mmol) of N-[2-(4-carbomethoxymethoxyphenyl)-1-methylethyl]-2-hydroxy-ethanamine is stirred together with 0.95 g (4.1 mmol) of 3-chloro-phenacyl bromide and 1.2 g (12.3 mmol) of potassium hydrogen carbonate in 30 ml of acetone for 24 hours at ambient temperature. The mixture is then filtered, evaporated down and the evaporation residue is purified by column chromatography on silica gel (eluant: toluene/ethyl acetate=2:1). 15Yield: 1.0 g (57% of theory), M.p.: <20° C.
Calculated: C 62.93; H 6.24; N 3.33; Cl 8.44. Found: C 62.71; H 6.13; N 3.22; Cl 8.57.

According to $^1$H NMR there is a 50:50 mixture of the diastereomers.

400 MHz $^1$H NMR spectrum (CDCl$_3$): $\delta$=0.97 ppm (d)=—CH—CH$_3$; $\delta$=0.99 ppm (d) =—CH—CH$_3$.

The following are prepared analogously to Example 118:

118a) N-[2-(4-(2-Hydroxyethoxy)phenyl)-1-methylethyl]-2-hydroxy-2-(3-chlorophenyl)morpholine from 3-chloro-phenacyl bromide and N-[2-(4-(2-hydroxyethoxy)phenyl)-1-methylethyl]-2-hydroxyethanamine.

Yield: 50.6% of theory,
M.p.: <20° C.
Calculated: C 64.36; H 6.69; N 3.57; Cl 9.05. Found: C 64.26; H 6.57; N 3.41; Cl 9.37.

According to $^1$H NMR there is a 50:50 mixture of the diastereomers.

400 MHz $^1$H NMR spectrum (CDCl$_3$/CD$_3$OD): $\delta$=0.98 ppm (d)=—CH—CH$_3$; $\delta$=1.00 ppm (d)=— CH—CH$_3$.

118b) N-[2-(4-Methylaminocarbonylmethoxyphenyl)-1-methylethyl]-2-hydroxy-2-(3-chlorophenyl)morpholine from 3-chloro-phenacyl bromide and N-[2-(4-methylaminocarbonylmethoxyphenyl)-1-methylethyl]-2-hydroxyethanamine.

Yield: 53.7% of theory,
M.p.: <20° C.
Calculated: C 63.07; H 6.50; N 6.69 ; Cl 8.46; Found: C 62.88; H 6.41; N 6.57; Cl 8.58.

According to $^1$H NMR there is a 50:50 mixture of the diastereomers.

400 MHz 1H NMR spectrum (CDCl$_3$/CD$_3$OD): $\delta$=0.98 ppm (d)=—CH—CH$_3$; $\delta$=1.01 ppm (d)=— CH—CH$_3$.

118c) N-[2-(4-Carbomethoxymethoxyphenyl)-1-methylethyl]-2- hydroxy-2-(3-trifluoromethylphenyl)morpholine from 3-trifluoromethyl-phenacyl bromide and N-[2-(4-carbomethoxymethoxyphenyl)-1-methylethyl]-2-hydroxyethanamine.

Yield: 56% of theory,
M.p.: <20° C.
Calculated: C 60.92; H 5.78; N 3.09; Found: C 61.13; H 5.92; N 2.93.

According to $^1$H NMR there is a 50:50 mixture of the diastereomers.

400 MHz $^1$H NMR spectrum (CDCl$_3$/CD$_3$OD): $\delta$=0.98 ppm (d)=—CH—CH$_3$; $\delta$=1.00 ppm (d)=— CH—CH$_3$.

118d) N-[2-(4-Carbomethoxymethoxyphenyl)-1-methylethyl]-2-hydroxy-2-phenyl-morpholine
from phenacyl bromide and N-[2-(4-carbomethoxymethoxyphenyl)-1-methylethyl]-2-hydroxy-ethanamine.
Yield: 52.9% of theory,
M.p.: <20° C.
Calculated: C 68.55; H 7.86; N 3.63; Found: C 68.71; H 7.13; N 3.57.
According to $^1$H NMR there is a 50:50 mixture of the diastereomers.
400 MHz $^1$H NMR spectrum (CDCl$_3$/CD$_3$OD): δ=0.96 ppm (d)=—CH—CH$_3$; δ=0.99 ppm (d)=—CH—CH$_3$.

(118e) N-[2-(4-Carbomethoxymethoxyphenyl)-1-methylethyl]-2-hydroxy-2-(3-methylphenyl)morpholine
from 3-methyl-phenacyl bromide and N-[2-(4-carbomethoxymethoxyphenyl)-1-methylethyl]-2-hydroxyethanamine.
Yield: 59.6% of theory,
M p.: <20° C.
Calculated: C 69.15; H 7.32; N 3.51; Found: C 69.12; H 7.38; N 3.35.
According to $^1$H NMR there is a 50:50 mixture of the diastereomers.
400 MHz $^1$H NMR spectrum (CDC$_3$/CD$_3$OD): δ=0.97 ppm (d)=—CH—CH$_3$; δ=0.99 ppm (d)=—CH—CH$_3$.

(118f) N-[2-(4-Carbomethoxymethoxyphenyl)-1-methylethyl]-2-hydroxy-2-(2-trifluoromethyl-thiazol-4-yl)morpholine
from N-[2-(4-carbomethoxymethoxyphenyl)-1-methylethyl]-2-hydroxy-ethamine and 2-trifluoromethyl-4-bromoacetyl-thiazole.
Yield: 49% of theory,
M.p.: <20° C.
Calculated: C 52.16; H 5.03; N 6.09; Found: C 52.37; H 5.36; N 5.87.
According to $^1$H NMR there is a 50:50 mixture of the diastereomers.
400 MHz $^1$H NMR spectrum (CDCl$_3$/CD$_3$OD): δ=7.67 ppm (s, 0.5H); δ=7.72 ppm (s, 0.5H).

118g) N-[2-(4-Carbomethoxymethoxyphenyl)-1-methylethyl]-2-hydroxy-2-(2-chloro-thiazol-4-yl)-morpholine
from N-[2-(4-carbomethoxymethoxyphenyl)-1-methylethyl]-2- hydroxy-ethanamine and 2-chloro-4-bromoacetyl-thiazole.
Yield: 56% of theory,
M.p.: <20° C.
Calculated: C 53.45; H 5.42; N 6.56. Found: C 53.20; H 5.67; N 6.22.
According to $^1$H NMR there is a 40:60 mixture of the diastereomers.
400 MHz 1H NMR spectrum (CDCl$_3$/CD$_3$OD): δ=7.39 ppm (s, 0.4H); δ=7.42 ppm (s, 0.6H).

(118h) N-[2-(4-(2-Hydroxyethoxy)phenyl)-1-methylethyl]-2-hydroxy-2-(2-trifluoromethyl-thiazol-4-yl)morpholine
from N-[2-(4-(2-hydroxyethoxy)phenyl)-1-methylethyl]2-hydroxy-ethanamine and 2-trifluoromethyl-4-bromoacetyl-thiazole.
Yield: 20% of theory,
M.p.: <20° C.
Calculated: C 54.80; H 5.57; N 6.73. Found: C 54.65; H 5.641; N 6.64.
According to $^1$H NMR there is a 50:50 mixture of the diastereomers.
400 MHz $^1$H NMR spectrum (CDCl$_3$/CD$_3$OD): δ=7.80 ppm (s, 0.5H); δ=7.74 ppm (s, 0.5H).

(118i) N-[2-(4-Methylaminocarbonylmethoxyphenyl)-1-methyl- ethyl]-2-hydroxy-2-(2-trifluoromethyl-thiazol-4-yl)morpholine
from N-[2-(4-methylaminocarbonylmethoxyphenyl)-1-methylethyl]-2-hydroxy-ethanamine and 2-trifluoromethyl-4-bromoacetyl thiazole.
Yield: 45.6% of theory,
M.p.: <20° C.
Calculated: C 52.28; H 5.26; N 9.14. Found: C 52.17; H 5.23; N 9.18.
According to $^1$H NMR there is a 50:50 mixture of the diastereomers.
400 MHz $^1$H NMR spectrum (CDCl$_3$/CD$_3$OD): δ=7.81 ppm (s, 0.5H); δ=7.77 ppm (s, 0.5H).

(118k) N-[2-(4-(6-Hydroxy-n-hexyloxy)phenyl)-1-methylethyl]-2-hydroxy-2-(2-trifluoromethyl-thiazol-4-yl)-morpholine
from 2-trifluoromethyl-4-bromoacetyl-thiazole and N-[2-(4-(6-hydroxy-hexyloxy)phenyl)-1-methylethyl]-2-hydroxy-ethanamine.
Yield: 45% of theory,
M.p.: <20° C.
Calculated: C 56.54; H 6.40; N 5.73. Found: C 56.67; H 6.37; N 5.66.
According to $^1$H NMR there is a 50:50 mixture of the diastereomers.
400 MHz 1H NMR spectrum (CDCl$_3$/CD$_3$OD): δ=7.80 ppm (s, 0.5H); δ=7.78 ppm (s, 0.5H).

(118l) N-[2-(4-(2-Carbomethoxy-1-methyl-ethenyl)-phenyl)-1-methylethyl]-2-hydroxy-2-(3-chlorophenyl)morpholine
from 3-chloro-phenacyl bromide and N-[2-(4-(2-carbomethoxy-1-methyl-ethenyl)phenyl)-1-methylethyl]-2-hydroxy-ethanamine.
Yield: 50% of theory,
M.p.: <20° C.
Calculated: C 67.05; H 6.56; N 3.26; Cl 8.25. Found: C 67.12; H 6.56; N 3.27; Cl 8.44.
According to $^1$H NMR there is a 50:50 mixture of the diastereomers.
400 MHz $^1$H NMR spectrum (CDCl$_3$/CD$_3$OD): δ=1.01 ppm (d)=—CH—CH$_3$; δ=1.03 ppm (d)=—CH—CH$_3$.

(118m) N-[2-(4-Carbomethoxymethoxyphenyl)-1-methylethyl]-2-hydroxy-2-(4-amino-3-cyano-5-fluoro-phenyl)-morpholine
from 4-amino-3-cyano-5-fluoro-phenacyl bromide and N-[2-(4-carbomethoxymethoxyphenyl)-1-methylethyl]-2-hydroxy-ethanamine.
Yield: 47% of theory,
M.p.: <20° C.
Calculated: C 62.29; H 5.91; N 9.48. Found: C 62.28; H 5.93; N 9.30.
According to $^1$H NMR there is a 50:50 mixture of the diastereomers.
400 MHz $^1$H NMR spectrum (CDCl$_3$/CD$_3$OD): δ=0.965 ppm (d)=—CH—CH$_3$; δ=0.985 ppm (d)=—CH—CH$_3$.

(118n) N-[2-(4-(2-Ethoxyethoxy)phenyl)-1-methylethyl]-2-hydroxy-2-(2-trifluoromethyl-thiazol-4-yl)-morpholine
from N-[2-(4-(2-ethoxyethoxy)phenyl)-1-methylethyl]-2-hydroxy-ethanamine and 2-trifluoromethyl-4-bromoacetyl-thiazole.
Yield: 52% of theory,
M.p.: <20° C.

Calculated: C 54.77; H 5.91; N 6.08. Found: C 54.68; H 6.00; N 5.97.

According to $^1$H NMR there is a 50:50 mixture of the diastereomers.

400 MHz $^1$H NMR spectrum (CDCl$_3$/CD$_3$OD): δ=7.80 ppm (s, 0.5H); δ=7.73 ppm (s, 0.5H).

EXAMPLE 119

N-[2-(4-Carboxymethoxyphenyl)-1-methylethyl]-2-hydroxy-2-(3-methylphenyl)morpholine 0.5 g (1.25 mmol) of N-[2-(4-carbomethoxymethoxyphenyl)-1-methylethyl]-2-hydroxy-2-(3-methylphenyl)morpholine is dissolved in 5 ml of ethanol and after the addition of 3 ml of 1N sodium hydroxide solution the mixture is stirred at ambient temperature (about 1 hour) until the chromatograph shows that there is no starting material left. Then it is neutralised by the addition of 3 ml of 1N hydrochloric acid and extracted with chloroform. The extracts are dried, concentrated by evaporation and the evaporation residue is purified by column chromatography on silica gel (eluant: ethyl acetate/methanol=2:1).

Yield: 0.32 g (66% of theory),
M.p.: 137°-140° C.
Calculated: C 68.55; H 7.06; N 3.63. Found: C 68.41; H 7.12; N 3.44.

According to $^1$H NMR there is a 50:50 mixture of the diastereomers.

400 MHz $^1$H NMR spectrum (CDCl$_3$/CD$_3$OD): δ=0.975 ppm (d)=—CH—CH$_3$; δ=0.995 ppm (d)=—CH—CH$_3$.

Analogously to Example 119 the following are prepared:

(119a) N-[2-(4-Carboxymethoxyphenyl)-1-methylethyl]-2-hydroxy-2-(3-chlorophenyl)morpholine from N-[2-(4-carbomethoxymethoxyphenyl)-1-methylethyl]-2-hydroxy-2-(3-chlorophenyl)morpholine.

Yield: 26.3% of theory,
M.p.: 90°-95° C.
Calculated: C 62.14; H 5.96; N 3.45; Cl 8.73. Found: C 62.13; H 5.89; N 3.28; Cl 8.65.

According to $^1$H NMR there is a 50:50 mixture of the diastereomers.

400 MHz $^1$H NMR spectrum (CDCl$_3$): δ=0.99 ppm (d)=—CH—CH$_3$; δ=1.02 ppm (d)=—CH—CH$_3$.

(119b) N-[2-(4-Carboxymethoxyphenyl)-1-methylethyl]-2-hydroxy-2-(2-trifluoromethyl-thiazol-4-yl)morpholine from N-[2-(4-carbomethoxymethoxyphenyl)-1-methylethyl]-2-hydroxy-2-(2-trifluoromethyl-thiazol-4-yl)morpholine.

Yield: 50% of theory,
M.p.: 80° C.
Calculated: C 51.11; H 4.74; N 6.28. Found: C 50.82; H 4.63; N 6.16.

According to $^1$H NMR there is a 40:60 mixture of the diastereomers.

400 MHz $^1$H NMR spectrum (CDCl$_3$/CD$_3$OD): δ=7.94 ppm (s, 0.4H); δ=7.98 ppm (s, 0.6H).

EXAMPLE 120

N-[2-(4-Aminocarbonylmethoxyphenyl)-1-methylethyl]-2-hydroxy-2-(3-chlorophenyl)morpholine 2.03 g (4.76 mmol) of N-[2-(4-carbomethoxymethoxyphenyl)-1-methylethyl]-2-hydroxy-2-(3-chlorophenyl)morpholine is dissolved in 20 ml of ammonia-saturated methanol and stirred for 24 hours at ambient temperature. The mixture is then evaporated down and the evaporation residue is purified by column chromatography on silica gel (eluant: ethyl acetate/cyclohexane=3:1).

Yield: 810 mg (42.6% of theory),
M.p.: <20° C.
Calculated: C 62.30; H 6.22; N 6.92. Found: C 62.21; H 6.25; N 6.87.

According to $^1$H HMR there is a 50:50 mixture of the diastereomers.

400 MHz $^1$H NMR spectrum (CDCl$_3$/CD$_3$OD): δ=0.98 ppm (d)=—CH—CH$_3$; δ=1.01 ppm (d)=—CH—CH$_3$.

EXAMPLE 121

N-[2-(4-Carbomethoxymethoxyphenyl)-1-methylethyl]-2-hydroxy-2-phenyl-6-(2-trifluoromethyl-thiazol-4-yl)morpholine To a suspension of 0.38 g (0.9 mmol) of N-[2-(4-carbomethoxymethoxyphenyl)-1-methylethyl]-2-hydroxy-2-(2-trifluoromethyl-thiazol-4-yl)ethanamine [pair of diastereomers A] and 0.27 g (2.7 mmol) of potassium hydrogen carbonate in 4 ml of acetone, 0.18 g (0.9 mmol) of phenacyl bromide is added and stirred for 50 hours at ambient temperature. The mixture is then evaporated to dryness and the base is purified over a siliaa gel column using toluene/ethyl acetate 8:2 as eluant.

Yield: 0.15 g (31% of theory),
M.p.: <20° C.
Calculated: C 58.20; H 5.07; N 5.22. Found: C 57.95; H 5.14; N 5.08.

According to 1H NMR spectrum there is a 20:80 mixture of the diastereomers.

400 MHz $^1$H NMR spectrum (CDCl$_3$/CD$_3$OD): δ=1.00 ppm (d, 0.8H)=—CH—CH$_3$; δ=1.05 ppm (d, 0.2H)=—CH—CH$_3$.

The following are prepared analogously to Example 121:

(121a) N-[2-(4-Carbomethoxymethoxyphenyl)-1-methyl ethyl]-2-hydroxy-2-(3-chlorophenyl)-6-(2-trifluoromethyl-thiazol-4-yl)morpholine from N-[2-(4-carbomethoxymethoxyphenyl)-1-methylethyl]-2-hydroxy-2-(2-trifluoromethyl-thiazol-4-yl)-ethanamine (pair of diasteromers A) with 3-chlorophenacyl bromide and potassium hydrogen carbonate in acetone.

Yield: 73% of theory,
M.p.: <20° C.
Calculated: C 54.68; H 4.59; N 4.91. Found: C 54.79; H 4.52; N 4.77.

According to $^1$H NMR there is a 96:4 mixture of the diastereomers.

400 MHz $^1$H NMR spectrum (CDCl$_3$/CD$_3$OD): δ=1.01 ppm (d, 0.96H)=—CH—CH$_3$; δ=1.05 ppm (d, 0.04H)=—CH—CH$_3$.

(121b) N-[2-(4-Carbomethoxymethoyphenyl)-1-methylethyl]-2-hydroxy-2,6-bis(2-trifluoromethyl-thiazol-4-yl)morpholine from N-[2-(4-carbomethoxymthoxyphenyl)-1-methylethyl]-2-hydroxy-2-(2-trifluoromethyl-thiazol-4-yl)-ethanamine (pair of diastereomers A) with 2-trifluoromethyl-4-bromoacetyl-thiazole and potassium hydrogen carbonate in acetone.

Yield: 65% of theory,
M.p.: <20° C.

Calculated: C 47.13; H 3.79; N 6.87. Found: C 46.97; H 3.78; N 6.68.

According to $^1$H NMR spectrum there is a pair of diastereomers.

400 MHz $^1$H NMR spectrum (CDCl$_3$/CD$_3$OD): δ=1.035 ppm (d)=—CH—CH$_3$.

EXAMPLE 122

Coated tablet containing 10 mg of N-[2-(4-carbomethoxymethoxyphenyl)-1-methylethyl?-2-hydroxy-2-(3chlorophenyl) morpholine Composition:
1 coated tablet contains:

| | |
|---|---|
| (1) Active substance | 10.0 mg |
| (2) Lactose | 69.0 mg |
| (3) Corn starch | 35.0 mg |
| (4) Polyvinylpyrrolidone | 5.0 mg |
| (5) Magnesium stearate | 1.0 mg |
| | 120 mg |

Method (1)+(2)+(3) are mixed together and moistened with (4) in an aqueous solution. The moist mass is passed through a screen with a mesh size of 1.6 mm and dried at 45° C. in a circulating air dryer. The dry granules are passed through a 1 mm mesh screen and mixed with (5). The finished mixture is compressed to form tablet cores.

Weight of core: 120.0 mg
Diameter: 7.0 mm
Radius of curvature: 6.0 mm

The tablet cores thus produced are coated in known manner with a coating consisting essentially of sugar and talc. This coating may also contain dye extracts. The finished coated tablets are polished with wax.

Weight of coated tablet: 180.0 mg

EXAMPLE 123

Coated tablet containing 50 mg of N-[2-(4-carbomethoxy methoxyphenyl)-1-methylethyl?-2-hydroxy-2-(3-chloro phenyl)morpholine Composition:
1 coated tablet contains:

| | |
|---|---|
| (1) Active substance | 50.0 mg |
| (2) Lactose | 110.8 mg |
| (3) Corn starch | 50.0 mg |
| (4) Polyvinylpyrrolidone | 8.0 mg |
| (5) Magnesium stearate | 1.2 mg |
| | 220.0 mg |

Method
The method is analogous to that of Example 122.
Weight of core: 220.0 mg
Diameter: 9.0 mm
Radius of curvature: 8.0 mm
Weight of coated tablet: 300.0 mg

EXAMPLE 124

Tablets containing 150 mg of N-[2-(4-carbomethoxymethoxy phenyl)-1-methylethyl]-2-hydroxy-2-(3-chlorophenyl)-morpholine Composition:
1 tablet contains

| | |
|---|---|
| (1) Active substance | 150.0 mg |
| (2) Lactose | 86.0 mg |
| (3) Corn starch | 50.8 mg |
| (4) Microcrystalline cellulose | 25.0 mg |
| (5) Polyvinylpyrrolidone | 7.0 mg |
| (6) Magnesium stearate | 1.2 mg |
| | 320.0 mg |

Method (1)+(2)+(3)+(4)+(5) are mixed together and moistened with water. The moist mass is passed through a 1.6 mm mesh screen and dried at 45° C. The dry granules are passed through the same screen again and mixed with (6). Tablets are compressed from the finished mixture.

Weight of tablet: 320.0 mg
Diameter: 10.0 mm

The tablets are provided with a dividinq notch to make it possible to break them in half.

EXAMPLE 125

Hard gelatin capsules containing 100 mg of N-[2-(4-carbomethoxymethoxyphenyl)-1-methylethyl]-2-hydroxy-2-(3-chlorophenyl)morpholine Composition:
1 capsule contains:
Capsule shell: hard gelatin capsules size 3
Capsule contents:

| | |
|---|---|
| (1) Active substance | 100.0 mg |
| (2) Lactose × 1H$_2$O | 38.0 mg |
| (3) Dried corn starch | 60.0 mg |
| (4) Magnesium stearate | 2.0 mg |
| Weight of capsule filling: | 200.0 mg |
| (5) Distilled water q.s. | |

Method A small amount of lactose is dissolved in a quantity of about 10% in distilled water (granulating liquid). The active substance, the remaining lactose and the corn starch are mixed together and moistened with the granulating liquid. The mass is screened and dried and, after being screeed once more, homogeneously mixed with magnesium stearate. The fine granules are packed into capsules in a suitable machine.

EXAMPLE 126

Hard gelatin capsules containing 200 mg of N-[2-(4-carbomethoxymethoxyphenyl)-1-methylethyl]-2-hydroxy-2-(3-chlorophenyl)morpholine Composition:
Capsule shell: hard gelatin capsules size 1
Capsule contents:

| | |
|---|---|
| (1) Active substance | 200.0 mg |
| (2) Lactose × 1H$_2$O | 47.0 mg |
| (3) Dried corn starch | 70.0 mg |
| (4) Magnesium stearate | 3.0 mg |
| Weight of capsule filling: | 320.0 mg |
| (5) Distilled water q.s. | |

Method A small amount of lactose is dissolved in a concentration of about 10% in distilled water (granulating liquid). The active substance, the remaining lactose and corn starch are mixed together and moistened with the gran-

What is claimed is:

1. A compound of the formula:

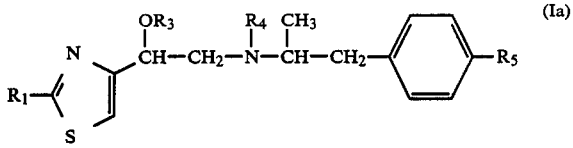

in which $R_1$ is selected from the group consisting of chloro, methyl and trifluoromethyl, $R_3$ is hydrogen, $R_4$ is selected from the group consisting of hydrogen, methyl, 2-hydroxyethyl and carbethoxymethyl, $R_5$ is selected from the group consisting of carboxymethoxy, carbomethoxymethoxy, ethoxy-carbonylmethoxy, aminocarbonylmethoxy, methylamino-carbonylmethoxy, 2-methylaminoethoxy, 2-hydroxyethoxy and 2-carbomethoxy-1-methylethenyl, or an optical isomers or diastereomers thereof or a physiologically acceptable acid addition salt thereof with an organic or organic acid.

2. N-[2-(4-Carbomethoxymethoxyphenyl)-1-methylethyl]-2-hydroxy-2-(2-trifluoromethyl-thiazol-4-yl)ethanamine, or the optical isomer, diastereomer or physiologically acceptable acid addition salt thereof.

3. N-[(4-Carbomethoxymethoxyphenyl)-1-methylethyl]-N-(2-hydroxy-ethyl)-2-hydroxy-2-(2-trifluoromethyl-thiazol-4-yl)-ethanamine, or the optical isomer, diastereomer or physiologically acceptable acid addition salt thereof.

4. N-[2-(4-(2-Hydroxyethoxy)phenyl)-1-methylethyl]-2-hydroxy-2-(2-trifluoromethyl-thiazol-4-yl)ethanamine, or the optical isomer, diasteromer or physiologically acceptable acid addition salt thereof.

5. A compound of the formula:

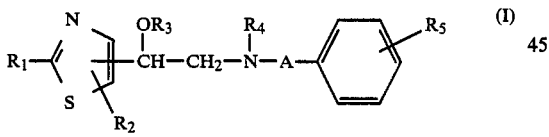

in which

A is n-alkylene of 2 to 3 carbons, optionally mono- or di-substituted in the 1-position with methyl or ethyl;

$R_1$ is selected from the group consisting of hydrogen, fluoro, chloro, bromo, trifluoromethyl, alkyl, phenyl, piperidino, amino, alkylamino, dialkylamino, alkanoylamino and benzoylamino;

$R_2$ is hydrogen or alkyl;

$R_3$ is hydrogen or alkyl, optionally substituted in the 2- or 3-position by hydroxyl;

$R_4$ is selected from the group consisting of hydrogen, alkyl, optionally substituted in the 1-, 2- or 3-position by a member selected from the group consisting of phenyl, carboxyl, alkoxycarbonyl, cyano, and, in the 2- or 3-position, hydroxyl, and alkenyl; and $R_5$ is selected from the group consisting of hydroxyl, alkoxy, carboxyl, alkoxycarbonyl, aminocarbonyl, alkylaminocarbonyl, dialkylaminocarbonyl, alkoxy having 1 to 6 carbon atoms and substituted by a terminal member selected from the group consisting of carboxyl, alkoxycarbonyl, aminocarbonyl, alkylaminocarbonyl and dialkylaminocarbonyl, alkoxy having 2 to 7 carbons and substituted by a terminal member selected from the group consisting of carboxyl, alkoxy carbonyl, amino carbonyl, alkylaminocarbonyl and dialkylaminocarbonyl, alkoxy having 2 to 7 carbons and substituted by a terminal member selected from the group consisting of hydroxyl, alkoxy, phenylalkoxy, amino, alkylamino, dialkylamino, pyrrolidino, piperidino and hexamethyleneimino, 2-carboxy-ethenyl, 2-carboxy-1-methyl-ethenyl, 2-carboxy-2-methyl-ethenyl, 2-carboxy-1-ethyl-ethenyl, 2-carboxy-1-n-propyl-ethenyl, 2-methoxycarbonyl-ethenyl, 2-methoxycarbonyl-1-methyl-ethenyl, 2-ethoxycarbonyl-ethenyl, 2-ethoxycarbonyl-1-methyl-ethenyl and 2-isopropoxycarbonyl-ethenyl, wherein said alkyl, alkoxy and alkanoyl each contain, unless indicated otherwise, 1 to 3 carbons, and said alkenyl contains 3 to 5 carbons, or an optical isomers or diastereomers thereof or a physiologically acceptable acid addition salt thereof with an inorganic or organic acid.

6. The compound as defined in claim 5 wherein:

A is ethylene, n-propylene, 1-methyl-ethylene or 1-methyl-n-propylene;

$R_1$ is selected from the group consisting of hydrogen, chloro, alkyl, trifluoromethyl, phenyl, amino, methylamino, dimethylamino, piperidino, acetylamino and benzoylamino;

$R_2$ is hydrogen or methyl;

$R_3$ is hydrogen or methyl;

$R_4$ is selected from the group consisting of hydrogen, methyl, 2-hydroxy-ethyl, carboxymethyl, carbethoxymethyl, and benzyl; and $R_5$ is selected from the group consisting of hydroxy, methoxy, carboxy, methoxycarbonyl, ethoxycarbonyl, aminocarbonyl, carboxymethoxy, methoxycarbonylmethoxy, ethoxycarbonylmethoxy, aminocarbonylmethoxy, methylaminocarbonylmethoxy, 2-hydroxy-ethoxy, 2-ethoxy-ethoxy, 2-phenethoxy-ethoxy, 2-amino-ethoxy, 2-methylamino-ethoxy, 2-(1-piperidino)ethoxy, 6-hydroxy-n-hexoxy and 2-carbomethoxy-1-methyl-ethenyl;

or an optical isomers or diastereomers thereof or a physiologically acceptable acid addition salt thereof with an inorganic or organic acid.

7. A compound of the formula:

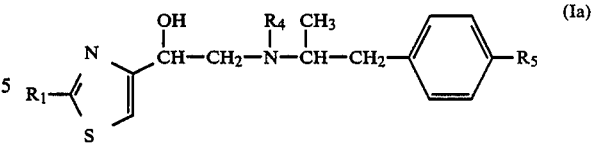

in which $R_1$ is selected from the group consisting of chloro, methyl and trifluoromethyl;

$R_4$ is selected from the group consisting of hydrogen, methyl, 2-hydroxy-ethyl and carbethoxymethyl; and $R_5$ is selected from the group consisting of carboxymethoxy, carbomethoxymethoxy, ethoxycarbonylmethoxy, aminocarbonylmethoxy, methylaminocarbonylmethoxy, 2-methylamino-ethoxy, 2-hydroxyethoxy and 2-carbomethoxy-1-methyl-ethenyl;

or an optical isomers or diastereomers thereof or a physiologically acceptable acid addition salt thereof with an inorganic or organic acid.

8. A pharmaceutical composition comprising an effective blood sugar lowering amount of a compound as recited in claim 5 in combination with a nontoxic, pharmaceutically acceptable carrier.

9. A pharmaceutical composition comprising an effective blood sugar lowering amount of a compound as recited in claim 7 in combination with a nontoxic, pharmaceutically acceptable carrier.

10. A pharmaceutical composition comprising an effective blood sugar lowering amount of a compound as recited in claim 1 in combination with a nontoxic, pharmaceutically acceptable carrier.

11. A method of treating an individual affected with diabetes mellitus which comprises administering to said individual an effective blood sugar lowering amount of a compound as recited in claim 5.

12. A method of treating an individual afflicted with diabetes mellitus which comprises administering to said individual an effective blood sugar lowering amount of a compound as recited in claim 7.

13. A method of treating an individual afflicted with diabetes mellitus which comprises administering to said individual an effective blood sugar lowering amount of a compound as recited in claim 1.

* * * * *